US012799216B2

(12) United States Patent
Akkad et al.

(10) Patent No.: US 12,799,216 B2
(45) Date of Patent: *Nov. 17, 2026

(54) ANTIBODIES SPECIFIC TO PROLACTIN RECEPTOR AND THERAPEUTIC USES THEREOF

(71) Applicant: Absci Corporation, Vancouver, WA (US)

(72) Inventors: Amer-Denis Akkad, Witten (DE); Amir Shanehsazzadeh, Andover, MA (US); Andrea K. Steiger, Vancouver, WA (US); Christian Stegmann, Bassersdorf (CH); David A. Spencer, Vancouver, WA (US); John M. Sutton, Vancouver, WA (US); Marcin L. Ura, Camas, WA (US); Sharrol Bachas, Oceanside, CA (US); Vincent Blay, Cambridge, MA (US); Yiu Huen Tsang, Ridgefield, WA (US)

(73) Assignee: Absci Corporation, Vancouver, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/413,229

(22) Filed: Dec. 9, 2025

(65) Prior Publication Data

US 2026/0217841 A1 Jul. 30, 2026

Related U.S. Application Data

(60) Provisional application No. 63/912,667, filed on Nov. 6, 2025, provisional application No. 63/744,486, filed on Jan. 13, 2025, provisional application No. 63/730,261, filed on Dec. 10, 2024.

(51) Int. Cl.
*C07K 16/28* (2006.01)
*A61P 17/00* (2006.01)
*A61K 39/00* (2006.01)

(52) U.S. Cl.
CPC .......... *C07K 16/2866* (2013.01); *A61P 17/00* (2018.01); *A61K 2039/505* (2013.01); *C07K 2317/622* (2013.01)

(58) Field of Classification Search
None
See application file for complete search history.

(56) References Cited

U.S. PATENT DOCUMENTS 9,241,989 B2 * 1/2016 Otto .......................... A61P 5/30

FOREIGN PATENT DOCUMENTS

| | | | |
|---|---|---|---|
| EP | 2567978 | A1 | 3/2013 |
| WO | 2012/163932 | A1 | 12/2012 |
| WO | 2019/011719 | A1 | 1/2019 |

* cited by examiner

*Primary Examiner* — Nelson B Moseley, II
*Assistant Examiner* — James Ryland Melchior
(74) *Attorney, Agent, or Firm* — Mintz, Levin, Cohn, Ferris, Glovsky and Popeo, P.C.

(57) ABSTRACT

The present disclosure provides antibodies that bind to the prolactin receptor (PRLR), nucleic acids encoding the antibodies, methods of production using host cells, and its applications, including applications in pharmaceutical compositions for the treatment of PRLR-associated diseases.

20 Claims, 29 Drawing Sheets

Specification includes a Sequence Listing.

ANTIBODIES SPECIFIC TO PROLACTIN RECEPTOR AND THERAPEUTIC USES THEREOF

CROSS REFERENCE TO RELATED APPLICATIONS

This application claims the benefit of the filing dates of U.S. Provisional Application No. 63/912,667, filed Nov. 6, 2025, U.S. Provisional Application No. 63/744,486, filed Jan. 13, 2025, and U.S. Provisional Application No. 63/730, 261, filed Dec. 10, 2024, the entire contents of each of which are incorporated by reference herein.

SEQUENCE LISTING

The instant application contains a Sequence Listing which has been filed electronically in XML format and is hereby incorporated by reference in its entirety. Said XML copy, created on Nov. 19, 2025, is named 064802-501001US_Seq-Listing_ST26 and is 172,616 bytes in size.

BACKGROUND

Prolactin (PRL) is a protein hormone of the anterior pituitary gland and can also be synthesized in other tissues. The prolactin signaling pathway is initiated by the binding of prolactin with the prolactin receptor (PRLR), a member of class I cytokine receptor superfamily, which is expressed in a variety of tissues. The primary mechanism involved in PRL-PRLR activation is the JAK/STAT pathway. Prolactin receptor (PRLR) expression is associated with the progression of several hormone-dependent cancers, such as breast, prostate, cervical, ovarian, and pancreatic cancers, hyperprolactinemia, which is often presented with endometriosis, and androgenetic alopecia. Aberrant activation of PRLR signaling can contribute to the progression of tumors. PRLR is a promising target in cancer therapy and other disease indications where upregulation of PRLR is noted. However, existing antibodies may not have optimal specificity for the prolactin receptor, and cross-reactivity with other receptors or unintended tissues can lead to off-target effects and diminished efficacy.

Therefore, there is a need for the development of highly specific prolactin receptor antibody therapies with improved delivery mechanisms and minimized immunogenicity.

SUMMARY

The present disclosure provides antibodies that bind to the prolactin receptor (PRLR) (anti-PRLR antibodies), which are designed via AI modeling on a parent anti-PRLR antibody (AB000) to improve bioactivity and developability of the parent antibody. Exemplary anti-PRLR antibodies disclosed herein exhibit superior features such as high binding affinity, high solubility, and high stability as compared with the parent antibody. Further, the exemplary anti-PRLR antibodies showed reduced or no binding activities to Fcγ receptors, absence of ADCC activity, enhanced binding affinity to FcRn at pH 5.8 relative to the parent antibody and low binding to FcRn at pH 7.4; and enhanced half-live relative to the parent antibody. In addition, exemplary anti-PRLR antibodies provided herein also exhibited superior effects in enhancing hair growth in a mouse model as reported herein.

Accordingly, provided herein are anti-PRLR antibodies, nucleic acids encoding the antibodies, methods of production using host cells, pharmaceutical compositions comprising such, and applications of the anti-PRLR antibodies in the treatment of PRLR-associated diseases.

In some aspects, the present disclosure provides an antibody binding to prolactin receptor (PRLR), comprising a heavy chain variable region (VH) and a light chain variable region (VL).

The VH comprises (i) a heavy chain complementarity determining region 1 (HCDR1) consisting of the amino acid sequence of $X_1X_2WX_3H$, wherein $X_1$ is D or S; $X_2$ is F, H, or Y; and $X_3$ is M or L; (ii) a HCDR2 consisting of the amino acid sequence of DISR$X_4X_5$PY$X_6X_7$YADSVKG (SEQ ID NO: 131), wherein $X_4$ is I or L; $X_5$ is K or S; $X_6$ is H or T; and $X_7$ is G or N; and (iii) a HCDR3 consisting of the amino acid sequence of G$X_8$DA$X_9$RM$X_{10}X_{11}$ (SEQ ID NO: 132), wherein $X_8$ is M or L, is $X_9$ is K or R; $X_{10}$ is D or S; and $X_{11}$ is H or Y.

The VL comprises (i) a light chain CDR1 (LCDR1) consisting of the amino acid sequence of TGS$X_{12}X_{13}$N$X_{14}X_{15}X_{16}$GYV$X_{17}$H (SEQ ID NO: 133), wherein $X_{12}$ is A, G, S, T; $X_{13}$ is S or T; $X_{14}$ is I or L; $X_{15}$ is G or H; $X_{16}$ is A, G, or H; and $X_{17}$ is N or V; (ii) a LCDR2 consisting of the amino acid sequence of R$X_{18}X_{19}X_{20}X_{21}$PS, wherein $X_{18}$ is H or N; $X_{19}$ is H or N; $X_{20}$ is L, Q, V; and $X_{21}$ is K or R; and (iii) a LCDR3 consisting of the amino acid sequence of A$X_{22}X_{23}$DD$X_{24}X_{25}X_{26}X_{27}$WL (SEQ ID NO: 134), wherein $X_{22}$ is A or S; $X_{23}$ H or W; $X_{24}$ is E, H, R, or S; $X_{25}$ is H, L, R, S, or V; $X_{26}$ is H, M, N, Q, S, T; and $X_{27}$ is A or G.

In some embodiments, the VH comprises the HCDR1, in which $X_1$ is D or S; $X_2$ is Y; and $X_3$ is M or L; the HCDR2, in which $X_4$ is L; $X_5$ is K or S; $X_6$ is T; and $X_7$ is G or N; and the HCCDR3, in which $X_8$ is M or L; $X_9$ is R; $X_{10}$ is D or S; and $X_{11}$ is Y. In some examples, $X_1$ is D or S; $X_2$ is Y; and $X_3$ is M or L in the HCDR1; $X_4$ is L; $X_5$ is K or S; $X_6$ is T; and $X_7$ is N in the HCDR2; and $X_8$ is M or L; $X_9$ is R; $X_{10}$ is D or S; and $X_{11}$ is Y in the HCDR3.

Alternatively or in addition, the VL comprises the LCDR1, in which $X_{12}$ is G, S, or T; $X_{13}$ is S or T; $X_{14}$ is I or L; $X_{15}$ is G; $X_{16}$ is A, G, or H; and $X_{17}$ is V; the LCDR2, in which $X_{18}$ is H or N; $X_{19}$ is H or N; $X_{20}$ is L or Q; and $X_{21}$ is R; and LCDR3, in which $X_{22}$ is A or S; $X_{23}$ H or W; $X_{24}$ is E, R, or S; $X_{25}$ is H, L, or R; $X_{26}$ is N, M, or Q; and $X_{27}$ is A or G. In some examples, $X_{12}$ is G or S; $X_{13}$ is S or T; $X_{14}$ is I; $X_{15}$ is G; $X_{16}$ is A, G, or H; and $X_{17}$ is V in LCDR1; $X_{18}$ is N; $X_{19}$ is N; $X_{20}$ is L or Q; and $X_{21}$ is R in LCDR2; and $X_{22}$ is A or S; $X_{23}$ W; $X_{24}$ is E, R, or S; $X_{25}$ is H, L, or R; $X_{26}$ is N or Q; and $X_{27}$ is A or G in LCDR3.

In some examples, the anti-PRLR antibody provided herein may comprise the HCDR1, HCDR2, and HCDR3 set forth in Table 1. Alternatively, or in addition, the anti-PRLR antibody provided herein may comprise the LCDR1, LCDR2, and LCDR3 set forth in Table 2.

In some examples, the anti-PRLR antibody provided herein comprises the HCDR1, HCDR2, and HCDR3 set forth in SEQ ID NOs: 2, 7, and 12, respectively and the LCDR1, LCDR2, and LCDR3 set forth in SEQ ID NOs: 18, 29, and 34, respectively.

In some examples, the anti-PRLR antibody provided herein comprises the HCDR1, HCDR2, and HCDR3 set forth in SEQ ID NOs: 2, 9, 14, respectively, and the LCDR1, LCDR2, and LCDR3 set forth in SEQ ID NOs: 23, 28, and 33, respectively.

In some examples, the anti-PRLR antibody provided herein comprises the HCDR1, HCDR2, and HCDR3 set forth in SEQ ID NOs: 4, 9, 15, respectively, and the LCDR1, LCDR2, and LCDR3 set forth in SEQ ID NOs: 26, 28, and 41, respectively.

In some examples, the anti-PRLR antibody provided herein comprises the HCDR1, HCDR2, and HCDR3 set forth in SEQ ID NOs: 2, 8, 12, respectively, and the LCDR1, LCDR2, and LCDR3 set forth in SEQ ID NOs: 21, 28, and 38, respectively.

In some examples, the anti-PRLR antibody provided herein comprises the HCDR1, HCDR2, and HCDR3 set forth in SEQ ID NOs: 4, 9, 15, respectively, and the LCDR1, LCDR2, and LCDR3 set forth in SEQ ID NOs: 24, 28, and 40, respectively.

In some examples, the anti-PRLR antibody provided herein comprises the HCDR1, HCDR2, and HCDR3 set forth in SEQ ID NOs: 4, 9, 15, respectively, and the LCDR1, LCDR2, and LCDR3 set forth in SEQ ID NOs: 25, 31, and 40, respectively.

In some examples, the anti-PRLR antibody provided herein comprises the HCDR1, HCDR2, and HCDR3 set forth in SEQ ID NOs: 2, 9, 14, respectively, and the LCDR1, LCDR2, and LCDR3 set forth in SEQ ID NOs: 17, 28, and 42, respectively.

In any of the anti-PRLR antibodies disclosed herein, the VH may comprise heavy chain framework regions (HC FRs) derived from IGHV3-66*01. Alternatively or in addition, the VL of the antibody may comprise light chain framework regions (LC FRs) derived from IGKV4-1*01.

In some embodiments, the VH comprises the heavy chain framework regions as below: (a) HC FR1 set forth as QVQLVQSGGGLVQPGGSLRLSCAASGF$X_{28}X_{29}X_{30}$ (SEQ ID NO: 135), wherein $X_{28}$ is S or T; $X_{29}$ is H or Y; and $X_{30}$ is H, S, or V; (b) HC FR2 set forth as WVRQAPGKGLEW$X_{31}$S (SEQ ID NO: 136), wherein $X_{31}$ is M or V; (c) HC FR3 set forth as GRFTISRDNAKNTLYLQLNSLRAEDTAMYYC$X_{32}X_{33}$ (SEQ ID NO: 137), wherein $X_{32}$ is A or S; and $X_{33}$ is K or R; and (d) HC FR4 set forth as WGQGTLVTVSS (SEQ ID NO: 55). In some examples, $X_{28}$ is S or T; $X_{29}$ is H or Y; $X_{30}$ is H or S; $X_{31}$ is M or V; $X_{32}$ is A; and/or $X_{33}$ is R.

Alternatively or in addition, the VL may comprise the light chain framework regions as below: (a) LC FR1 set forth as DIQLTQSPSSVSVSVGERVTIDC (SEQ ID NO: 57); (b) LC FR2 set forth as WYQQKPGQAPQ$X_{35}X_{36}X_{37}X_{38}$ (SEQ ID NO: 138), wherein $X_{35}$ is H or L; $X_{36}$ is K or L; $X_{37}$ is I or M; and $X_{38}$ is F or Y; (c) LC FR3 set forth as GVPDRFSGSKSGT-DATLTISSLQAEDAAVYYC (SEQ ID NO: 64); and (d) LC FR4 set forth as FGQGTKLEIK (SEQ ID NO: 66).

In some examples, the anti-PRLR antibodies provided herein may comprise the VH shown in Table 5; and/or the VL shown in Table 5. In one specific example, the antibody comprises the VH comprising SEQ ID NO: 68 and the VL comprising SEQ ID NO: 83. In another specific example, the antibody comprises the VH comprising SEQ ID NO: 73 and the VL comprising SEQ ID NO: 89. In yet another example, the antibody comprises the VH comprising SEQ ID NO: 79 and the VL comprising SEQ ID NO: 94. In still another example, the antibody comprise the VH comprising SEQ ID NO: 72 and the VL comprising SEQ ID NO: 87. In another example, the antibody comprises the VH comprising SEQ ID NO: 75 and the VL comprising SEQ ID NO: 90. In yet another example, the antibody comprises the VH comprising SEQ ID NO: 75 and the VL comprising SEQ ID NO: 91. In another example, the antibody comprises the VH comprising SEQ ID NO: 80 and the VL comprising SEQ ID NO: 95.

Any of the anti-PRLR antibodies provided herein may be a full-length antibody or an antigen-binding fragment thereof (e.g., those disclosed herein). Alternatively, the antibody may be a single chain variable fragment (scFv).

In some embodiments, the anti-PRLR antibody provided herein is a full-length antibody, which is an IgG molecule. Such an antibody may comprise a heavy chain comprising the VH and a heavy chain constant region of an IgG1 molecule and a light chain comprising the VL and a light chain constant region. In some instances, the heavy chain constant region can be a wild-type IgG1 constant region. In other instances, the heavy chain constant region may be a variant of a wild-type counterpart. For example, the heavy chain constant region can be a variant comprising one or more mutations at positions 234 (e.g., L234A), 235 (e.g., L235A), 265 (e.g., D265S), 428 (e.g., M428L), and 434 (e.g., N434S), following the EU numbering system. In some specific examples, the heavy chain constant region comprises any one of sequences set forth in SEQ ID NOs: 97-98. Alternatively, or in addition, the light chain constant region comprising any one of sequences set forth in SEQ ID NOs: 99-100.

Exemplary anti-PRLR antibodies provided herein may comprise: (a) a heavy chain comprising SEQ ID NO: 102 and a light chain comprising SEQ ID NO: 117; (b) a heavy chain comprising SEQ ID NO: 107 and a light chain comprising SEQ ID NO: 123; (c) a heavy chain comprising SEQ ID NO: 113 and a light chain comprising SEQ ID NO: 128; (d) a heavy chain comprising SEQ ID NO: 106 and a light chain comprising SEQ ID NO: 121; (e) a heavy chain comprising SEQ ID NO: 109 and a light chain comprising SEQ ID NO: 124; (f) a heavy chain comprising SEQ ID NO: 109 and a light chain comprising SEQ ID NO: 125; and (g) a heavy chain comprising SEQ ID NO: 114 and a light chain comprising SEQ ID NO: 129.

In some aspects, provided herein is an antibody binding to prolactin receptor (PRLR) (anti-PRLR antibody), the antibody comprising:

- (a) a heavy chain variable region (VH) comprising
  - (i) a heavy chain complementarity determining region 1 (HCDR1) consisting of the amino acid sequence of $X_1X_2WX_3H$, wherein $X_1$ is D, S, or E; $X_2$ is F, H, Y, V, M, T, S, or A; and $X_3$ is M, L, or F;
  - (ii) a HCDR2 consisting of the amino acid sequence of $DZ_1SRX_4X_5Z_2Z_3X_6X_7YZ_4Z_5Z_6Z_7Z_8Z_9$(SEQ ID NO: 142), wherein $X_4$ is I, L, F, V, or M; $X_5$ is K, S, L, N, A, G, Q, P, Y, T, V, M, I, W, E, D, F, R, or H; $X_6$ is H, T V, R, M, or S; $X_7$ is G, N, A, G, S, or Q; $Z_1$ is I or V; $Z_2$ is P, G, D, or S; $Z_3$ is Y, W, or F; $Z_4$ is A, K, L, H, I, M, V, or R, $Z_5$ is D, S, W, G, K, Q, A, E, L, M, H, Y, T, F, I, N, or R, $Z_6$ is S, D, A, R, T, K, N, M, P, H, W, Y, V, F, G, I, L, or Q, $Z_7$ is V, M, A, L, T, F, or I; $Z_8$ is K, N, Q, A, R, Y, T, W, I, F, V, G, H, S, L, E, D, or M; and $Z_9$ is G, H, N, T, F, R, K, Y, Q, S, D, P, or A; and
  - (iii) a HCDR3 consisting of the amino acid sequence of $GX_8DZ_{10}X_9RMX_{10}X_{11}$ (SEQ ID NO: 143), wherein $X_8$ is M, L, T, E, A, R, or Q, is $X_9$ is K, R, A, M, I, K, or V; $X_{10}$ is D, S, or E; $X_1$ is H, Y, F, N, R, K, W, or E; and $Z_{10}$ is A, D, E, or S; and
- (b) a light chain variable region (VL) comprising
  - (i) a light chain CDR1 (LCDR1) consisting of the amino acid sequence of $Z_{11}GZ_{12}X_{12}X_{13}NX_{14}X_{15}X_{16}GYVX_{17}Z_{13}$ (SEQ ID NO: 144), wherein $X_{12}$ is A, G, S, T, F, P, R, M, E, D, H, I, Y, W, L, V, N, Q, or K; $X_{13}$ is S, T, Y, D, A, E, Q, N, or H; $X_{14}$ is IL, M, or V; $X_{15}$ is G or H; $X_{16}$ is A, G, H, F, Y, Q, S, or M; $X_{17}$ is N, V, S, N, L, A, or T; Zu is T, I, R, G, F, S, K, D, A, L, W, H, M, V, Y, Q, or E; $Z_{12}$ is S, D, Q, Y, G, E, H, W, R, T, or A; and $Z_{13}$ is H or Q;

(ii) a LCDR2 consisting of the amino acid sequence of $RX_{18}X_{19}X_{20}X_{21}Z_{14}Z_{15}$, wherein $X_{18}$ is H, N, S, or T; $X_{19}$ is H, N, L, V, M, Q, E, K, I, W, A, Y, R, S, G, F, T, or D; $X_{20}$ is L, Q, V, H, F, I, K, W, A, Y, R, M, E, or N; and $X_{21}$ is K, R, I, L, P, W, Y, F, M, V, H, Q, N, or A; $Z_{14}$ is P, I, F, M, K, T, G, D, R, L, Y, Q, N, A, E, S, V, or H; and $Z_{15}$ is S, W, R, G, E, D, Q, Y, H, M, P, L, A, F, V, K, T, I, or N; and (iii) a LCDR3 consisting of the amino acid sequence of $Z_{16}X_{22}X_{23}DZ_{17}X_{24}X_{25}X_{26}X_{27}WZ_{18}$, wherein $X_{22}$ is A, S, T, or V; $X_{23}$ H or W; $X_{24}$ is E, H, R, S, M, F, W, L, A, Y, T, P, K, H, I, G, D, Q, V, or N; $X_{25}$ is H, L, R, S, V, I, D, L, Y, F, M, E, K, A, N, W, T, or Q; $X_{26}$ is H, M, N, Q, S, T, G, T, A, F, or E; $X_{27}$ is A, G, K, or S; $Z_{16}$ is A, T, or S; $Z_{17}$ is D or N; and $Z_{18}$ is L, M, I, F, G, A, or V;

In some embodiments, the anti-PRLR antibody comprises no more than 8 amino acid residue variations in the HCDR1, HCDR2, and HCDR3 collectively as compared with the HCDR1, HCDR2, and HCDR3 set forth in SEQ ID NOs: 2, 7, and 12. Alternatively, or in addition, the anti-PRLR antibody comprises no more than 8 amino acid residue variations in the LCDR1, LCDR2, and LCDR3 collectively as compared with the LCDR1, LCDR2, and LCDR3 set forth in SEQ ID NOs: 18, 29, and 34.

In some examples, the anti-PRLR antibody comprises no more than 5 amino acid residue variations in the HCDR1, HCDR2, and HCDR3 collectively as compared with the HCDR1, HCDR2, and HCDR3 set forth in SEQ ID NOs: 2, 7, and 12. Alternatively, or in addition, the anti-PRLR antibody comprises no more than 5 amino acid residue variations in the LCDR1, LCDR2, and LCDR3 collectively as compared with the LCDR1, LCDR2, and LCDR3 set forth in SEQ ID NOs: 18, 29, and 34.

In some examples, the VH of the anti-PRLR antibody comprises an amino acid sequence at least 70% identical to SEQ ID NO: 68. Alternatively, or in addition, the VL of the anti-PRLR antibody comprises an amino acid sequence at least 70% identical to SEQ ID NO: 83.

Any of the above-described anti-PRLR antibody may comprise any of the VH and VL framework regions as disclosed herein.

In some instances, the antibody is a full-length antibody, an antigen-binding fragment thereof, or a single chain variable fragment (scFv). In other instances, the antibody is a full-length antibody, which is an IgG molecule. In some examples, the antibody comprises a heavy chain comprising the VH and a heavy chain constant region of an IgG1 molecule and a light chain comprising the VL and a light chain constant region. In some examples, the heavy chain constant region is a wild-type IgG1 constant region. Alternatively, the heavy chain constant region is a variant of a wild-type IgG1, for example, those disclosed herein. In some specific examples, the heavy chain constant region comprises any one of sequences set forth in SEQ ID NOs: 97-98, and/or wherein the light chain constant region comprises any one of sequences set forth in SEQ ID NOs: 99-100.

In another aspect, the present disclosure provides a nucleic acid or a set of nucleic acids (i.e., two separate nucleic acid molecules) encoding any of the anti-PRLR antibodies disclosed herein. In some embodiments, the nucleic acid or the set of nucleic acids can be a vector or a set of vectors, for example, an expression vector(s).

Further, the present disclosure provides a host cell comprising the nucleic acid or the set of nucleic acids encoding the anti-PRLR antibody as disclosed herein.

Also provided herein is a method for making an antibody that binds prolactin receptor (PRLR), the method comprising: (a) culturing the host cell provided herein under conditions allowing for producing the antibody encoded by the nucleic acid(s) in the host cell; and (b) collecting the antibody thus produced.

In addition, the present disclosure provides a pharmaceutical composition, comprising any of the anti-PRLR antibodies disclosed herein, or their encoding nucleic acid(s), and a pharmaceutically acceptable carrier.

In yet another aspect, the present disclosure provides a method for modulating the cell signaling mediated by PRLR or for treating a disease associated with PRLR. Such a method comprises administering to a subject in need thereof an effective amount of the anti-PRLR antibody provided herein, the nucleic acid(s) encoding such, or the pharmaceutical composition comprising such. In some embodiments, the subject is a human patient having the disease associated with PRLR. Exemplary diseases associated with PRLR include cancer (e.g., gastrointestinal tumor, leukemias and other hematological malignancies; hormone-responsive cancers such as breast cancer, prostate cancer, ovarian, endometrial cancer, pituitary adenomas, or mammary hyperplasia); reproductive and gynecological disorders such as endometriosis and infertility; autoimmune and inflammatory disorder such as systemic lupus erythematosus and rheumatoid arthritis; dermatological conditions such as alopecia and psoriasis; metabolic disorders such as obesity and diabetes; hyperprolactinemia; or cardiovascular disease.

In some specific examples, the method as disclosed herein is for treating androgenetic alopecia or endometriosis in a subject in need of the treatment (e.g., a human patient having or suspected of having the disease) with any of the anti-PRLR antibodies disclosed herein. In some instances, antibody AB001, AB005, AB007, AB008, AB009, B012, or AB013 or a functional equivalent thereof (e.g., having the same heavy chain and light chain CDRs as those in any of the referenced anti-PRLR antibodies) can be used in such a treatment method.

Also provided herein is a method for restoring hair color in a subject comprising administering to a subject in need thereof an effective amount of an anti-PRLR antibody, for example, the anti-PRLR antibodies as disclosed herein.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 5A: is a graph illustrating the cumulative drug Stimulation Index (SI) across fourteen HLA-typed donors incubated with test candidate antibodies, clinical benchmark antibody, media only, the positive control protein KLH (keyhole limpet hemocyanin), or benchmark clinical mAbs (with low, middle, and high ADA rates). SI for treated conditions is normalized to that of the media-only control. Striations represent SI values from Individual donors. FIG. 5B: is a graph illustrating Donor T cell response distribution. Stimulation index (SI), a metric for normalized T cell response, was averaged across fourteen HLA-typed donors each incubated with test candidates, clinical benchmark antibody, media only, the positive control protein KLH (keyhole limpet hemocyanin), or benchmark clinical mAbs (with low, middle, and high ADA rates). Error bars represent max and min values.

FIG. 9A: Hair shaft production (μm). FIG. 9B: Macroscopic hair cycle staging. Data represents mean±SEM; n=107-136 hair follicles from 6 punches from 3 male donors.

FIG. 10A: Hair shaft production (μm). FIG. 10B: Macroscopic hair cycle staging. Data represents mean SEM; n=107-136 hair follicles from 6 punches from 3 male donors.

FIG. 13A: Proliferative cells. FIG. 13B: Apoptotic cells. Data represents mean±SEM; n=32-44 hair follicles from 3 male donors.

FIG. 15A: FGF-7 expression in ORS keratinocytes. FIG. 15B: IGF-1 expression in ORS keratinocytes. FIG. 15C: IGF-1 expression in hair matrix keratinocytes. FIG. 15D: TGFβ-2 expression in ORS keratinocytes. FIG. 15E: FGF7 expression in DP fibroblasts. FIG. 15F: IGF-1 expression in DP fibroblasts.

FIG. 16A: K85 expression. FIG. 16B: K14 expression in ORS keratinocytes. FIG. 16C: K15 expression in the bulge. FIG. 16D: Number of cells expressing K15 in the bulge. FIG. 16E: K15+ Caspase 3+ cells in the bulge. FIG. 16F: K15+Ki67+ cells in the bulge. FIG. 16G: CD34 expression in the proximal ORS keratinocytes. FIG. 16H: K85 expression anagen VI hair follicles. FIG. 16I: K31 expression anagen. FIG. 16J: K19 expression in ORS keratinocytes. FIG. 16K: CD200 expression in the bulge. FIG. 16L: % of CD200 positive cells in the bulge.

FIGS. 17C-17D are graphs showing the fold changes in the expression of CD31 in the dermal sheath (FIG. 17C) or the change in the number of CD31+ cells in the dermal sheath (FIG. 17D) of hair follicles from ex vivo cultured human male scalp skin treated as indicated and assessed six days post-treatment.

FIG. 18A: VEGFA expression in the outer root sheath (ORS) keratinocytes. FIG. 18B: VEGFA expression in the hair matrix keratinocytes. FIG. 18C: VEGFA expression in the fibroblasts in the dermal papilla (DP).

FIG. 19A: Number of PRLR+/STAT5 cells. FIG. 19B: Number of PRLR+/STAT5+/pSTAT5+ cells.

DETAILED DESCRIPTION

Figure 1:
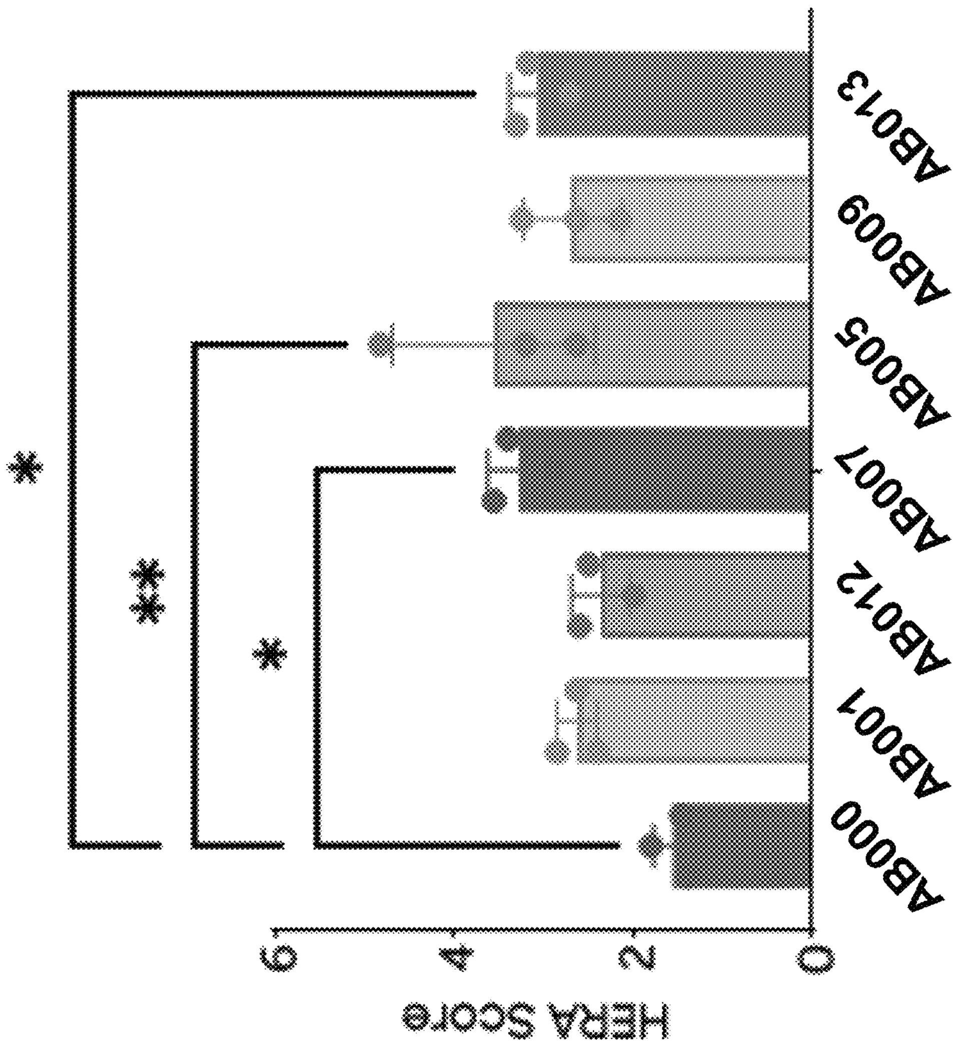
FIG. 1 is a graph illustrating Human Endothelial Cells Recycling Assay (HERA) scores of the test candidates and the clinical benchmark antibody.

The present disclosure describes polypeptide and therapeutics that include an anti-Prolactin Receptor Antibody capable of binding to an epitope, such as a Prolactin Receptor.

Prolactin is a hormone that is synthesized and secreted by lactotroph cells in the anterior pituitary gland. Prolactin signaling occurs via a unique transmembrane prolactin receptor (PRLR), which is expressed in various tissues. The structure of the PRLR is similar to that of many biologically fundamental receptors of the class 1 hematopoietic cytokine receptor family such as the growth hormone receptor and is characterized by two distinct extracellular domains (ECD), a transmembrane domain and an intracellular domain (ICD) each containing highly conserved motifs. PRL binding to PRLR induces downstream signaling, for example, through the JAK-STAT pathway. Bernard et al., *Nat Rev Endocrinol* 15(6):356-365 (2019); Secchi et al., *eLife* 12:e84645 (2023).

PRLR from various species are well known in the art. For example, the amino acid sequence of human PRLR can be found under GenBank accession no. NM_000949.7 (see also Gene ID: 5618). The prolactin receptor (PRLR) is implicated in a variety of conditions and diseases due to its role in hormonal signaling and its influence on cell proliferation, differentiation, and immune responses. These conditions and diseases include gastrointestinal tumor, leukemias and other hematological malignancies; hormone-responsive cancers such as breast cancer, prostate cancer, ovarian, and endometrial cancer; reproductive and gynecological disorders such as endometriosis and infertility; autoimmune and inflammatory disorder such as systemic lupus erythematosus and rheumatoid arthritis; dermatological conditions such as alopecia and psoriasis; metabolic disorders such as obesity and diabetes; pituitary adenomas, mammary hyperplasia; hyperprolactinemia; and cardiovascular disease.

Accordingly, the anti-prolactin receptor antibodies disclosed herein can be used for treating various diseases and conditions associated with prolactin receptor. In addition, the anti-prolactin receptor antibodies can also be used as diagnostic agents for detecting presence of prolactin receptor, including prolactin receptor positive cells.

The embodiments of the present disclosure are described in greater details below. The following descriptions and examples illustrate embodiments of the present disclosure in detail. Although the present disclosure has been described in some details by way of illustration and example for purposes of clarity and understanding, it will be apparent that certain changes and modifications can be practiced within the scope of the appended claims.

The section headings used herein are for organizational purposes only and are not to be construed as limiting the subject matter described.

Although various features of the disclosure can be described in the context of a single embodiment, the features can also be provided separately or in any suitable combination. Conversely, although the present disclosure can be described herein in the context of separate embodiments for clarity, the present disclosure can also be implemented in a single embodiment. It is to be understood that the present disclosure is not limited to the particular embodiments described herein and as such can vary. Those of skill in the art will recognize that there are variations and modifications of the present disclosure, which are encompassed within its scope.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the disclosure can be used in combination with any other unless specifically indicated otherwise.

I. Anti-Prolactin Receptor Antibodies and Compositions Comprising Such

In some aspects, the present disclosure provides anti-prolactin receptor antibodies derived from the parent clone AB000 via AI modeling to improve bioactivities and developability, which refers to the likelihood that a potential drug candidate would be save, effective, and manufacturable. Given the superior features of the anti-PRLR antibodies disclosed herein as compared with the parent clone, the anti-PRLR antibodies disclosed herein are expected to be safe and effective in modulating PRLR-mediated cell signaling, thereby benefiting treatment of diseases associated with PRLR.

A. Anti-Prolactin Receptor Antibodies

The present disclosure provides antibodies binding to prolactin receptor, for example, human prolactin receptor. In some embodiments, the anti-prolactin receptor antibodies disclosed herein are capable of binding to prolactin receptor expressed on cell surface (e.g., binding to prolactin receptor positive cells). As such, the antibodies disclosed herein can be used for either therapeutic or diagnostic purposes to target prolactin receptor-positive cells (e.g., cancer cells). As used herein, the term "anti-prolactin receptor antibody" refers to any antibody capable of binding to a prolactin receptor polypeptide (e.g., a prolactin receptor polypeptide expressed on cell surface), which can be of a suitable source, for example, human or a non-human mammal (e.g., mouse, rat, rabbit, primate such as monkey, etc.).

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody", e.g., anti-prolactin receptor antibody, encompasses not only intact (e.g., full-length) polyclonal or monoclonal antibodies, but also antigen-binding fragments thereof (such as Fab, Fab', F(ab')2, Fv), single-chain antibody (scFv), fusion proteins comprising an antibody portion, humanized antibodies, chimeric antibodies, diabodies, single domain antibody (e.g., nanobody), single domain antibodies (e.g., a $V_H$ only antibody), multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies (e.g., antibody-drug conjugates or ADCs). An antibody, e.g., anti-prolactin receptor antibody, includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

A typical antibody molecule comprises a heavy chain variable region (VH) and a light chain variable region ($V_L$), which are usually involved in antigen binding. The VH and $V_L$ regions can be further subdivided into regions of hypervariability, also known as "complementarity determining regions" ("CDR"), interspersed with regions that are more conserved, which are known as "framework regions" ("FR"). Each VH and $V_L$ is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the Chothia definition, the AbM definition, and/or the contact definition, all of which are well known in the art. See, e.g., Kabat, E. A., et al., *Sequences of Proteins of Immunological Interest, Fifth Edition*, U.S. (1991), Department of Health and Human Services, NIH Publication No. 91-3242; Chothia et al., *Nature* 342(6252):877 (1989); Chothia et al., (1987) *J. Mol. Biol.* 196(4):901-917; Al-lazikani et al., *J. Molec. Biol.* 273(4):927-948 (1997); and Almagro, J. Mol. Recognit. 17:132-143 (2004). See also hgmp.mrc.ac.uk and bioinf.org.uk/abs. Unless explicitly indicated herein, the CDR sequences disclosed herein are based on the Kabat definition.

The anti-prolactin receptor antibody described herein can be a full-length antibody, which contains two heavy chains and two light chains, each including a variable domain and a constant domain. Alternatively, the anti-prolactin receptor antibody can be an antigen-binding fragment of a full-length antibody. Examples of binding fragments encompassed within the term "antigen-binding fragment" of a full length antibody include (i) a Fab fragment, a monovalent fragment consisting of the $V_L$, $V_H$, $C_L$ and $C_H1$ domains; (ii) a $F(ab')_2$ fragment, a bivalent fragment including two Fab fragments linked by a disulfide bridge at the hinge region; (iii) a Fd fragment consisting of the $V_H$ and $C_Hi$ domains; (iv) a Fv fragment consisting of the VL and VH domains of a single arm of an antibody, (v) a dAb fragment (Ward et al., *Nature* 341:544-546 (1989)), which consists of a $V_H$ domain; and (vi) an isolated complementarity determining region (CDR) that retains functionality. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv). See e.g., Bird et al., Science 242(4877):423-426 (1988); and Huston et al., *Proc. Natl. Acad. Sci. USA* 85(16):5879-5883 (1988).

In some embodiments, the anti-prolactin receptor antibodies described herein specifically bind to the corresponding target antigen (e.g., prolactin receptor) or an epitope thereof. An antibody that "specifically binds" to an antigen or an epitope is a term well understood in the art. A molecule is said to exhibit "specific binding" if it reacts more frequently, more rapidly, with greater duration and/or with greater affinity with a particular target antigen than it does with alternative targets. An antibody "specifically binds" to a target antigen or epitope if it binds with greater affinity, avidity, more readily, and/or with greater duration than it binds to other substances. For example, an antibody that specifically (or preferentially) binds to an antigen (prolactin receptor) or an antigenic epitope therein is an antibody that binds this target antigen with greater affinity, avidity, more readily, and/or with greater duration than it binds to other antigens or other epitopes in the same antigen. It is also understood with this definition that, for example, an antibody that specifically binds to a first target antigen may or may not specifically or preferentially bind to a second target antigen. As such, "specific binding" or "preferential binding" does not necessarily require (although it can include) exclusive binding. In some examples, an antibody that "specifically binds" to a target antigen or an epitope thereof may not bind to other antigens or other epitopes in the same antigen (i.e., only baseline binding activity can be detected in a conventional method).

In some embodiments, an anti-prolactin receptor antibody as described herein has a suitable binding affinity for the target antigen (e.g., prolactin receptor) or antigenic epitopes thereof. Binding affinity refers to the apparent association constant or $K_A$. The $K_A$ is the reciprocal of the dissociation constant ($K_D$). The anti-prolactin receptor antibody described herein can have a binding affinity ($K_D$) of at least 20 nM, 10 nM, 1 nM, 0.1 nM, or lower for prolactin receptor. An increased binding affinity corresponds to a decreased $K_D$. Higher affinity binding of an antibody for a first antigen relative to a second antigen can be indicated by a higher $K_A$ (or a smaller numerical value $K_D$) for binding the first antigen than the $K_A$ (or numerical value $K_D$) for binding the second antigen. In such cases, the antibody has specificity for the first antigen (e.g., a first protein in a first conformation or mimic thereof) relative to the second antigen (e.g., the same first protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 90, 100, 500, 1000, 10,000 or $10^5$-fold. In some embodiments, any of the anti-prolactin receptor antibodies can be further affinity matured to increase the binding affinity of the antibody to the target antigen or antigenic epitope thereof.

Binding affinity (or binding specificity) can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) is generally related to the concentration of free target protein ([Free]) by the following equation:

$$[\text{Bound}] = [\text{Free}]/(Kd + [\text{Free}])$$

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

In some embodiments, the anti-prolactin receptor antibody disclosed herein has an $IC_{50}$ value of lower than 10 nM, e.g., <1 nM, <0.5 nM, or lower than 0.1 nM, for binding to prolactin receptor and/or prolactin receptor-positive cells. As used herein, $IC_{50}$ values refer to the minimum concentration of an antibody required to bind to 50% of the cells in a prolactin receptor-positive cell population. $IC_{50}$ values can be determined using conventional assays and/or assays disclosed herein. See, e.g., Examples below.

A number of exemplary anti-prolactin receptor antibodies are provided in Table 5 below.

In some embodiments, the anti-prolactin receptor antibodies described herein bind to the same epitope of a prolactin receptor polypeptide as any of the exemplary antibodies described herein (for example, AB001, AB002, AB007, and AB012) or compete against the exemplary antibody from binding to the prolactin receptor antigen. An epitope refers to the site on a target antigen that is recognized and bound by an antibody. The site can be entirely composed of amino acid components, entirely composed of chemical modifications of amino acids of the protein (e.g., glycosyl moieties), or composed of combinations thereof. Overlapping epitopes include at least one common amino acid residue. An epitope can be linear, which is typically 6-15 amino acids in length. Alternatively, the epitope can be conformational. The epitope to which an antibody binds can be determined by routine technology, for example, the epitope mapping method (see, e.g., descriptions below). An antibody that binds the same epitope as an exemplary antibody described herein can bind to exactly the same epitope or a substantially overlapping epitope (e.g., containing less than 3 non-overlapping amino acid residues, less than 2 non-overlapping amino acid residues, or only 1 non-overlapping amino acid residue) as the exemplary antibody. Whether two antibodies compete against each other from binding to the cognate antigen can be determined by a competition assay, which is well known in the art.

In some examples, the anti-prolactin receptor antibody comprises the same $V_H$ and/or $V_L$ CDRs as an exemplary antibody described herein. See Tables 1 and 2. Two antibodies having the same $V_H$ and/or $V_L$ CDRs means that their CDRs are identical when determined by the same approach (e.g., the Kabat approach, the Chothia approach, the AbM approach, the Contact approach, or the IMGT approach as known in the art. See, e.g., bioinf.org.uk/abs/). Such anti-prolactin receptor antibodies can have the same $V_H$, the same $V_L$, or both as compared to an exemplary antibody described herein.

Also within the scope of the present disclosure are functional variants of any of the exemplary anti-prolactin receptor antibodies as disclosed herein. Such functional variants are substantially similar to the exemplary antibody, both structurally and functionally. A functional variant comprises substantially the same $V_H$ and $V_L$ CDRs as the exemplary antibody. For example, it can comprise only up to 8 (e.g., 8, 7, 6, 5, 4, 3, 2, or 1) amino acid residue variations in the total CDR regions of the antibody and binds the same epitope of prolactin receptor with substantially similar affinity (e.g., having a $K_D$ value in the same order). In some instances, the functional variants can have the same heavy chain CDR3 as the exemplary antibody, and optionally the same light chain CDR3 as the exemplary antibody. Alternatively, or in addition, the functional variants can have the same heavy chain CDR2 as the exemplary antibody. Such an anti-prolactin receptor antibody can comprise a $V_H$ fragment having CDR amino acid residue variations in only the heavy chain CDR1 as compared with the VH of the exemplary antibody. In some examples, the anti-prolactin receptor antibody can further comprise a $V_L$ fragment having the same $V_L$ CDR3, and optionally same $V_L$ CDR1 or VL $CDR_2$ as the exemplary antibody.

Alternatively, or in addition, the amino acid residue variations can be conservative amino acid residue substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g., Molecular Cloning: A Laboratory Manual, J. Sambrook, et al., eds., Second Edition, Cold Spring Harbor Laboratory Press, Cold Spring Harbor, New York, (1989), or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the anti-prolactin receptor antibody can comprise heavy chain CDRs that are at least 80% (e.g., 85%, 90%, 95%, or 98%) sequence identity, individually or collectively, as compared with the $V_H$ CDRs of an exemplary antibody described herein. Alternatively, or in addition, the anti-prolactin receptor antibody can comprise light chain CDRs that are at least 80% (e.g., 85%, 90%, 95%, or 98%) sequence identity, individually or collectively, as compared with the $V_L$ CDRs as an exemplary antibody described herein. As used herein, "individually" means that one CDR of an antibody shares the indicated sequence identity relative to the corresponding CDR of the exemplary antibody. "Collectively" means that three $V_H$ or $V_L$ CDRs of an antibody in combination share the indicated sequence identity relative the corresponding three $V_H$ or $V_L$ CDRs of the exemplary antibody in combination.

The "percent identity" of two amino acid sequences is determined using the algorithm of Karlin and Altschul *Proc. Natl. Acad. Sci. USA* 87(6):2264-68 (1990), modified as in Karlin and Altschul *Proc. Natl. Acad. Sci. USA* 90(12):5873-77 (1993). Such an algorithm is incorporated into the NBLAST and XBLAST programs (version 2.0) of Altschul, et al., *J. Mol. Biol.* 215:403-10 (1990). BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., *Nucleic Acids Res.* 25(17):3389-3402 (1997). When utilizing BLAST and Gapped BLAST programs, the default parameters of the respective programs (e.g., XBLAST and NBLAST) can be used.

In some embodiments, the anti-prolactin receptor antibody disclosed herein can be a single chain antibody (scFv). A scFv antibody can comprise a $V_H$ fragment and a $V_L$ fragment, which can be linked via a flexible peptide linker. In some instances, the scFv antibody can be in the $V_H \rightarrow V_L$ orientation (from N-terminus to C-terminus). In other instances, the scFv antibody can be in the $V_L \rightarrow V_H$ orientation (from N-terminus to C-terminus). Exemplary anti-prolactin receptor scFv antibodies include those having the $V_H/V_L$ pair of any of the exemplary anti-prolactin receptor antibodies listed in Table 5.

Any of the anti-prolactin receptor antibody as described herein, e.g., the exemplary anti-prolactin receptor antibodies provided here, can bind and inhibit (e.g., reduce or eliminate) the activity of prolactin receptor-positive cells (e.g., B cells). In some embodiments, the anti-prolactin receptor antibody as described herein can bind and inhibit the activity of prolactin receptor-positive cells by at least 30% (e.g., 35%, 40%, 45%, 50%, 60%, 70%, 80%, 90%, 95% or greater, including any increment therein). The inhibitory activity of an anti-prolactin receptor antibody described herein can be determined by routine methods known in the art, e.g., by an assay for measuring the $K_{i,}^{app}$ value.

In some examples, the $K_{i,}^{app}$ value of an antibody can be determined by measuring the inhibitory effect of different concentrations of the antibody on the extent of a relevant reaction; fitting the change in pseudo-first order rate constant (v) as a function of inhibitor concentration to the modified Morrison equation (Equation 1) yields an estimate of the apparent Ki value. For a competitive inhibitor, the $Ki^{app}$ can be obtained from the y-intercept extracted from a linear regression analysis of a plot of $K_{i,}^{app}$ versus substrate concentration.

$$v = A \cdot \frac{([E] - [I] - K_i^{app}) + \sqrt{([E] - [I] - K_i^{app})^2 + 4[E] \cdot K_i^{app}}}{2} \quad \text{(Equation 1)}$$

where A is equivalent to $v_o/E$, the initial velocity ($v_o$) of the enzymatic reaction in the absence of inhibitor (I) divided by the total enzyme concentration (E). In some embodiments, the anti-prolactin receptor antibody described herein can have a $Ki^{app}$ value of 1000, 500, 100, 50, 40, 30, 20, 10, 5 pM or less for the target antigen or antigen epitope.

(i) CDR Regions

The anti-PRLR antibodies provided herein (e.g., in Fab format) can comprise a heavy chain that comprises a heavy chain variable region (VH) and a light chain that comprises a light chain variable region (VL), each of which comprise three complementarity determining regions (CDRs), CDR1, CDR2, and CDR3. Provided herein are anti-prolactin receptor antibodies comprising a heavy chain variable region comprising a HCDR1 set forth as by a consensus motif of $X_1X_2WX_3H$, wherein $X_1$ is D or S; $X_2$ is F, H, or Y; and $X_3$ is M or L, a HCDR2 set forth as $DISRX_4X_5PYX_6X_7YADSVKG$ (SEQ ID NO: 131), wherein $X_4$ is I or L; $X_5$ is K or S; $X_6$ is H or T; and $X_7$ is G or N, a HCDR3 set forth as $GX_8DAX_9RMX_{10}X_{11}$ (SEQ ID NO: 132), wherein $X_8$ is M or L, is $X_9$ is K or R; $X_{10}$ is D or S; and $X_{11}$ is H or Y, and a light chain variable region comprising a LCDR1 set forth as by a consensus motif of $TGSX_{12}X_{13}NX_{14}X_{15}X_{16}GYVX_{17}H$ (SEQ ID NO: 133), wherein $X_{12}$ is A, G, S, T; $X_{13}$ is S or T; $X_{14}$ is I or L; $X_{15}$ is G or H; $X_{16}$ is A, G, or H; and $X_{17}$ is N or V, a LCDR2 set forth as $RX_{18}X_{19}X_{20}X_{21}PS$, wherein $X_{18}$ is H or N; $X_{19}$ is H or N; $X_{20}$ is L, Q, V; and $X_{21}$ is K or R and a LCDR3 set forth as $AX_{22}X_{23}DDX_{24}X_{25}X_{26}X_{27}WL$ (SEQ ID NO: 134), wherein $X_{22}$ is A or S; $X_{23}$ H or W; $X_{24}$ is E, H, R, or S; $X_{25}$ is H, L, R, S, or V; $X_{26}$ is H, M, N, Q, S, T; and $X_{27}$ is A or G (see Tables 1 and 2).

In some instances, the anti-PRLR antibody can contain a heavy chain CDR1 of SYWMH (SEQ ID NO: 1), wherein $X_1$ is S, $X_2$ is Y, $X_3$ is M, a heavy chain CDR2 of DIARLSSYTNYADSVKG (SEQ ID NO: 6), wherein $X_4$ is L; $X_5$ is S; $X_6$ is T; and $X_7$ is N, a heavy chain CDR3 of GLDARRMDY (SEQ ID NO: 12), wherein $X_8$ is L, is $X_9$ is R; $X_{10}$ is D; and $X_{11}$ is Y, and a light chain CDR1 of TGSSSNIGAGYVVH (SEQ ID NO: 17), wherein $X_{12}$ is S; $X_{13}$ is S; $X_{14}$ is I; $X_{15}$ is G; $X_{16}$ is A, a light chain CDR2 of RNNQRPS (SEQ ID NO: 28), wherein $X_{18}$ is N; $X_{19}$ is N; $X_{20}$ is Q; and $X_{21}$ is R, and a light chain CDR3 of AAWDDSLNGWL (SEQ ID NO: 33), wherein $X_{22}$ is A; $X_{23}$ is W; $X_{24}$ is S; $X_{25}$ is L; $X_{26}$ is N; and $X_{27}$ is G.

In some instances, the anti-PRLR antibody contains a heavy chain CDR1 of DYWMH (SEQ ID NO: 2), wherein $X_1$ is D, $X_2$ is Y, $X_3$ is M, a heavy chain CDR2 of DISRLKPYTNYADSVKG (SEQ ID NO: 7), wherein $X_4$ is L; $X_5$ is K; $X_6$ is T; and $X_7$ is N, a heavy chain CDR3 of GLDARRMDY (SEQ ID NO: 12), wherein $X_8$ is L, is $X_9$ is R; $X_{10}$ is D; and $X_{11}$ is Y, and a light chain CDR1 of TGSGTNIGAGYVVH (SEQ ID NO: 18), wherein $X_{12}$ is G; $X_{13}$ is T; $X_{14}$ is I; $X_{15}$ is G; $X_{16}$ is A, a light chain CDR2 of RNNLRPS (SEQ ID NO: 29), wherein $X_{18}$ is N; $X_{19}$ is N; $X_{20}$ is L; and $X_{21}$ is R, and a light chain CDR3 of ASWDDRHQAWL (SEQ ID NO: 34), wherein $X_{22}$ is S; $X_{23}$ is W; $X_{24}$ is R; $X_{25}$ is H; $X_{26}$ is Q; and $X_{27}$ is A.

In some instances, the anti-PRLR antibody contains a heavy chain CDR1 of SYWMH (SEQ ID NO: 1), wherein $X_1$ is S, $X_2$ is Y, $X_3$ is M, a heavy chain CDR2 of DISRLSPYTGYADSVKG (SEQ ID NO: 8), wherein $X_4$ is L; $X_5$ is S; $X_6$ is T; and $X_7$ is G, a heavy chain CDR3 of GMDAKRMDH (SEQ ID NO: 13), wherein $X_8$ is M, is $X_9$ is K; $X_{10}$ is D; and $X_{11}$ is H, and a light chain CDR1 of TGSSSNIGAGYVVH (SEQ ID NO: 17), wherein $X_{12}$ is S; $X_{13}$ is S; $X_{14}$ is I; $X_{15}$ is G; $X_{16}$ is A, a light chain CDR2 of RNNLRPS (SEQ ID NO: 29), wherein $X_{18}$ is N; $X_{19}$ is N; $X_{20}$ is L; and $X_{21}$ is R, and a light chain CDR3 of ASWDDSLQAWL (SEQ ID NO: 35), wherein $X_{22}$ is S; $X_{23}$ is W; $X_{24}$ is S; $X_{25}$ is L; $X_{26}$ is Q; and $X_{27}$ is A.

In some instances, the anti-PRLR antibody contains a heavy chain CDR1 of DFWMH (SEQ ID NO: 3), wherein $X_1$ is D, $X_2$ is F, $X_3$ is M, a heavy chain CDR2 of DISRLSPYTNYADSVKG (SEQ ID NO: 9), wherein $X_4$ is L; $X_5$ is S; $X_6$ is T; and $X_7$ is N, a heavy chain CDR3 of GLDARRMDY (SEQ ID NO: 12), wherein $X_8$ is L, is $X_9$ is R; $X_{10}$ is D; and $X_{11}$ is Y, and a light chain CDR1 of TGSSSNLGAGYVNH (SEQ ID NO: 19), wherein $X_{12}$ is S; $X_{13}$ is S; $X_{14}$ is L; $X_{15}$ is G; $X_{16}$ is A, a light chain CDR2 of RNNQRPS (SEQ ID NO: 28), wherein $X_{18}$ is N; $X_{19}$ is N; $X_{20}$ is Q; and $X_{21}$ is R, and a light chain CDR3 of ASWDDHSSAWL (SEQ ID NO: 36), wherein $X_{22}$ is S; $X_{23}$ is W; $X_{24}$ is H; $X_{25}$ is S; $X_{26}$ is S; and $X_{27}$ is A.

In some instances, the anti-PRLR antibody contains a heavy chain CDR1 of SYWMH (SEQ ID NO: 1), wherein $X_1$ is S, $X_2$ is Y, $X_3$ is M, a heavy chain CDR2 of DISRISPYTNYADSVKG (SEQ ID NO: 10), wherein $X_4$ is I; $X_5$ is S; $X_6$ is T; and $X_7$ is N, a heavy chain CDR3 of GLDARRMDY (SEQ ID NO: 12), wherein $X_8$ is L, is $X_9$ is R; $X_{10}$ is D; and $X_{11}$ is Y, and a light chain CDR1 of TGSSTNLGAGYVVH (SEQ ID NO: 20), wherein $X_{12}$ is S; $X_{13}$ is T; $X_{14}$ is L; $X_{15}$ is G; $X_{16}$ is A, a light chain CDR2 of RNNQRPS (SEQ ID NO: 28), wherein $X_{18}$ is N; $X_{19}$ is N; $X_{20}$ is Q; and $X_{21}$ is R, and a light chain CDR3 of AAWDDSVSGWL (SEQ ID NO: 37), wherein $X_{22}$ is A; $X_{23}$ is W; $X_{24}$ is S; $X_{25}$ is V; $X_{26}$ is S; and $X_{27}$ is G.

In some instances, the anti-PRLR antibody contains a heavy chain CDR1 of DYWMH (SEQ ID NO: 2), wherein $X_1$ is D, $X_2$ is Y, $X_3$ is M, a heavy chain CDR2 of DISRLSPYTGYADSVKG (SEQ ID NO: 8), wherein $X_4$ is L; $X_5$ is S; $X_6$ is T; and $X_7$ is G, a heavy chain CDR3 of GLDARRMDY (SEQ ID NO: 12), wherein $X_8$ is L, is $X_9$ is R; $X_{10}$ is D; and $X_{11}$ is Y, and a light chain CDR1 of TGSSSNLGGGYVVH (SEQ ID NO: 21), wherein $X_{12}$ is S; $X_{13}$ is S; $X_{14}$ is L; $X_{15}$ is G; $X_{16}$ is G, a light chain CDR2 of RNNQRPS (SEQ ID NO: 28), wherein $X_{18}$ is N; $X_{19}$ is N; $X_{20}$ is Q; and $X_{21}$ is R, and a light chain CDR3 of ASWDDSLQGWL (SEQ ID NO: 38), wherein $X_{22}$ is S; $X_{23}$ is W; $X_{24}$ is S; $X_{25}$ is L; $X_{26}$ is Q; and $X_{27}$ is G.

In some instances, the anti-PRLR antibody contains a heavy chain CDR1 of DYWMH (SEQ ID NO: 2), wherein $X_1$ is D, $X_2$ is Y, $X_3$ is M, a heavy chain CDR2 of DISRLSPYTNYADSVKG (SEQ ID NO: 9), wherein $X_4$ is L; $X_5$ is S; $X_6$ is T; and $X_7$ is N, a heavy chain CDR3 of GLDARRMSY (SEQ ID NO: 14), wherein $X_8$ is L, is $X_9$ is R; $X_{10}$ is S; and $X_{11}$ is Y, and a light chain CDR1 of TGSASNIGAGYVVH (SEQ ID NO: 22), wherein $X_{12}$ is A; $X_{13}$ is S; $X_{14}$ is I; $X_{15}$ is G; $X_{16}$ is A, a light chain CDR2 of RNNVRPS (SEQ ID NO: 30), wherein $X_{18}$ is N; $X_{19}$ is N; $X_{20}$ is V; and $X_{21}$ is R, and a light chain CDR3 of AAWDDHRTAWL (SEQ ID NO: 39), wherein $X_{22}$ is A; $X_{23}$ is W; $X_{24}$ is H; $X_{25}$ is R; $X_{26}$ is T; and $X_{27}$ is A.

In some instances, the anti-PRLR antibody contains a heavy chain CDR1 of DYWMH (SEQ ID NO: 2), wherein $X_1$ is D, $X_2$ is Y, $X_3$ is M, a heavy chain CDR2 of DISRLSPYTNYADSVKG (SEQ ID NO: 9), wherein $X_4$ is L; $X_5$ is S; $X_6$ is T; and $X_7$ is N, a heavy chain CDR3 of GLDARRMSY (SEQ ID NO: 14), wherein $X_8$ is L, is $X_9$ is R; $X_{10}$ is S; and $X_{11}$ is Y, and a light chain CDR1 of TGSSSNIGHGYVVH (SEQ ID NO: 23), wherein $X_{12}$ is S; $X_{13}$ is S; $X_{14}$ is I; $X_{15}$ is G; $X_{16}$ is H, a light chain CDR2 of RNNQRPS (SEQ ID NO: 28), wherein $X_{18}$ is N; $X_{19}$ is N; $X_{20}$ is Q; and $X_{21}$ is R, and a light chain CDR3 of AAWDDSLNGWL (SEQ ID NO: 33), wherein $X_{22}$ is A; $X_{23}$ is W; $X_{24}$ is S; $X_{25}$ is L; $X_{26}$ is N; and $X_{27}$ is G.

In some instances, the anti-PRLR antibody contains a heavy chain CDR1 of SYWLH (SEQ ID NO: 4), wherein $X_1$ is S, $X_2$ is Y, $X_3$ is L, a heavy chain CDR2 of DISRLSPYTNYADSVKG (SEQ ID NO: 9), wherein $X_4$ is L; $X_5$ is S; $X_6$ is T; and $X_7$ is N, a heavy chain CDR3 of GMDARRMDY (SEQ ID NO: 15), wherein $X_8$ is M, is $X_9$ is R; $X_{10}$ is D; and $X_{11}$ is Y, and a light chain CDR1 of TGSSSNLGAGYVVH (SEQ ID NO: 24), wherein $X_{12}$ is S; $X_{13}$ is S; $X_{14}$ is L; $X_{15}$ is G; $X_{16}$ is A, a light chain CDR2 of RNNQRPS (SEQ ID NO: 28), wherein $X_{18}$ is N; $X_{19}$ is N; $X_{20}$ is Q; and $X_{21}$ is R, and a light chain CDR3 of ASWDDSHMAWL (SEQ ID NO: 40), wherein $X_{22}$ is S; $X_{23}$ is W; $X_{24}$ is S; $X_{25}$ is H; $X_{26}$ is M; and $X_{27}$ is A.

In some instances, the anti-PRLR antibody contains a heavy chain CDR1 of SYWLH (SEQ ID NO: 4), wherein $X_1$ is S, $X_2$ is Y, $X_3$ is L, a heavy chain CDR2 of DISRLSPYTNYADSVKG (SEQ ID NO: 9), wherein $X_4$ is L; $X_5$ is S; $X_6$ is T; and $X_7$ is N, a heavy chain CDR3 of GMDARRMDY (SEQ ID NO: 15), wherein $X_8$ is M, is $X_9$ is R; $X_{10}$ is D; and $X_{11}$ is Y, and a light chain CDR1 of TGSTSNLGAGYVVH (SEQ ID NO: 25), wherein $X_{12}$ is T; $X_{13}$ is S; $X_{14}$ is L; $X_{15}$ is G; $X_{16}$ is A, a light chain CDR2 of RHHQRPS (SEQ ID NO: 31), wherein $X_{18}$ is H; $X_{19}$ is H; $X_{20}$ is Q; and $X_{21}$ is R, and a light chain CDR3 of ASWDDSHMAWL (SEQ ID NO: 40), wherein $X_{22}$ is S; $X_{23}$ is W; $X_{24}$ is S; $X_{25}$ is H; $X_{26}$ is M; and $X_{27}$ is A.

In some instances, the anti-PRLR antibody contains a heavy chain CDR1 of SHWLH (SEQ ID NO: 5), wherein $X_1$ is S, $X_2$ is H, $X_3$ is L, a heavy chain CDR2 of DISRLSPYTNYADSVKG (SEQ ID NO: 9), wherein $X_4$ is L; $X_5$ is S; $X_6$ is T; and $X_7$ is N, a heavy chain CDR3 of GLDARRMDH (SEQ ID NO: 16), wherein $X_8$ is L, is $X_9$ is R; $X_{10}$ is D; and $X_{11}$ is H, and a light chain CDR1 of TGSSSNLGAGYVVH (SEQ ID NO: 24), wherein $X_{12}$ is S; $X_{13}$ is S; $X_{14}$ is L; $X_{15}$ is G; $X_{16}$ is A, a light chain CDR2 of RHHQKPS (SEQ ID NO: 32), wherein $X_{18}$ is H; $X_{19}$ is H; $X_{20}$ is Q; and $X_{21}$ is K, and a light chain CDR3 of ASWDDSHMAWL (SEQ ID NO: 40), wherein $X_{22}$ is S; $X_{23}$ is W; $X_{24}$ is S; $X_{25}$ is H; $X_{26}$ is M; and $X_{27}$ is A.

In some instances, the anti-PRLR antibody contains a heavy chain CDR1 of SYWMH (SEQ ID NO: 1), wherein $X_1$ is S, $X_2$ is Y, $X_3$ is M, a heavy chain CDR2 of DISRLSPYHNYADSVKG (SEQ ID NO: 11), wherein $X_4$ is L; $X_5$ is S; $X_6$ is H; and $X_7$ is N, a heavy chain CDR3 of GLDARRMDY (SEQ ID NO: 12), wherein $X_8$ is L, is $X_9$ is R; $X_{10}$ is D; and $X_{11}$ is Y, and a light chain CDR1 of TGSSTNLGAGYVVH (SEQ ID NO: 20), wherein $X_{12}$ is S; $X_{13}$ is T; $X_{14}$ is L; $X_{15}$ is G; $X_{16}$ is A, a light chain CDR2 of RHHQRPS (SEQ ID NO: 31), wherein $X_{18}$ is H; $X_{19}$ is H; $X_{20}$ is Q; and $X_{21}$ is R, and a light chain CDR3 of ASWDDSHMAWL (SEQ ID NO: 40), wherein $X_{22}$ is S; $X_{23}$ is W; $X_{24}$ is S; $X_{25}$ is H; $X_{26}$ is M; and $X_{27}$ is A.

In some instances, the anti-PRLR antibody contains a heavy chain CDR1 of SYWLH (SEQ ID NO: 4), wherein $X_1$ is S, $X_2$ is Y, $X_3$ is L, a heavy chain CDR2 of DISRLSPYTNYADSVKG (SEQ ID NO: 9), wherein $X_4$ is L; $X_5$ is S; $X_6$ is T; and $X_7$ is N, a heavy chain CDR3 of GMDARRMDY (SEQ ID NO: 15), wherein $X_8$ is M, is $X_9$ is R; $X_{10}$ is D; and $X_{11}$ is Y, and a light chain CDR1 of TGSSSNIGGGYVVH (SEQ ID NO: 26), wherein $X_{12}$ is S; $X_{13}$ is S; $X_{14}$ is I; $X_{15}$ is G; $X_{16}$ is G, a light chain CDR2 of RNNQRPS (SEQ ID NO: 28), wherein $X_{18}$ is N; $X_{19}$ is N; $X_{20}$ is Q; and $X_{21}$ is R, and a light chain CDR3 of AAWDDERNGWL (SEQ ID NO: 41), wherein $X_{22}$ is A; $X_{23}$ is W; $X_{24}$ is E; $X_{25}$ is R; $X_{26}$ is N; and $X_{27}$ is G.

In some instances, the anti-PRLR antibody contains a heavy chain CDR1 of DYWMH (SEQ ID NO: 2), wherein $X_1$ is D, $X_2$ is Y, $X_3$ is M, a heavy chain CDR2 of DISRLSPYTNYADSVKG (SEQ ID NO: 9), wherein $X_4$ is L; $X_5$ is S; $X_6$ is T; and $X_7$ is N, a heavy chain CDR3 of GLDARRMSY (SEQ ID NO: 14), wherein $X_8$ is L, is $X_9$ is R; $X_{10}$ is S; and $X_{11}$ is Y, and a light chain CDR1 of TGSSSNIGAGYVVH (SEQ ID NO: 17), wherein $X_{12}$ is S; $X_{13}$ is S; $X_{14}$ is I; $X_{15}$ is G; $X_{16}$ is A, a light chain CDR2 of RNNQRPS (SEQ ID NO: 28), wherein $X_{18}$ is N; $X_{19}$ is N; $X_{20}$ is Q; and $X_{21}$ is R, and a light chain CDR3 of AAHDDELHGWL (SEQ ID NO: 42), wherein $X_{22}$ is A; $X_{23}$ is H; $X_{24}$ is E; $X_{25}$ is L; $X_{26}$ is H; and $X_{27}$ is G.

In some instances, the anti-PRLR antibody contains a heavy chain CDR1 of SYWLH (SEQ ID NO: 4), wherein $X_1$ is E, $X_2$ is Y, $X_3$ is L, a heavy chain CDR2 of DISRLSPYTNYADSVKG (SEQ ID NO: 9), wherein $X_4$ is L; $X_5$ is G; $X_6$ is T; and $X_7$ is N, a heavy chain CDR3 of GMDARRMDY (SEQ ID NO: 15), wherein $X_8$ is M, is $X_9$ is R; $X_{10}$ is D; and $X_{11}$ is Y, and a light chain CDR1 of TGSSSNIHGGYVVH (SEQ ID NO: 27), wherein $X_{12}$ is S; $X_{13}$ is S; $X_{14}$ is I; $X_{15}$ is H; $X_{16}$ is G, a light chain CDR2 of RNNQRPS (SEQ ID NO: 28), wherein $X_{18}$ is N; $X_{19}$ is N; $X_{20}$ is Q; and $X_{21}$ is R, and a light chain CDR3 of AAWDDSRNGWL (SEQ ID NO: 43), wherein $X_{22}$ is A; $X_{23}$ is W; $X_{24}$ is 5; $X_{25}$ is R; $X_{26}$ is N; and $X_{27}$ is G.

TABLE 1

Heavy Chain Complementarity Determining Regions (CDRs)

| | HCDR1 | | HCDR2 | | HCDR3 | |
|---|---|---|---|---|---|---|
| Clone Name | Sequences | SEQ ID NO | Sequences | SEQ ID NO | Sequences | SEQ ID NO |
| AB000 | SYWMH | 1 | DIARLSSYTNYADSVKG | 6 | GLDARRMDY | 12 |
| AB001 | DYWMH | 2 | DISRLKPYTNYADSVKG | 7 | GLDARRMDY | 12 |
| AB002 | SYWMH | 1 | DISRLSPYTGYADSVKG | 8 | GMDAKRMDH | 13 |
| AB003 | DFWMH | 3 | DISRLSPYTNYADSVKG | 9 | GLDARRMDY | 12 |
| AB004 | SYWMH | 1 | DISRISPYTNYADSVKG | 10 | GLDARRMDY | 12 |
| AB005 | DYWMH | 2 | DISRLSPYTGYADSVKG | 8 | GLDARRMDY | 12 |
| AB006 | DYWMH | 2 | DISRLSPYTNYADSVKG | 9 | GLDARRMSY | 14 |
| AB007 | DYWMH | 2 | DISRLSPYTNYADSVKG | 9 | GLDARRMSY | 14 |
| AB008 | SYWLH | 4 | DISRLSPYTNYADSVKG | 9 | GMDARRMDY | 15 |
| AB009 | SYWLH | 4 | DISRLSPYTNYADSVKG | 9 | GMDARRMDY | 15 |
| AB010 | SHWLH | 5 | DISRLSPYTNYADSVKG | 9 | GLDARRMDH | 16 |
| AB011 | SYWMH | 1 | DISRLSPYHNYADSVKG | 11 | GLDARRMDY | 12 |
| AB012 | SYWLH | 4 | DISRLSPYTNYADSVKG | 9 | GMDARRMDY | 15 |
| AB013 | DYWMH | 2 | DISRLSPYTNYADSVKG | 9 | GLDARRMSY | 14 |
| AB014 | SYWLH | 4 | DISRLSPYTNYADSVKG | 9 | GMDARRMDY | 15 |
| Consensus Motifs | (a) $X_1X_2WX_3H$, wherein $X_1$ is D or S; $X_2$ is F, H, or Y; and $X_3$ is M or L (b) $X_1YWX_3H$, wherein $X_1$ is D or S; and $X_3$ is M or L | | (a) $DISRX_4X_5PYX_6X_7YADSVKG$ (SEQ ID NO: 131), wherein $X_4$ is I or L; $X_5$ is K or S; $X_6$ is H or T; and $X_7$ is G or N (b) $DISRLX_5PYTX_7YADSVKG$ (SEQ ID NO: 74), wherein $X_5$ is K or S; and $X_7$ is G or N (c) $DISRLX_5PYTNYADSVKG$ (SEQ ID NO: 76), wherein $X_5$ is K or S. | | (a) $GX_8DAX_9RMX_{10}X_{11}$ (SEQ ID NO: 132), wherein $X_8$ is M or L, $X_9$ is K or R; $X_{10}$ is D or S; and $X_{11}$ is H or Y (b) $GX_8DARRMX_{10}Y$ (SEQ ID NO: 139), wherein $X_8$ is M or L; and $X_{10}$ is D or S | |

TABLE 2

Light Chain Complementarity Determining Regions (CDRs)

| | LCDR1 | | LCDR2 | | LCDR3 | |
|---|---|---|---|---|---|---|
| Clone Name | Sequences | SEQ ID NO | Sequences | SEQ ID NO | Sequences | SEQ ID NO |
| AB000 | TGSSSNIGAGYVVH | 17 | RNNQRPS | 28 | AAWDDSLNGWL | 33 |
| AB001 | TGSGTNIGAGYVVH | 18 | RNNLRPS | 29 | ASWDDRHQAWL | 34 |
| AB002 | TGSSSNIGAGYVVH | 17 | RNNLRPS | 29 | ASWDDSLQAWL | 35 |
| AB003 | TGSSSNLGAGYVNH | 19 | RNNQRPS | 28 | ASWDDHSSAWL | 36 |
| AB004 | TGSSTNLGAGYVVH | 20 | RNNQRPS | 28 | AAWDDSVSGWL | 37 |
| AB005 | TGSSSNLGGGYVVH | 21 | RNNQRPS | 28 | ASWDDSLQGWL | 38 |
| AB006 | TGSASNIGAGYVVH | 22 | RNNVRPS | 30 | AAWDDHRTAWL | 39 |
| AB007 | TGSSSNIGHGYVVH | 23 | RNNQRPS | 28 | AAWDDSLNGWL | 33 |
| AB008 | TGSSSNLGAGYVVH | 24 | RNNQRPS | 28 | ASWDDSHMAWL | 40 |

TABLE 2-continued

Light Chain Complementarity Determining Regions (CDRs)

| | LCDR1 | | LCDR2 | | LCDR3 | |
|---|---|---|---|---|---|---|
| Clone Name | Sequences | SEQ ID NO | Sequences | SEQ ID NO | Sequences | SEQ ID NO |
| AB009 | TGSTSNLGAGYVVH | 25 | RHHQRPS | 31 | ASWDDSHMAWL | 40 |
| AB010 | TGSSSNLGAGYVVH | 24 | RHHQKPS | 32 | ASWDDSHMAWL | 40 |
| AB011 | TGSSTNLGAGYVVH | 20 | RHHQRPS | 31 | ASWDDSHMAWL | 40 |
| AB012 | TGSSSNIGGGYVVH | 26 | RNNQRPS | 28 | AAWDDERNGWL | 41 |
| AB013 | TGSSSNIGAGYVVH | 17 | RNNQRPS | 28 | AAHDDELHGWL | 42 |
| AB014 | TGSSSNIHGGYVVH | 27 | RNNQRPS | 28 | AAWDDSRNGWL | 43 |
| Consensus Motifs | (a) TGS$X_{12}X_{13}$N$X_{14}$ $X_{15}X_{16}$GYV$X_{17}$H (SEQ ID NO: 133), wherein $X_{12}$ is A, G, S, T; $X_{13}$ is S or T; $X_{14}$ is I or L; $X_{15}$ is Gor H; $X_{16}$ is A, G, or H; and $X_{17}$ is N or V. (b) TGS$X_{12}X_{13}$N$X_{14}$ $X_{15}X_{16}$GYVVH (SEQ ID NO: 108), wherein $X_{12}$ is G, S, T; $X_{13}$ is S or T; $X_{14}$ is I or L; $X_{15}$ is G or H; and $X_{16}$ is A, G, or H. (c) TGS$X_{12}X_{13}$NIG$X_{16}$GYV | | (a) R$X_{18}X_{19}X_{20}X_{21}$PS, wherein $X_{18}$ is H or N; $X_{19}$ is H or N; $X_{20}$ is L, Q, V; and $X_{21}$ is K or R (b) R$X_{18}X_{19}X_{20}$RPS (SEQ ID NO: 145), wherein $X_{18}$ is H or N; $X_{19}$ is H or N; and $X_{20}$ is L or Q. | | (a) A$X_{22}X_{23}$DD$X_{24}$ $X_{25}X_{26}X_{27}$WL (SEQ ID NO: 134), wherein $X_{22}$ is A or S; $X_{23}$ is H or W; $X_{24}$ is E, H, R, or S; $X_{25}$ is H, L, R, S, or V; $X_{26}$ is H, M, N, Q, S, T; and $X_{27}$ is A or G. (b) A$X_{22}X_{23}$DD$X_{24}$ $X_{25}X_{26}X_{27}$WL (SEQ ID NO: 141), wherein $X_{22}$ is A or S; $X_{23}$ is H or W; $X_{24}$ is E, R, or S; $X_{25}$ is H, L, or R; $X_{26}$ | |

Also within the scope of the present disclosure are functional variants of AB001 as determined by the mutagenesis screening disclosed in Example 10 below. Relative to AB001, such functional variants may comprise one or more amino acid residue variations as listed in Tables 20A and 20B that exhibit binding activity to PRLR (e.g., showing similar binding activity to PRLR or retaining binding activity although in a reduced level). In some embodiments, the functional variants may comprise up to 10 amino acid variations in the heavy chain CDRs 1-3 collectively, for example, up to 8 amino acid variations, up to 7 amino acid variations, up to 6 amino acid variations, up to 5 amino acid variations, up to 4 amino acid variations, up to 3 amino acid variations, up to 2 amino acid variations, or up to 1 amino acid variations.

Alternatively, or in addition, the functional variants may comprise up to 10 amino acid variations in the light chain CDRs 1-3 collectively, for example, up to 8 amino acid variations, up to 7 amino acid variations, up to 6 amino acid variations, up to 5 amino acid variations, up to 4 amino acid variations, up to 3 amino acid variations, up to 2 amino acid variations, or up to 1 amino acid variations.

In some examples, the functional variants may comprise up to 10 amino acid variations in both the heavy chain CDRs 1-3 and the light chain CDRs 1-3 collectively, for example, up to 8 amino acid variations, up to 7 amino acid variations, up to 6 amino acid variations, up to 5 amino acid variations, up to 4 amino acid variations, up to 3 amino acid variations, up to 2 amino acid variations, or up to 1 amino acid variations.

As used herein, "collectively" refers to the total number of variations in the three heavy chain CDRs and/or the three light chain CDRs relative to those in AB001.

Alternatively, or in addition, the functional variants of AB001 as provided herein may share a high sequence similarity to the VH and VL of AB001. For example, the VH of the functional variant may be at least 70% identical (e.g., at least 75%, at least 80%, at least 85%, at least 90%, at least 95% or above) to the VH of AB001. Alternatively, or in addition, the VL of the functional variant may be at least 70% identical (e.g., at least 75%, at least 80%, at least 85%, at least 90%, at least 95% or above) to the VL of AB001.

In some aspects, provided herein are means for binding to PRLR such as human PRLR and medical uses of means for binding to PRLR such as human PRLR for treating diseases associated with PRLR as those disclosed herein.

(ii) Framework Regions

The anti-prolactin receptor antibodies provided herein may comprise a VH having heavy chain framework regions (HC FRs) derived from IGHV3-66*01. Alternatively or in addition, the antibody may comprise a VL having light chain framework regions (LC FRs) derived from IGKV4-1*01.

In some embodiments, the anti-prolactin receptor antibodies provided herein may comprise heavy chain framework regions (HC FRs) comprising a HC FR1 region set forth as QVQLVQSGGGLVQPGGSLRLSCAASGF$X_{28}X_{29}X_{30}$ (SEQ ID NO: 135), wherein $X_{28}$ is S or T; $X^{29}$ is H or Y; and $X_{30}$ is H, S, or V; a HC FR2 set forth as WVRQAPGKGLEW$X_{31}$S (SEQ ID NO: 136), wherein $X_{31}$ is M or V; a HC FR3 set forth as GRFTISRDNAKNTLYLQLNSLRAEDTAMYYC$X_{32}X_{33}$ (SEQ ID NO: 137), wherein $X_{32}$ is A or S; and $X_{33}$ is K or R; a HC FR4 set forth as WGQGTLVTVSS (SEQ ID NO:

55). Alternatively or in addition, the anti-PRLR antibodies may comprise LC FR1 region set forth as QSVLTQPPSASGTPGQRVTISC (SEQ ID NO: 56) or DIQLTQSPSSVSVSVGERVTIDC (SEQ ID NO: 57); LC FR2 set forth as WYQQKPGQAPQ$X_{35}X_{36}X_{37}X_{38}$ (SEQ ID NO: 138), wherein $X_{35}$ is H or L; $X_{36}$ is K or L; $X_{37}$ is I or M; and $X_{38}$ is F or Y; LC FR3 set forth as GVPDRFSGSKSGTSASLAISGLRSEDEADYYC (SEQ ID NO: 63) or GVPDRFSGSKSGTDATLTISSLQAEDAAVYYC (SEQ ID NO: 64); and LC FR4 set forth as FGGGTKLTVL (SEQ ID NO: 65) or FGQGTKLEIK (SEQ ID NO: 66).

Exemplary heavy chain FR1, FR2, FR3, and FR4 sequences are provided in Table 3 below. Exemplary light chain FR1, FR2, FR3, and FR4 sequences are provided in Table 4 below.

TABLE 3

Exemplary Heavy Chain Framework and Constant Region Sequences

| Framework Regions | Sequences | SEQ ID NO |
|---|---|---|
| HC FR1 | EVQLLESGGGLVQPGGSLRLSCAASGFTFS | 44 |
| | QVQLVQSGGGLVQPGGSLRLSCAASGFTYS | 45 |
| | QVQLVQSGGGLVQPGGSLRLSCAASGFSYS | 46 |
| | QVQLVQSGGGLVQPGGSLRLSCAASGFSYV | 47 |
| | QVQLVQSGGGLVQPGGSLRLSCAASGFTHH | 48 |
| | QVQLVQSGGGLVQPGGSLRLSCAASGF$X_{28}X_{29}X_{30}$, wherein $X_{28}$ is S or T; $X_{29}$ is H or Y; and $X_{30}$ is H, S, or V | 135 |
| HC FR2 | WVRQAPGKGLEWVS | 49 |
| | WVRQAPGKGLEWMS | 50 |
| | WVRQAPGKGLEW$X_{31}$S, wherein $X_{31}$ is V or M | 136 |
| HC FR3 | GRFTISRDNSKNTLYLQMNSLRAEDTAVYYCAR | 51 |
| | GRFTISRDNAKNTLYLQLNSLRAEDTAMYYCAR | 52 |
| | GRFTISRDNAKNTLYLQLNSLRAEDTAMYYCAK | 53 |
| | GRFTISRDNAKNTLYLQLNSLRAEDTAMYYCSR | 54 |
| | GRFTISRDNAKNTLYLQLNSLRAEDTAMYYC$X_{32}$ $X_{33}$, wherein $X_{32}$ is A or S; and $X_{33}$ is K or R | 137 |
| HC FR4 | WGQGTLVTVSS | 55 |
| HC Constant Region 1 | ASTKGPSVFPLAPCSRSTSESTAALGCLVKDYFP EPVTVSWNSGALTSGVHTFPAVLQSSGLYSLSSVV TVPSSNFGTQTYTCNVDHKPSNTKVDKTVERKC CVECPPCPAPPVAGPSVFLFPPKPKDTLMISRTP EVTCVVVDVSHEDPEVQFNWYVDGVEVHNAKTKP REEQFNSTFRVVSVLTVVHQDWLNGKEYKCKVS NKGLPAPIEKTISKTKGQPREPQVYTLPPSREEMT KNQVSLTCLVKGFYPSDIAVEWESNGQPENNYKT TPPMLDSDGSFFLYSKLTVDKSRWQQGNVFSCSV MHEALHNHYTQKSLSLSPGK | 97 |
| HC Constant Region 2 | ASTKGPSVFPLAPSSKSTSGGTAALGCLVKDYFPE PVTVSWNSGALTSGVHTFPAVLQSSGLYSLSSVVT VPSSSLGTQTYICNVNHKPSNTKVDKKVEPKSCD KTHTCPPCPAPEAAGGPSVFLFPPKPKDTLMISRT PEVTCVVVSVSHEDPEVKFNWYVDGVEVHNAK TKPREEQYNSTYRVVSVLTVLHQDWLNGKEYKC KVSNKALPAPIEKTISKAKGQPREPQVYTLPPSRD ELTKNQVSLTCLVKGFYPSDIAVEWESNGQPENN YKTTPPVLDSDGSFFLYSKLTVDKSRWQQGNVFS CSVLHEALHSHYTQKSLSLSPGK | 98 |

TABLE 4

Exemplary Light Chain Framework and Constant Region Sequences

| Framework Regions | Sequences | SEQ ID NO |
|---|---|---|
| LC FR1 | QSVLTQPPSASGTPGQRVTISC | 56 |
| | DIQLTQSPSSVSVSVGERVTIDC | 57 |
| LC FR2 | WYQQLPGTAPKLLIY | 58 |
| | WYQQKPGQAPQLLIY | 59 |
| | WYQQKPGQAPQLKIY | 60 |
| | WYQQKPGQAPQLLIF | 61 |

TABLE 4-continued

| Exemplary Light Chain Framework and Constant Region Sequences | | |
|---|---|---|
| Framework Regions | Sequences | SEQ ID NO |
| | WYQQKPGQAPQHLIY | 62 |
| | WYQQKPGQAPQ$X_{34}X_{35}X_{36}X_{37}$, wherein $X_{34}$ is H or L; $X_{35}$ is K or L; $X_{36}$ is I or M; and $X_{37}$ is F or Y | 138 |
| LC FR3 | GVPDRFSGSKSGTSASLAISGLRSEDEADYYC | 63 |
| | GVPDRFSGSKSGTDATLTISSLQAEDAAVYYC | 64 |
| LC FR4 | FGGGTKLTVL | 65 |
| | FGQGTKLEIK | 66 |
| LC Constant Region 1 | GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS | 99 |
| LC Constant Region 2 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 100 |

(iii) Constant Regions

In some embodiments, the anti-PRLR antibodies provided herein are full-length antibodies, for example, IgG (e.g., IgG1) molecules, comprising a heavy chain that comprises any of the VH regions provided herein and a heavy chain constant region, and a light chain that comprises any of the VL regions provided herein and a light chain constant region. Antibody heavy and light chain constant regions are well known in the art, e.g., those provided in the IMGT database (www.imgt.org) or at www.vbase2.org/vbstat.php., both of which are incorporated by reference herein.

In some embodiments, the heavy chain of any of the anti-prolactin receptor antibodies as described herein can further comprise a heavy chain constant region (CH) or a portion thereof (e.g., CH1, CH2, CH3, or a combination thereof). The heavy chain constant region can of any suitable origin, e.g., human, mouse, rat, or rabbit. In some instances, the heavy chain constant region can be of a human IgG molecule, for example, an IgG1 molecule. Exemplary heavy chain constant regions are provided in Table 3 above.

In some examples, the heavy chain constant region may be wild-type. Alternatively, the heavy chain constant region may comprise one or more mutations relative to the wild-type counterpart, such as mutations that in the Fc region that modulate binding activity to Fc receptors. In some examples, the heavy chain constant region may comprise one or more mutations at positions L234, L235, D265, M428, and N434. Exemplary variations include L234A, L235A, D265S, M428L, and/or N434S. An exemplary heavy chain constant region for use in the anti-PRLR antibodies provided herein can comprise the amino acid sequence of SEQ ID NO: 98.

Alternatively, or in addition, the light chain of the anti-prolactin receptor antibody can further comprise a light chain constant region (CL), which can be any CL known in the art. In some examples, the CL is a kappa light chain. In other examples, the CL is a lambda light chain. Exemplary light chain constant region for use in the anti-PRLR antibodies provided herein can comprise the amino acid sequence of SEQ ID NO: 99 or 100 (e.g., SEQ ID NO: 100).

Table 5 below provides sequences of exemplary anti-PRLR antibodies, as well as sequences for the parent AB000 clone.

TABLE 5

| Sequences of Exemplary Anti-PRLR Antibodies | | | |
|---|---|---|---|
| Description | | Sequence | SEQ ID NO |
| AB000 | $V_H$ | EVQLLESGGGLVQPGGSLRLSCAASGFTFSSYWMHWVRQAPGKGLEWVSDIARLSSYTNYADSVKGRFTISRDNSKNTLYLQMNSLRAEDTAVYYCARGLDARRMDYWGQGTLVTVSS | 67 |
| | H | EVQLLESGGGLVQPGGSLRLSCAASGFTFSSYWMHWVRQAPGKGLEWVSDIARLSSYTNYADSVKGRFTISRDNSKNTLYLQMNSLRAEDTAVYYCARGLDARRMDYWGQGTLVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK | 101 |

TABLE 5-continued

Sequences of Exemplary Anti-PRLR Antibodies

| Description | | Sequence | SEQ ID NO |
|---|---|---|---|
| | $V_L$ | QSVLTQPPSASGTPGQRVTISCTGSSSNIGAGYVVHWYQQLP<br>GTAPKLLIYRNNQRPSGVPDRFSGSKSGTSASLAISGLRSEDE<br>ADYYCAAWDDSLNGWLFGGGTKLTVL | 82 |
| | L | QSVLTQPPSASGTPGQRVTISCTGSSSNIGAGYVVHWYQQLP<br>GTAPKLLIYRNNQRPSGVPDRFSGSKSGTSASLAISGLRSEDE<br>ADYYCAAWDDSLNGWLFGGGTKLTVLGQPKAAPSVTLFPPS<br>SEELQANKATLVCLISDFYPGAVTVAWKADSSPVKAGVETTT<br>PSKQSNNKYAASSYLSLTPEQWKSHRSYSCQVTHEGSTVEKT<br>VAPTECS | 116 |
| AB001 | $V_H$ | QVQLVQSGGGLVQPGGSLRLSCAASGFTYSDYWMHWVRQA<br>PGKGLEWVSDISRLKPYTNYADSVKGRFTISRDNAKNTLYLQ<br>LNSLRAEDTAMYYCARGLDARRMDYWGQGTLVTVSS | 68 |
| | H | QVQLVQSGGGLVQPGGSLRLSCAASGFTYSDYWMHWVRQA<br>PGKGLEWVSDISRLKPYTNYADSVKGRFTISRDNAKNTLYLQ<br>LNSLRAEDTAMYYCARGLDARRMDYWGQGTLVTVSSASTK<br>GPSVFPLAPSSKSTSGGTAALGCLVKDYFPEPVTVSWNSGALT<br>SGVHTFPAVLQSSGLYSLSSVVTVPSSSLGTQTYICNVNHKPS<br>NTKVDKKVEPKSCDKTHTCPPCPAPEAAGGPSVFLFPPKPKD<br>TLMISRTPEVTCVVVSVSHEDPEVKFNWYVDGVEVHNAKTK<br>PREEQYNSTYRVVSVLIVLHQDWLNGKEYKCKVSNKALPAP<br>IEKTISKAKGQPREPQVYTLPPSRDELTKNQVSLTCLVKGFYP<br>SDIAVEWESNGQPENNYKTTPPVLDSDGSFFLYSKLTVDKSR<br>WQQGNVFSCSVLHEALHSHYTQKSLSLSPGK | 102 |
| | $V_L$ | DIQLTQSPSSVSVSVGERVTIDCTGSGTNIGAGYVVHWYQQK<br>PGQAPQLLIYRNNLRPSGVPDRFSGSKSGTDATLTISSLQAED<br>AAVYYCASWDDRHQAWLFGQGTKLEIK | 83 |
| | L | DIQLTQSPSSVSVSVGERVTIDCTGSGTNIGAGYVVHWYQQK<br>PGQAPQLLIYRNNLRPSGVPDRFSGSKSGTDATLTISSLQAED<br>AAVYYCASWDDRHQAWLFGQGTKLEIKRTVAAPSVFIFPPSD<br>EQLKSGTASVVCLLNNFYPREAKVQWKVDNALQSGNSQESV<br>TEQDSKDSTYSLSSTLTLSKADYEKHKVYACEVTHQGLSSPV<br>TKSFNRGEC | 117 |
| AB002 | $V_H$ | QVQLVQSGGGLVQPGGSLRLSCAASGFSYSSSYWMHWVRQA<br>PGKGLEWVSDISRLSPYTGYADSVKGRFTISRDNAKNTLYLQ<br>LNSLRAEDTAMYYCARGMDAKRMDHWGQGTLVTVSS | 69 |
| | H | QVQLVQSGGGLVQPGGSLRLSCAASGFSYSSSYWMHWVRQA<br>PGKGLEWVSDISRLSPYTGYADSVKGRFTISRDNAKNTLYLQ<br>LNSLRAEDTAMYYCARGMDAKRMDHWGQGTLVTVSSAST<br>KGPSVFPLAPSSKSTSGGTAALGCLVKDYFPEPVTVSWNSGA<br>LTSGVHTFPAVLQSSGLYSLSSVVTVPSSSLGTQTYICNVNHKP<br>SNTKVDKKVEPKSCDKTHTCPPCPAPEAAGGPSVFLFPPKPK<br>DTLMISRTPEVTCVVVSVSHEDPEVKFNWYVDGVEVHNAKT<br>KPREEQYNSTYRVVSVLTVLHQDWLNGKEYKCKVSNKALPA<br>PIEKTISKAKGQPREPQVYTLPPSRDELTKNQVSLTCLVKGFY<br>PSDIAVEWESNGQPENNYKTTPPVLDSDGSFFLYSKLTVDKSR<br>WQQGNVFSCSVLHEALHSHYTQKSLSLSPGK | 103 |
| | $V_L$ | DIQLTQSPSSVSVSVGERVTIDCTGSSSNIGAGYVVHWYQQKP<br>GQAPQLLIYRNNLRPSGVPDRFSGSKSGTDATLTISSLQAEDA<br>AVYYCASWDDSLQAWLFGQGTKLEIK | 84 |
| | L | DIQLTQSPSSVSVSVGERVTIDCTGSSSNIGAGYVVHWYQQKP<br>GQAPQLLIYRNNLRPSGVPDRFSGSKSGTDATLTISSLQAEDA<br>AVYYCASWDDSLQAWLFGQGTKLEIKRTVAAPSVFIFPPSDE<br>QLKSGTASVVCLLNNFYPREAKVQWKVDNALQSGNSQESVT<br>EQDSKDSTYSLSSTLTLSKADYEKHKVYACEVTHQGLSSPVT<br>KSFNRGEC | 118 |
| AB003 | $V_H$ | QVQLVQSGGGLVQPGGSLRLSCAASGFTYSDFWMHWVRQA<br>PGKGLEWMSDISRLSPYTNYADSVKGRFTISRDNAKNTLYLQ<br>LNSLRAEDTAMYYCARGLDARRMDYWGQGTLVTVSS | 70 |
| | H | QVQLVQSGGGLVQPGGSLRLSCAASGFTYSDFWMHWVRQA<br>PGKGLEWMSDISRLSPYTNYADSVKGRFTISRDNAKNTLYLQ<br>LNSLRAEDTAMYYCARGLDARRMDYWGQGTLVTVSSASTK<br>GPSVFPLAPSSKSTSGGTAALGCLVKDYFPEPVTVSWNSGALT<br>SGVHTFPAVLQSSGLYSLSSVVTVPSSSLGTQTYICNVNHKPS<br>NTKVDKKVEPKSCDKTHTCPPCPAPEAAGGPSVFLFPPKPKD<br>TLMISRTPEVTCVVVSVSHEDPEVKFNWYVDGVEVHNAKTK<br>PREEQYNSTYRVVSVLTVLHQDWLNGKEYKCKVSNKALPAP<br>IEKTISKAKGQPREPQVYTLPPSRDELTKNQVSLTCLVKGFYP<br>SDIAVEWESNGQPENNYKTTPPVLDSDGSFFLYSKLTVDKSR<br>WQQGNVFSCSVLHEALHSHYTQKSLSLSPGK | 104 |
| | $V_L$ | DIQLTQSPSSVSVSVGERVTIDCTGSSSNLGAGYVNHWYQQK<br>PGQAPQLLMYRNNQRPSGVPDRFSGSKSGTDATLTISSLQAE<br>DAAVYYCASWDDHSSAWLFGQGTKLEIK | 85 |

TABLE 5-continued

| Sequences of Exemplary Anti-PRLR Antibodies | | | |
|---|---|---|---|
| Description | | Sequence | SEQ ID NO |
| | L | DIQLTQSPSSVSVSVGERVTIDCTGSSSNLGAGYVNHWYQQK<br>PGQAPQLLMYRNNQRPSGVPDRFSGSKSGTDATLTISSLQAE<br>DAAVYYCASWDDHSSAWLFGQGTKLEIKRTVAAPSVFIFPPS<br>DEQLKSGTASVVCLLNNFYPREAKVQWKVDNALQSGNSQES<br>VTEQDSKDSTYSLSSTLTLSKADYEKHKVYACEVTHQGLSSP<br>VTKSFNRGEC | 119 |
| AB004 | $V_H$ | QVQLVQSGGGLVQPGGSLRLSCAASGFSYVSYWMHWVRQA<br>PGKGLEWVSDISRISPYTNYADSVKGRFTISRDNAKNTLYLQL<br>NSLRAEDTAMYYCARGLDARRMDYWGQGTLVTVSS | 71 |
| | H | QVQLVQSGGGLVQPGGSLRLSCAASGFSYVSYWMHWVRQA<br>PGKGLEWVSDISRISPYTNYADSVKGRFTISRDNAKNTLYLQL<br>NSLRAEDTAMYYCARGLDARRMDYWGQGTLVTVSSASTKG<br>PSVFPLAPSSKSTSGGTAALGCLVKDYFPEPVTVSWNSGALTS<br>GVHTFPAVLQSSGLYSLSSVVTVPSSSLGTQTYICNVNHKPSN<br>TKVDKKVEPKSCDKTHTCPPCPAPEAAGGPSVFLFPPKPKDT<br>LMISRTPEVTCVVVSVSHEDPEVKFNWYVDGVEVHNAKTKP<br>REEQYNSTYRVVSVLTVLHQDWLNGKEYKCKVSNKALPAPI<br>EKTISKAKGQPREPQVYTLPPSRDELTKNQVSLTCLVKGFYPS<br>DIAVEWESNGQPENNYKTTPPVLDSDGSFFLYSKLTVDKSRW<br>QQGNVFSCSVLHEALHSHYTQKSLSLSPGK | 105 |
| | $V_L$ | DIQLTQSPSSVSVSVGERVTIDCTGSSTNLGAGYVVHWYQQK<br>PGQAPQLLIYRNNQRPSGVPDRFSGSKSGTDATLTISSLQAED<br>AAVYYCAAWDDSVSGWLFGQGTKLEIK | 86 |
| | L | DIQLTQSPSSVSVSVGERVTIDCTGSSTNLGAGYVVHWYQQK<br>PGQAPQLLIYRNNQRPSGVPDRFSGSKSGTDATLTISSLQAED<br>AAVYYCAAWDDSVSGWLFGQGTKLEIKRTVAAPSVFIFPPSD<br>EQLKSGTASVVCLLNNFYPREAKVQWKVDNALQSGNSQESV<br>TEQDSKDSTYSLSSTLTLSKADYEKHKVYACEVTHQGLSSPV<br>TKSFNRGEC | 120 |
| AB005 | $V_L$ | QVQLVQSGGGLVQPGGSLRLSCAASGFTYSDYWMHWVRQA<br>PGKGLEWMSDISRLSPYTGYADSVKGRFTISRDNAKNTLYLQ<br>LNSLRAEDTAMYYCARGLDARRMDYWGQGTLVTVSS | 72 |
| | H | QVQLVQSGGGLVQPGGSLRLSCAASGFTYSDYWMHWVRQA<br>PGKGLEWMSDISRLSPYTGYADSVKGRFTISRDNAKNTLYLQ<br>LNSLRAEDTAMYYCARGLDARRMDYWGQGTLVTVSSASTK<br>GPSVFPLAPSSKSTSGGTAALGCLVKDYFPEPVTVSWNSGALT<br>SGVHTFPAVLQSSGLYSLSSVVTVPSSSLGTQTYICNVNHKPS<br>NTKVDKKVEPKSCDKTHTCPPCPAPEAAGGPSVFLFPPKPKD<br>TLMISRTPEVTCVVVSVSHEDPEVKFNWYVDGVEVHNAKTK<br>PREEQYNSTYRVVSVLTVLHQDWLNGKEYKCKVSNKALPAP<br>IEKTISKAKGQPREPQVYTLPPSRDELTKNQVSLTCLVKGFYP<br>SDIAVEWESNGQPENNYKTTPPVLDSDGSFFLYSKLTVDKSR<br>WQQGNVFSCSVLHEALHSHYTQKSLSLSPGK | 106 |
| | $V_L$ | DIQLTQSPSSVSVSVGERVTIDCTGSSSNLGGGYVVHWYQQK<br>PGQAPQLLIFRNNQRPSGVPDRFSGSKSGTDATLTISSLQAED<br>AAVYYCASWDDSLQGWLFGQGTKLEIK | 87 |
| | L | DIQLTQSPSSVSVSVGERVTIDCTGSSSNLGGGYVVHWYQQK<br>PGQAPQLLIFRNNQRPSGVPDRFSGSKSGTDATLTISSLQAED<br>AAVYYCASWDDSLQGWLFGQGTKLEIKRTVAAPSVFIFPPSD<br>EQLKSGTASVVCLLNNFYPREAKVQWKVDNALQSGNSQESV<br>TEQDSKDSTYSLSSTLTLSKADYEKHKVYACEVTHQGLSSPV<br>TKSFNRGEC | 121 |
| AB006 | $V_H$ | QVQLVQSGGGLVQPGGSLRLSCAASGFSYSDYWMHWVRQA<br>PGKGLEWVSDISRLSPYTNYADSVKGRFTISRDNAKNTLYLQ<br>LNSLRAEDTAMYYCARGLDARRMSYWGQGTLVTVSS | 73 |
| | H | QVQLVQSGGGLVQPGGSLRLSCAASGFSYSDYWMHWVRQA<br>PGKGLEWVSDISRLSPYTNYADSVKGRFTISRDNAKNTLYLQ<br>LNSLRAEDTAMYYCARGLDARRMSYWGQGTLVTVSSASTK<br>GPSVFPLAPSSKSTSGGTAALGCLVKDYFPEPVTVSWNSGALT<br>SGVHTFPAVLQSSGLYSLSSVVTVPSSSLGTQTYICNVNHKPS<br>NTKVDKKVEPKSCDKTHTCPPCPAPEAAGGPSVFLFPPKPKD<br>TLMISRTPEVTCVVVSVSHEDPEVKFNWYVDGVEVHNAKTK<br>PREEQYNSTYRVVSVLTVLHQDWLNGKEYKCKVSNKALPAP<br>IEKTISKAKGQPREPQVYTLPPSRDELTKNQVSLTCLVKGFYP<br>SDIAVEWESNGQPENNYKTTPPVLDSDGSFFLYSKLTVDKSR<br>WQQGNVFSCSVLHEALHSHYTQKSLSLSPGK | 107 |
| | $V_L$ | DIQLTQSPSSVSVSVGERVTIDCTGSASNIGAGYVVHWYQQK<br>PGQAPQLLIYRNNVRPSGVPDRFSGSKSGTDATLTISSLQAED<br>AAVYYCAAWDDHRTAWLFGQGTKLEIK | 88 |
| | L | DIQLTQSPSSVSVSVGERVTIDCTGSASNIGAGYVVHWYQQK<br>PGQAPQLLIYRNNVRPSGVPDRFSGSKSGTDATLTISSLQAED<br>AAVYYCAAWDDHRTAWLFGQGTKLEIKRTVAAPSVFIFPPSD | 122 |

TABLE 5-continued

Sequences of Exemplary Anti-PRLR Antibodies

| Description | | Sequence | SEQ ID NO |
|---|---|---|---|
| | | EQLKSGTASVVCLLNNFYPREAKVQWKVDNALQSGNSQESV<br>TEQDSKDSTYSLSSTLTLSKADYEKHKVYACEVTHQGLSSPV<br>TKSFNRGEC | |
| AB007 | $V_H$ | QVQLVQSGGGLVQPGGSLRLSCAASGFSYSDYWMHWVRQA<br>PGKGLEWVSDISRLSPYTNYADSVKGRFTISRDNAKNTLYLQ<br>LNSLRAEDTAMYYCARGLDARRMSYWGQGTLVTVSS | 73 |
| | H | QVQLVQSGGGLVQPGGSLRLSCAASGFSYSDYWMHWVRQA<br>PGKGLEWVSDISRLSPYTNYADSVKGRFTISRDNAKNTLYLQ<br>LNSLRAEDTAMYYCARGLDARRMSYWGQGTLVTVSSASTK<br>GPSVFPLAPSSKSTSGGTAALGCLVKDYFPEPVTVSWNSGALT<br>SGVHTFPAVLQSSGLYSLSSVVTVPSSSLGTQTYICNVNHKPS<br>NTKVDKKVEPKSCDKTHTCPPCPAPEAAGGPSVFLFPPKPKD<br>TLMISRTPEVTCVVVSVSHEDPEVKFNWYVDGVEVHNAKTK<br>PREEQYNSTYRVVSVLTVLHQDWLNGKEYKCKVSNKALPAP<br>IEKTISKAKGQPREPQVYTLPPSRDELTKNQVSLTCLVKGFYP<br>SDIAVEWESNGQPENNYKTTPPVLDSDGSFFLYSKLTVDKSR<br>WQQGNVFSCSVLHEALHSHYTQKSLSLSPGK | 107 |
| | $V_L$ | DIQLTQSPSSVSVSVGERVTIDCTGSSSNIGHGYVVHWYQQKP<br>GQAPQLKIYRNNQRPSGVPDRFSGSKSGTDATLTISSLQAEDA<br>AVYYCAAWDDSLNGWLFGQGTKLEIK | 89 |
| | L | DIQLTQSPSSVSVSVGERVTIDCTGSSSNIGHGYVVHWYQQKP<br>GQAPQLKIYRNNQRPSGVPDRFSGSKSGTDATLTISSLQAEDA<br>AVYYCAAWDDSLNGWLFGQGTKLEIKRTVAAPSVFIFPPSDE<br>QLKSGTASVVCLLNNFYPREAKVQWKVDNALQSGNSQESVT<br>EQDSKDSTYSLSSTLTLSKADYEKHKVYACEVTHQGLSSPVT<br>KSFNRGEC | 123 |
| AB008 | $V_H$ | QVQLVQSGGGLVQPGGSLRLSCAASGFTHHSYWLHWVRQA<br>PGKGLEWVSDISRLSPYTNYADSVKGRFTISRDNAKNTLYLQ<br>LNSLRAEDTAMYYCARGMDARRMDYWGQGTLVTVSS | 75 |
| | H | QVQLVQSGGGLVQPGGSLRLSCAASGFTHHSYWLHWVRQA<br>PGKGLEWVSDISRLSPYTNYADSVKGRFTISRDNAKNTLYLQ<br>LNSLRAEDTAMYYCARGMDARRMDYWGQGTLVTVSSASTK<br>GPSVFPLAPSSKSTSGGTAALGCLVKDYFPEPVTVSWNSGALT<br>SGVHTFPAVLQSSGLYSLSSVVTVPSSSLGTQTYICNVNHKPS<br>NTKVDKKVEPKSCDKTHTCPPCPAPEAAGGPSVFLFPPKPKD<br>TLMISRTPEVTCVVVSVSHEDPEVKFNWYVDGVEVHNAKTK<br>PREEQYNSTYRVVSVLTVLHQDWLNGKEYKCKVSNKALPAP<br>IEKTISKAKGQPREPQVYTLPPSRDELTKNQVSLTCLVKGFYP<br>SDIAVEWESNGQPENNYKTTPPVLDSDGSFFLYSKLTVDKSR<br>WQQGNVFSCSVLHEALHSHYTQKSLSLSPGK | 109 |
| | $V_L$ | DIQLTQSPSSVSVSVGERVTIDCTGSSSNLGAGYVVHWYQQK<br>PGQAPQHLIYRNNQRPSGVPDRFSGSKSGTDATLTISSLQAED<br>AAVYYCASWDDSHMAWLFGQGTKLEIK | 90 |
| | L | DIQLTQSPSSVSVSVGERVTIDCTGSSSNLGAGYVVHWYQQK<br>PGQAPQHLIYRNNQRPSGVPDRFSGSKSGTDATLTISSLQAED<br>AAVYYCASWDDSHMAWLFGQGTKLEIKRTVAAPSVFIFPPSD<br>EQLKSGTASVVCLLNNFYPREAKVQWKVDNALQSGNSQESV<br>TEQDSKDSTYSLSSTLTLSKADYEKHKVYACEVTHQGLSSPV<br>TKSFNRGEC | 124 |
| AB009 | $V_H$ | QVQLVQSGGGLVQPGGSLRLSCAASGFTHHSYWLHWVRQA<br>PGKGLEWVSDISRLSPYTNYADSVKGRFTISRDNAKNTLYLQ<br>LNSLRAEDTAMYYCARGMDARRMDYWGQGTLVTVSS | 75 |
| | H | QVQLVQSGGGLVQPGGSLRLSCAASGFTHHSYWLHWVRQA<br>PGKGLEWVSDISRLSPYTNYADSVKGRFTISRDNAKNTLYLQ<br>LNSLRAEDTAMYYCARGMDARRMDYWGQGTLVTVSSASTK<br>GPSVFPLAPSSKSTSGGTAALGCLVKDYFPEPVTVSWNSGALT<br>SGVHTFPAVLQSSGLYSLSSVVTVPSSSLGTQTYICNVNHKPS<br>NTKVDKKVEPKSCDKTHTCPPCPAPEAAGGPSVFLFPPKPKD<br>TLMISRTPEVTCVVVSVSHEDPEVKFNWYVDGVEVHNAKTK<br>PREEQYNSTYRVVSVLTVLHQDWLNGKEYKCKVSNKALPAP<br>IEKTISKAKGQPREPQVYTLPPSRDELTKNQVSLTCLVKGFYP<br>SDIAVEWESNGQPENNYKTTPPVLDSDGSFFLYSKLTVDKSR<br>WQQGNVFSCSVLHEALHSHYTQKSLSLSPGK | 109 |
| | $V_L$ | DIQLTQSPSSVSVSVGERVTIDCTGSTSNLGAGYVVHWYQQK<br>PGQAPQLLIYRHHQRPSGVPDRFSGSKSGTDATLTISSLQAED<br>AAVYYCASWDDSHMAWLFGQGTKLEIK | 91 |
| | L | DIQLTQSPSSVSVSVGERVTIDCTGSTSNLGAGYVVHWYQQK<br>PGQAPQLLIYRHHQRPSGVPDRFSGSKSGTDATLTISSLQAED<br>AAVYYCASWDDSHMAWLFGQGTKLEIKRTVAAPSVFIFPPSD<br>EQLKSGTASVVCLLNNFYPREAKVQWKVDNALQSGNSQESV<br>TEQDSKDSTYSLSSTLTLSKADYEKHKVYACEVTHQGLSSPV<br>TKSFNRGEC | 125 |

TABLE 5-continued

Sequences of Exemplary Anti-PRLR Antibodies

| Description | | Sequence | SEQ ID NO |
|---|---|---|---|
| AB010 | $V_H$ | QVQLVQSGGGLVQPGGSLRLSCAASGFTYSSHWLHWVRQAP GKGLEWVSDISRLSPYTNYADSVKGRFTISRDNAKNTLYLQL NSLRAEDTAMYYCAKGLDARRMDHWGQGTLVTVSS | 77 |
| | H | QVQLVQSGGGLVQPGGSLRLSCAASGFTYSSHWLHWVRQAP GKGLEWVSDISRLSPYTNYADSVKGRFTISRDNAKNTLYLQL NSLRAEDTAMYYCAKGLDARRMDHWGQGTLVTVSSASTKG PSVFPLAPSSKSTSGGTAALGCLVKDYFPEPVTVSWNSGALTS GVHTFPAVLQSSGLYSLSSVVTVPSSSLGTQTYICNVNHKPSN TKVDKKVEPKSCDKTHTCPPCPAPEAAGGPSVFLFPPKPKDT LMISRTPEVTCVVVSVSHEDPEVKFNWYVDGVEVHNAKTKP REEQYNSTYRVVSVLTVLHQDWLNGKEYKCKVSNKALPAPI EKTISKAKGQPREPQVYTLPPSRDELTKNQVSLTCLVKGFYPS DIAVEWESNGQPENNYKTTPPVLDSDGSFFLYSKLTVDKSRW QQGNVFSCSVLHEALHSHYTQKSLSLSPGK | 111 |
| | $V_L$ | DIQLTQSPSSVSVSVGERVTIDCTGSSSNLGAGYVVHWYQQK PGQAPQLLIYRHHQKPSGVPDRFSGSKSGTDATLTISSLQAED AAVYYCASWDDSHMAWLFGQGTKLEIK | 92 |
| | L | DIQLTQSPSSVSVSVGERVTIDCTGSSSNLGAGYVVHWYQQK PGQAPQLLIYRHHQKPSGVPDRFSGSKSGTDATLTISSLQAED AAVYYCASWDDSHMAWLFGQGTKLEIKRTVAAPSVFIFPPSD EQLKSGTASVVCLLNNFYPREAKVQWKVDNALQSGNSQESV TEQDSKDSTYSLSSTLTLSKADYEKHKVYACEVTHQGLSSPV TKSFNRGEC | 126 |
| AB011 | $V_H$ | QVQLVQSGGGLVQPGGSLRLSCAASGFTHSSYWMHWVRQA PGKGLEWVSDISRLSPYHNYADSVKGRFTISRDNAKNTLYLQ LNSLRAEDTAMYYCSRGLDARRMDYWGQGTLVTVSS | 78 |
| | H | QVQLVQSGGGLVQPGGSLRLSCAASGFTHSSYWMHWVRQA PGKGLEWVSDISRLSPYHNYADSVKGRFTISRDNAKNTLYLQ LNSLRAEDTAMYYCSRGLDARRMDYWGQGTLVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSCDKTHTCPPCPAPEAAGGPSVFLFPPKPKD TLMISRTPEVTCVVVSVSHEDPEVKFNWYVDGVEVHNAKTK PREEQY NSTYRVVSVLTVLHQDWLNGKEYKCKVSNKALPAPIEKTISK AKGQPREPQVYTLPPSRDELTKNQVSLTCLVKGFYPSDIAVE WESNGQPENNYKTTPPVLDSDGSFFLYSKLTVDKSRWQQGN VFSCSVLHEALHSHYTQKSLSLSPGK | 112 |
| | $V_L$ | DIQLTQSPSSVSVSVGERVTIDCTGSSTNLGAGYVVHWYQQK PGQAPQLLIYRHHQRPSGVPDRFSGSKSGTDATLTISSLQAED AAVYYCASWDDSHMAWLFGQGTKLEIK | 93 |
| | L | DIQLTQSPSSVSVSVGERVTIDCTGSSTNLGAGYVVHWYQQK PGQAPQLLIYRHHQRPSGVPDRFSGSKSGTDATLTISSLQAED AAVYYCASWDDSHMAWLFGQGTKLEIKRTVAAPSVFIFPPSD EQLKSGTASVVCLLNNFYPREAKVQWKVDNALQSGNSQESV TEQDSKDSTYSLSSTLTLSKADYEKHKVYACEVTHQGLSSPV TKSFNRGEC | 127 |
| AB012 | $V_H$ | QVQLVQSGGGLVQPGGSLRLSCAASGFTHHSYWLHWVRQA PGKGLEWVSDISRLSPYTNYADSVKGRFTISRDNAKNTLYLQ LNSLRAEDTAMYYCARGMDARRMDYWGQGTLVTVSS | 79 |
| | H | QVQLVQSGGGLVQPGGSLRLSCAASGFTHHSYWLHWVRQA PGKGLEWVSDISRLSPYTNYADSVKGRFTISRDNAKNTLYLQ LNSLRAEDTAMYYCARGMDARRMDYWGQGTLVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSCDKTHTCPPCPAPEAAGGPSVFLFPPKPKD TLMISRTPEVTCVVVSVSHEDPEVKFNWYVDGVEVHNAKTK PREEQYNSTYRVVSVLTVLHQDWLNGKEYKCKVSNKALPAP IEKTISKAKGQPREPQVYTLPPSRDELTKNQVSLTCLVKGFYP SDIAVEWESNGQPENNYKTTPPVLDSDGSFFLYSKLTVDKSR WQQGNVFSCSVLHEALHSHYTQKSLSLSPGK | 113 |
| | $V_L$ | DIQLTQSPSSVSVSVGERVTIDCTGSSSNIGGGYVVHWYQQKP GQAPQLLIYRNNQRPSGVPDRFSGSKSGTDATLTISSLQAEDA AVYYCAAWDDERNGWLFGQGTKLEIK | 94 |
| | L | DIQLTQSPSSVSVSVGERVTIDCTGSSSNIGGGYVVHWYQQKP GQAPQLLIYRNNQRPSGVPDRFSGSKSGTDATLTISSLQAEDA AVYYCAAWDDERNGWLFGQGTKLEIKRTVAAPSVFIFPPSDE QLKSGTASVVCLLNNFYPREAKVQWKVDNALQSGNSQESVT EQDSKDSTYSLSSTLTLSKADYEKHKVYACEVTHQGLSSPVT KSFNRGEC | 128 |

TABLE 5-continued

Sequences of Exemplary Anti-PRLR Antibodies

| Description | | Sequence | SEQ ID NO |
|---|---|---|---|
| AB013 | $V_H$ | QVQLVQSGGGLVQPGGSLRLSCAASGFSYSDYWMHWVRQA<br>PGKGLEWVSDISRLSPYTNYADSVKGRFTISRDNAKNTLYLQ<br>LNSLRAEDTAMYYCARGLDARRMSYWGQGTLVTVSS | 80 |
| | H | QVQLVQSGGGLVQPGGSLRLSCAASGFSYSDYWMHWVRQA<br>PGKGLEWVSDISRLSPYTNYADSVKGRFTISRDNAKNTLYLQ<br>LNSLRAEDTAMYYCARGLDARRMSYWGQGTLVTVSSASTK<br>GPSVFPLAPSSKSTSGGTAALGCLVKDYFPEPVTVSWNSGALT<br>SGVHTFPAVLQSSGLYSLSSVVTVPSSSLGTQTYICNVNHKPS<br>NTKVDKKVEPKSCDKTHTCPPCPAPEAAGGPSVFLFPPKPKD<br>TLMISRTPEVTCVVVSVSHEDPEVKFNWYVDGVEVHNAKTK<br>PREEQYNSTYRVVSVLTVLHQDWLNGKEYKCKVSNKALPAP<br>IEKTISKAKGQPREPQVYTLPPSRDELTKNQVSLTCLVKGFYP<br>SDIAVEWESNGQPENNYKTTPPVLDSDGSFFLYSKLTVDKSR<br>WQQGNVFSCSVLHEALHSHYTQKSLSLSPGK | 114 |
| | $V_L$ | DIQLTQSPSSVSVSVGERVTIDCTGSSSNIGAGYVVHWYQQKP<br>GQAPQLLIYRNNQRPSGVPDRFSGSKSGTDATLTISSLQAEDA<br>AVYYCAAHDDELHGWLFGQGTKLEIK | 95 |
| | L | DIQLTQSPSSVSVSVGERVTIDCTGSSSNIGAGYVVHWYQQKP<br>GQAPQLLIYRNNQRPSGVPDRFSGSKSGTDATLTISSLQAEDA<br>AVYYCAAHDDELHGWLFGQGTKLEIKRTVAAPSVFIFPPSDE<br>QLKSGTASVVCLLNNFYPREAKVQWKVDNALQSGNSQESVT<br>EQDSKDSTYSLSSTLTLSKADYEKHKVYACEVTHQGLSSPVT<br>KSFNRGEC | 129 |
| AB0014 | $V_H$ | QVQLVQSGGGLVQPGGSLRLSCAASGFTHHSYWLHWVRQA<br>PGKGLEWVSDISRLSPYTNYADSVKGRFTISRDNAKNTLYLQ<br>LNSLRAEDTAMYYCARGMDARRMDYWGQGTLVTVSS | 81 |
| | H | QVQLVQSGGGLVQPGGSLRLSCAASGFTHHSYWLHWVRQA<br>PGKGLEWVSDISRLSPYTNYADSVKGRFTISRDNAKNTLYLQ<br>LNSLRAEDTAMYYCARGMDARRMDYWGQGTLVTVSSASTK<br>GPSVFPLAPSSKSTSGGTAALGCLVKDYFPEPVTVSWNSGALT<br>SGVHTFPAVLQSSGLYSLSSVVTVPSSSLGTQTYICNVNHKPS<br>NTKVDKKVEPKSCDKTHTCPPCPAPEAAGGPSVFLFPPKPKD<br>TLMISRTPEVTCVVVSVSHEDPEVKFNWYVDGVEVHNAKTK<br>PREEQYNSTYRVVSVLTVLHQDWLNGKEYKCKVSNKALPAP<br>IEKTISKAKGQPREPQVYTLPPSRDELTKNQVSLTCLVKGFYP<br>SDIAVEWESNGQPENNYKTTPPVLDSDGSFFLYSKLTVDKSR<br>WQQGNVFSCSVLHEALHSHYTQKSLSLSPGK | 115 |
| | $V_L$ | DIQLTQSPSSVSVSVGERVTIDCTGSSSNIHGGYVVHWYQQKP<br>GQAPQLLIYRNNQRPSGVPDRFSGSKSGTDATLTISSLQAEDA<br>AVYYCAAWDDSRNGWLFGQGTKLEIK | 96 |
| | L | DIQLTQSPSSVSVSVGERVTIDCTGSSSNIHGGYVVHWYQQKP<br>GQAPQLLIYRNNQRPSGVPDRFSGSKSGTDATLTISSLQAEDA<br>AVYYCAAWDDSRNGWLFGQGTKLEIKRTVAAPSVFIFPPSDE<br>QLKSGTASVVCLLNNFYPREAKVQWKVDNALQSGNSQESVT<br>EQDSKDSTYSLSSTLTLSKADYEKHKVYACEVTHQGLSSPVT<br>KSFNRGEC | 130 |

B. Nucleic Acids and Host Cells Comprising Nucleic Acids Encoding Anti-Prolactin Receptor Antibodies In some aspects, the present disclosure provides nucleic acid or a set of nucleic acids, which collectively encodes any of the prolactin receptor antibodies disclosed here or any of the multi-specific antibodies or protein complexes as also disclosed herein. In some embodiments, the nucleic acid or the set of nucleic acids can be a vector or a set of vectors. In some examples, the vector is an expression vector. Further, provided herein is a host cell comprising any of the encoding nucleic acid or the set of nucleic acids as disclosed herein.

The present disclosure provides a method of producing an antibody binding to prolactin receptor or a multi-specific antibody or protein complex comprising such, comprising: (i) culturing the host cell comprising nucleic acid(s) encoding the prolactin receptor antibody as disclosed herein under conditions allowing for expression of the antibody that binds prolactin receptor; and (ii) harvesting the antibody thus produced from the cell culture.

The details of one or more embodiments of the invention are set forth in the description below. Other features or advantages of the present invention will be apparent from the following drawings and detailed description of several embodiments, and from the appended claims.

C. Pharmaceutical Compositions

Any of the anti-prolactin receptor antibodies disclosed herein can be used for therapeutic, diagnostic, and/or research purposes, all of which are within the scope of the present disclosure.

The antibodies as well as the encoding nucleic acids or nucleic acid sets, vectors comprising such, or host cells comprising the vectors, as described herein can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof "Sequence identity" refers to the extent to which two optimally aligned polynucleotides or polypeptide sequences are invariant throughout a window of alignment of components, e.g., nucleotides or amino acids. "Identity" can be readily calculated by known methods including, but not limited to, those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991).

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and can comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™ PLURONICS™ or polyethylene glycol (PEG).

In some examples, the pharmaceutical composition described herein comprises liposomes containing the antibodies (or the encoding nucleic acids) which can be prepared by methods known in the art, such as described in Epstein, et al., *Proc. Natl. Acad. Sci. USA* 82:3688 (1985); Hwang, et al., *Proc. Natl. Acad. Sci. USA* 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The antibodies, or the encoding nucleic acid(s), can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition can be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients can be added, for example mannitol or other pharmaceutically acceptable vehicles, if necessary.

Suitable emulsions can be prepared using commercially available fat emulsions, such as Intralipid™, Liposyn™, Infonutrol™, Lipofundin™ and Lipiphysan™. The active ingredient can be either dissolved in a pre-mixed emulsion composition or alternatively it can be dissolved in an oil (e.g., soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients can be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 μm and 0.5 μm, and have a pH in the range of 5.5 to 8.0.

The emulsion compositions can be those prepared by mixing an antibody with Intralipid™ or the components thereof (e.g., soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions can contain suitable pharmaceutically acceptable excipients as set out above. In some embodiments, the compositions are administered by the oral or nasal respiratory route for local or systemic effect.

Compositions in preferably sterile pharmaceutically acceptable solvents can be nebulized by use of gases. Nebulized solutions can be breathed directly from the nebulizing device, or the nebulizing device can be attached to a face mask, tent or intermittent positive pressure breathing machine. Solution, suspension, or powder compositions can be administered, preferably orally or nasally, from devices which deliver the formulation in an appropriate manner.

In some embodiments, the pharmaceutical composition provided herein may comprise any of the exemplary anti-PRLR antibodies (e.g., clones AB001, AB005, AB007, AB008, AB009, AB012, or AB013) and a buffer comprising N-acetylhistidine at pH 5.5 without sodium chloride.

II. Preparation of Anti-PRLR Antibodies

Any of the anti-PRLR antibodies disclosed herein can be prepared by conventional methods and/or methods provided herein. In some embodiments, the anti-prolactin receptor antibody disclosed herein can be prepared by recombinant technology as exemplified below.

Nucleic acids encoding the heavy and light chain of an anti-prolactin receptor antibody as described herein can be cloned into one expression vector, each nucleotide sequence being in operable linkage to a suitable promoter. In one example, each of the nucleotide sequences encoding the heavy chain and light chain or the multiple polypeptides is in operable linkage to a distinct prompter. Alternatively, the encoding nucleotide sequences can be in operable linkage with a single promoter, such that both heavy and light chains are expressed from the same promoter. When necessary, an internal ribosomal entry site (IRES) can be inserted between the heavy chain and light chain encoding sequences.

In some examples, the nucleotide sequences encoding the two or more chains of the antibody are cloned into two or more vectors, which can be introduced into the same or different cells. When the two or more chains are expressed in different cells, each of them can be isolated from the host cells expressing such and the isolated multiple chains can be mixed and incubated under suitable conditions allowing for the formation of the antibody.

Generally, a nucleic acid sequence encoding one or all chains of an antibody can be cloned into a suitable expression vector in operable linkage with a suitable promoter using methods known in the art. For example, the nucleotide sequence and vector can be contacted, under suitable conditions, with a restriction enzyme to create complementarity ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. The selection of expression vectors/promoter would depend on the type of host cells for use in producing the antibodies.

A variety of promoters can be used for expression of the antibodies described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter, and the herpes simplex tk virus promoter.

Regulatable promoters can also be used. Such regulatable promoters include those using the lac repressor from *E. coli* as a transcription modulator to regulate transcription from lac operator-bearing mammalian cell promoters [Brown, M. et al., *Cell,* 49:603-612 (1987)], those using the tetracycline repressor (tetR) [Gossen, M., and Bujard, H., *Proc. Natl. Acad. Sci. USA* 89:5547-5551 (1992); Yao, F. et al., *Human Gene Therapy,* 9:1939-1950 (1998); Shockelt, P., et al., *Proc. Natl. Acad. Sci. USA,* 92:6522-6526 (1995)]. Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from *E. coli* can function as a transcriptional modulator to regulate transcription from lac operator-bearing mammalian cell promoters [M. Brown et al., *Cell,* 49:603-612 (1987); *Gossen and Bujard* (1992); M. Gossen et al., *Natl. Acad. Sci. USA,* 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., *Human Gene Therapy,* 10(16):1392-1399 (2003)). One particular advantage of this tetracycline inducible switch is that it does not require the use of a tetracycline repressor-mammalian cells transactivator or repressor fusion protein, which in some instances can be toxic to cells (Gossen et al., *Natl. Acad. Sci. USA,* 89:5547-5551 (1992); Shockett et al., *Proc. Natl. Acad. Sci. USA,* 92:6522-6526 (1995)), to achieve its regulatable effects.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

Examples of polyadenylation signals useful to practice the methods described herein include, but are not limited to, human collagen I polyadenylation signal, human collagen II polyadenylation signal, and SV40 polyadenylation signal.

One or more vectors (e.g., expression vectors) comprising nucleic acids encoding any of the antibodies can be introduced into suitable host cells for producing the antibodies. The host cells can be cultured under suitable conditions for expression of the antibody, or any polypeptide chain thereof. Such antibodies, or polypeptide chains thereof can be recovered by the cultured cells (e.g., from the cells or the culture supernatant) via a conventional method, e.g., affinity purification. If necessary, polypeptide chains of the antibody can be incubated under suitable conditions for a suitable period of time allowing for production of the antibody.

In some embodiments, methods for preparing an antibody described herein involve a recombinant expression vector that encodes both the heavy chain and the light chain of an anti-prolactin receptor antibody, as also described herein, and optionally chains of a second antibody and/or chain(s) of a cytokine. The recombinant expression vector can be introduced into a suitable host cell (e.g., a dhfr− CHO cell) by a conventional method, e.g., calcium phosphate-mediated transfection. Positive transformant host cells can be selected and cultured under suitable conditions allowing for the expression of the two or more polypeptide chains that form the antibody, which can be recovered from the cells or from the culture medium. When necessary, the two or more chains recovered from the host cells can be incubated under suitable conditions allowing for the formation of the antibody.

In one example, two recombinant expression vectors are provided, one encoding the heavy chain of the anti-prolactin receptor antibody and the other encoding the light chain of the anti-prolactin receptor antibody. Each of the two or more recombinant expression vectors can be introduced into a suitable host cell (e.g., dhfr− CHO cell) by a conventional method, e.g., calcium phosphate-mediated transfection. Alternatively, each of the expression vectors can be introduced into a suitable host cell. Positive transformants can be selected and cultured under suitable conditions allowing for the expression of the polypeptide chains of the antibody. When the two or more expression vectors are introduced into the same host cells, the antibody produced therein can be recovered from the host cells or from the culture medium. If necessary, the polypeptide chains can be recovered from the host cells or from the culture medium and then incubated under suitable conditions allowing for formation of the polypeptide chain in the proper configuration. When the two or more expression vectors are introduced into different host cells, each of them can be recovered from the corresponding host cells or from the corresponding culture media. The two or more polypeptide chains can then be incubated under suitable conditions for formation of the antibody.

Standard molecular biology techniques are used to prepare the recombinant expression vector, transfect the host cells, select for transformants, culture the host cells and recovery of the antibodies from the culture medium. For example, some antibodies can be isolated by affinity chromatography with a Protein A or Protein G coupled matrix.

Any of the nucleic acids encoding the heavy chain, the light chain, or both of an anti-prolactin receptor antibody as described herein, vectors (e.g., expression vectors) containing such; and host cells comprising the vectors are within the scope of the present disclosure.

Antibodies obtained following a method known in the art and/or described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In another example, epitope mapping can be used to determine the sequence, to which an antibody bind. The epitope can be a linear epitope, i.e., contained in a single stretch of amino acids, or a conformational epitope formed by a three-dimensional interaction of amino acids that cannot necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments can, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries).

There are a number of routine methods known in the art to identify and isolate antibodies capable of binding to the target antigens described herein, including phage display, yeast display, ribosomal display, or mammalian display technology. In some embodiments, mRNA display can be used for isolating anti-prolactin receptor antibodies. See Example 1 below.

III. Application of Anti-Prolactin Receptor Antibodies

Any of the anti-prolactin receptor antibodies can be used for therapeutic, diagnostic, and/or research purposes, all of which are within the scope of the present disclosure.

A. Therapeutic Applications

Any of the anti-prolactin receptor antibodies disclosed herein can be used for therapeutic, diagnostic, and/or research purposes, all of which are within the scope of the present disclosure.

To practice the method disclosed herein, an effective amount of the pharmaceutical composition described herein can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the antibodies as described herein can be aerosolized using a fluorocarbon formulation and a metered dose inhaler or inhaled as a lyophilized and milled powder.

Patient," "subject," or "subject in need thereof" can refer to a living organism suffering from or prone to a disease or condition that can be treated by the administration of a pharmaceutical composition as provided herein. Non-limiting examples include humans, other mammals, bovines, rats, mice, dogs, monkeys, goats, sheep, cows, deer, and other non-mammalian animals. In some embodiments, a patient is human.

The term "treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof. With regard to cancer, "treating" or "treatment" can refer to inhibiting or slowing neoplastic or malignant cell growth, proliferation, or metastasis, preventing or delaying the development of neoplastic or malignant cell growth, proliferation, or metastasis, or some combination thereof. With regard to a tumor, "treating" or "treatment" can include eradicating all or part of a tumor, inhibiting or slowing tumor growth and metastasis, preventing or delaying the development of a tumor, or some combination thereof.

Alleviating a target disease/disorder includes delaying the development or progression of the disease or reducing disease severity or prolonging survival. Alleviating the disease or prolonging survival does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that can be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

The subject to be treated by the methods described herein can be a mammal, more preferably a human. Mammals include, but are not limited to, farm animals, sport animals, pets, primates, horses, dogs, cats, mice, and rats. A human subject who needs the treatment can be a human patient having, at risk for, or suspected of having a target disease/disorder characterized by carrying prolactin receptor+disease cells. Examples of such target diseases/disorders include gastrointestinal tumor, leukemias and other hematological malignancies; hormone-responsive cancers such as breast cancer, prostate cancer, ovarian, and endometrial cancer; reproductive and gynecological disorders such as endometriosis and infertility; autoimmune and inflammatory disorder such as systemic lupus erythematosus and rheumatoid arthritis; dermatological conditions such as alopecia and psoriasis; metabolic disorders such as obesity and diabetes; pituitary adenomas, mammary hyperplasia; hyperprolactinemia; and cardiovascular disease.

Examples for cancer types include, but are not limited to, breast cancer, bladder cancer, ovary cancer, cervical cancer, pancreatic cancer, lung cancer, or head and neck cancer.

A subject having a target cancer can be identified by routine medical examination, e.g., laboratory tests, organ functional tests, CT scans, or ultrasounds. In some embodiments, the subject to be treated by the method described herein can be a human cancer patient who has undergone or is subjecting to an anti-cancer therapy, for example, chemotherapy, radiotherapy, immunotherapy, or surgery. A subject suspected of having any of such target disease/disorder might show one or more symptoms of the disease/disorder. A subject at risk for the disease/disorder can be a subject having one or more of the risk factors for that disease/disorder.

An effective amount refers to the amount of each active agent required to confer therapeutic effect on the subject, either alone or in combination with one or more other active agents. Determination of whether an amount of the antibody achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. For example, antibodies that are compatible with the human immune system, such as humanized antibodies or fully human antibodies, can be used to prolong half-life of the antibody and to prevent the antibody being attacked by the host's immune system. Frequency of administration can be determined and adjusted over the course of therapy, and is generally, but not necessarily, based on treatment and/or suppression and/or amelioration and/or delay of a target disease/disorder. Alternatively, sustained continuous release formulations of an antibody can be appropriate. Various formulations and devices for achieving sustained release are known in the art.

In one example, dosages for an antibody as described herein can be determined empirically in individuals who have been given one or more administration(s) of the antibody. Individuals are given incremental dosages of the agonist. To assess efficacy of the agonist, an indicator of the disease/disorder can be followed.

Generally, for administration of any of the antibodies such as described herein, an initial candidate dosage can be about 2 mg/kg. For the purpose of the present disclosure, a typical daily dosage might range from about any of 0.1 μg/kg to 3 μg/kg to 30 μg/kg to 300 μg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens can be useful, depending on the pattern of pharmacokinetic decay that the practitioner wishes to achieve. For example, dosing from one-four times a week is contemplated. In some embodiments, dosing ranging from about 3 μg/mg to about 2 mg/kg (such as about 3 μg/mg, about 10 μg/mg, about 30 μg/mg, about 100 μg/mg, about 300 μg/mg, about 1 mg/kg, and about 2 mg/kg) can be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

In some embodiments, for an adult patient of normal weight, doses ranging from about 0.3 to 5.00 mg/kg can be administered. In some examples, the dosage of the anti-prolactin receptor antibody such as described herein can be 10 mg/kg. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of an antibody such as described herein will depend on the specific antibody, antibodies, and/or non-antibody peptide (or compositions thereof) employed, the type and severity of the disease/disorder, whether the antibody is administered for preventive or therapeutic purposes, previous therapy, the patient's clinical history and response to the agonist, and the discretion of the attending physician. Typically, the clinician will administer an antibody, until a dosage is reached that achieves the desired result. In some embodiments, the desired result is an increase in anti-tumor immune response in the tumor microenvironment. Methods of determining whether a dosage resulted in the desired result would be evident to one of skill in the art. Administration of one or more antibodies can be continuous or intermittent, depending, for example, upon the recipient's physiological condition, whether the purpose of the administration is therapeutic or prophylactic, and other factors known to skilled practitioners. The administration of an antibody can be essentially continuous over a preselected period of time or can be in a series of spaced dose, e.g., either before, during, or after developing a target disease or disorder.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularly or intravitreally.

Injectable compositions can contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipient is infused. Physiologically acceptable excipients can include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an antibody is administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., *Trends Biotechnol.* 11:202; Chiou et al. (1993), Gene Therapeutics: Methods And Applications Of Direct Gene Transfer (J. A. Wolff, ed.) (1994); Wu et al., *J Biol. Chem.* 263:621 (1988); Wu et al., *J Biol. Chem.* 269:542 (1994); Zenke et al., *Proc. Natl. Acad. Sci. USA* 87:3655 (1990); Wu et al., *J. Biol. Chem.* 266:338 (1991).

Therapeutic compositions containing a polynucleotide (e.g., those encoding the antibodies described herein) are administered in a range of about 100 ng to about 200 mg of DNA for local administration in a gene therapy protocol. In some embodiments, concentration ranges of about 500 ng to about 50 mg, about 1 μg to about 2 mg, about 5 μg to about 500 μg, and about 20 μg to about 100 μg of DNA or more can also be used during a gene therapy protocol.

The therapeutic polynucleotides and polypeptides described herein can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, *Hum. Gene Ther*. (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther*. (1992) 3:147); ligand-linked DNA (see, e.g., Wu, *J. Biol. Chem*. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, *Mol. Cell. Biol*. (1994) 14:2411, and in Woffendin, *Proc. Natl. Acad. Sci*. (1994) 91:1581.

The particular dosage regimen, i.e., dose, timing and repetition, used in the method described herein will depend on the particular subject and that subject's medical history.

In some embodiments, more than one antibody, or a combination of an antibody and another suitable therapeutic agent, can be administered to a subject in need of the treatment. The antibody can also be used in conjunction with other agents that serve to enhance and/or complement the effectiveness of the agents.

In some embodiments, the treatment methods provided herein is for modulating cell signaling medicated by the PRLR. As shown herein, the anti-PRLR antibodies disclosed herein are capable of engaging PRLR on cells, thereby modulating the downstream signaling mediated by the PRLR receptor. Such a treatment method can also benefit treatment of diseases associated with PRLR.

In some instances, the subject for treatment by the method disclosed herein can be a human patient having the disease associated with PRLR. Exemplary diseases associated with PRLR include, but are not limited to, cancer (e.g., gastrointestinal tumor, leukemias and other hematological malignancies; hormone-responsive cancers such as breast cancer, prostate cancer, ovarian, and endometrial cancer, pituitary adenomas, and mammary hyperplasia), reproductive and gynecological disorders (e.g., endometriosis and infertility), autoimmune and inflammatory disorder (e.g., systemic lupus erythematosus and rheumatoid arthritis), dermatological conditions (e.g., alopecia and psoriasis), metabolic disorders (e.g., obesity and diabetes), hyperprolactinemia, and cardiovascular disease.

In some embodiments, provided herein is a method for treating androgenetic alopecia comprising administering an effective amount of an anti-PRLR antibody as disclosed herein to a subject in need thereof. Androgenetic alopecia is a genetic condition that causes progressive hair loss on the scalp after puberty. In some examples, the subject can be a human patient having androgenetic alopecia. In other examples, the subject can be a human patient suspected of having the disease (for example, showing some symptoms associated with the disease). In other examples, the subject can be a human patient at risk for the disease (for example, carrying the genetic condition that causes the disease). Any of the anti-PRLR antibodies disclosed herein can be used in the treatment method. Examples include AB001, AB005, AB007, AB008, AB009, B012, or AB013 or a functional equivalent thereof (e.g., having the same heavy chain and light chain CDRs as those in any of the referenced anti-PRLR antibodies or having the same VH and VL chains as the referenced antibody). In one example, AB001 can be used in treating androgenetic alopecia. In another example, AB007 can be used in treating the disease. In yet another example, AB012 can be used in treating the disease. In other examples, any of the functional variants of AB001 as disclosed herein can be used in treating the disease.

In some embodiments, provided herein is a method for treating endometriosis comprising administering an effective amount of an anti-PRLR antibody as disclosed herein to a subject in need thereof. Endometriosis is a chronic condition where tissue similar to the lining of the uterus grows outside of the uterus. It can cause pelvic pain, heavy or painful period, and making it difficult to get pregnant. In some examples, the subject can be a human patient having endometriosis. In other examples, the subject can be a human patient suspected of having the disease (for example, showing some symptoms associated with the disease). In other examples, the subject can be a human patient at risk for the disease (for example, carrying one or more risk factors associated with the disease). Any of the anti-PRLR antibodies disclosed herein can be used in the treatment method. Examples include AB001, AB005, AB007, AB008, AB009, B012, or AB013 or a functional equivalent thereof (e.g., having the same heavy chain and light chain CDRs as those in any of the referenced anti-PRLR antibodies or having the same VH and VL chains as the referenced antibody). In one example, AB001 can be used in treating endometriosis. In another example, AB007 can be used in treating the disease. In yet another example, AB012 can be used in treating the disease. In other examples, any of the functional variants of AB001 as disclosed herein can be used in treating the disease.

In some embodiments, provided herein is a method for restoring hair color in a subject, comprising administering to a subject in need thereof an effective amount of an anti-PRLR antibody. In some examples, the subject can be a human patient having hair turning white. In some examples, one of the anti-PRLR antibodies disclosed herein can be used in the treatment method. Examples include AB001, AB005, AB007, AB008, AB009, B012, or AB013 or a functional equivalent thereof (e.g., having the same heavy chain and light chain CDRs as those in any of the referenced anti-PRLR antibodies or having the same VH and VL chains as the referenced antibody). In one example, AB001 can be used for restoring hair color. In another example, AB007 can be used for restoring hair color. In yet another example, AB012 can be used for restoring hair color. In other examples, any of the functional variants of AB001 as disclosed herein can be used for restoring hair color.

Treatment efficacy for a target disease/disorder can be assessed by methods well-known in the art.

B. Diagnostic Applications

Any of the anti-prolactin receptor antibodies disclosed here can be used for detecting and quantifying prolactin receptor levels or prolactin receptor+cell levels in a biological sample using a conventional method, for example, any immunohistological method known to those of skill in the art (see, e.g., Jalkanen, et al., *J. Cell. Biol.* 101:976-985 (1985); Jalkanen et al., *J. Cell Biol.* 105:3087-3096 (1987)). Other antibody-based methods useful for detecting prolactin receptor expression include immunoassays, such as the enzyme linked immunosorbent assay (ELISA), immunoprecipitation, or Western blotting. Suitable assays are described in more detail elsewhere herein.

A biological sample can be obtained from an individual, cell line, tissue culture, or other source of cells potentially expressing prolactin receptor. Methods for obtaining tissue biopsies and body fluids from mammals are well known in the art.

To perform the method disclosed herein, any of the anti-prolactin receptor antibodies as disclosed herein can be brought in contact with a sample suspected of containing a target antigen as disclosed herein, for example, a human prolactin receptor protein or a prolactin receptor+cell. In general, the term "contacting" or "in contact" refers to an exposure of the anti-prolactin receptor antibody disclosed herein with the sample suspected of containing the target antigen for a suitable period under suitable conditions sufficient for the formation of a complex between the anti-prolactin receptor antibody and the target antigen in the sample, if any. The antibody-antigen complex thus formed, if any, can be determined via a routine approach. Detection of such an antibody-antigen complex after the incubation is indicative of the presence of the target antigen in the sample. When needed, the amount of the antibody-antigen complex can be quantified, which is indicative of the level of the target antigen in the sample.

In some examples, the anti-prolactin receptor antibodies as described herein can be conjugated to a detectable label, which can be any agent capable of releasing a detectable signal directly or indirectly. The presence of such a detectable signal or intensity of the signal is indicative of presence or quantity of the target antigen in the sample. Alternatively, a secondary antibody specific to the anti-prolactin receptor antibody or specific to the target antigen can be used in the methods disclosed herein. For example, when the anti-prolactin receptor antibody used in the method is a full-length antibody, the secondary antibody can bind to the constant region of the anti-prolactin receptor antibody. In other instances, the secondary antibody can bind to an epitope of the target antigen that is different from the binding epitope of the anti-prolactin receptor antibody. Any of the secondary antibodies disclosed herein can be conjugated to a detectable label.

Any suitable detectable label known in the art can be used in the assay methods described herein. In some embodiments, a detectable label can be a label that directly releases a detectable signal. Examples include a fluorescent label or a dye. A fluorescent label comprises a fluorophore, which is a fluorescent chemical compound that can re-emit light upon light excitation. Examples of fluorescent label include, but are not limited to, xanthene derivatives (e.g., fluorescein, rhodamine, Oregon green, eosin, and Texas red), cyanine derivatives (e.g., cyanine, indocarbocyanine, oxacarbocyanine, thiacarbocyanine, and merocyanine), squaraine derivatives and ring-substituted squaraines (e.g., Seta and Square dyes), squaraine rotaxane derivatives such as SeTau dyes, naphthalene derivatives (e.g., dansyl and prodan derivatives), coumarin derivatives, oxadiazole derivatives (e.g., pyridyloxazole, nitrobenzoxadiazole and benzoxadiazole), anthracene derivatives (e.g., anthraquinones, including DRAQ5, DRAQ7 and CyTRAK Orange), pyrene derivatives such as cascade blue, oxazine derivatives (e.g., Nile red, Nile blue, cresyl violet, and oxazine 170), acridine derivatives (e.g., proflavin, acridine orange, and acridine yellow), arylmethine derivatives (e.g., auramine, crystal violet, and malachite green), and tetrapyrrole derivatives (e.g., porphin, phthalocyanine, and bilirubin). A dye can be a molecule comprising a chromophore, which is responsible for the color of the dye. In some examples, the detectable label can be fluorescein isothiocyanate (FITC), phycoerythrin (PE), biotin, Allophycocyanin (APC) or Alexa Fluor® 488.

In some embodiments, the detectable label can be a molecule that releases a detectable signal indirectly, for example, via conversion of a reagent to a product that directly releases the detectable signal. In some examples, such a detectable label can be an enzyme (e.g., β-galactosidase, HRP or AP) capable of producing a colored product from a colorless substrate.

In addition, any of the anti-PRLR antibodies disclosed herein can also be used in a non-clinical setting, for example, in laboratory researches for detecting and/or quantifying the target antigen PRLR in samples suspected of containing such.

C. Kits for Use in Treatment or Diagnosis of Diseases

The present disclosure also provides kits for use in treating or alleviating a target disease, such as those provided herein, or for use in diagnosing such diseases. Such kits can include one or more containers comprising an anti-prolactin receptor antibody described herein. In some instances, the anti-prolactin receptor antibody can be co-used with a second therapeutic agent.

In some embodiments, the kit can comprise instructions for use in accordance with any of the methods described herein. The included instructions can comprise a description of administration of the anti-prolactin receptor antibody and optionally the second therapeutic agent, to treat, delay the onset, or alleviate a target disease as those described herein. The kit can further comprise a description of selecting an individual suitable for treatment based on identifying whether that individual has the target disease, e.g., applying the diagnostic method as described herein. In still other embodiments, the instructions comprise a description of administering an antibody to an individual at risk of the target disease.

The instructions relating to the use of an anti-prolactin receptor antibody generally include information as to dosage, dosing schedule, and route of administration for the intended treatment. The containers can be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating the disease, such as cancer. Instructions can be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit can have a sterile access port (for example the container can be an intravenous solution bag or a vial having a stopper pierceable by a hypodermic injection needle). The container can also have a sterile access port (for example the container can be an intravenous solution bag or a vial having a stopper pierceable by a hypodermic injection needle). At least one active agent in the composition is an anti-prolactin receptor antibody such as those described herein.

Kits can optionally provide additional components such as buffers and interpretive information. Normally, the kit comprises a container and a label or package insert(s) on or associated with the container. In some embodiments, the present disclosure provides articles of manufacture comprising contents of the kits described above.

In some embodiments, the kit provided herein is for diagnostic purposes. Such a kit may further comprise detecting agents, in addition to the anti-PRLR antibody, for detecting binding of the antibody to the target antigen and/or for measuring the level of such bindings. The kit may further include information for performing the diagnostic assay with any of the anti-PRLR antibodies provided herein.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as Molecular Cloning: A Laboratory Manual, second edition (Sambrook, et al., 1989) Cold Spring Harbor Press; Oligonucleotide Synthesis (M. J. Gait, ed. 1984); Methods in Molecular Biology, Humana Press; Cell Biology: A Laboratory Notebook (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al., eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); DNA Cloning: A practical Approach, Volumes I and II (D. N. Glover ed. 1985); Nucleic Acid Hybridization (B. D. Hames & S. J. Higgins eds. (1985; Transcription and Translation (B. D. Hames & S. J. Higgins, eds. (1984; Animal Cell Culture (R. I. Freshney, ed. (1986; Immobilized Cells and Enzymes (IRL Press, (1986; and B. Perbal, A practical Guide To Molecular Cloning (1984); F. M. Ausubel et al., (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

These examples are provided for illustrative purposes only and not to limit the scope of the claims provided herein.

Example 1. Designing Exemplary Anti-PRLR Antibodies with Improved Features by AI Modeling This example describes an exemplary approach for designing exemplary antibodies that bind human prolactin receptor (PRLR) from parent anti-PRLR antibody AB000 using Artificial Intelligence (AI) model trained with datasets generated from high- or low-throughput assays. The structural information of the parent clone AB000 is provided above. The exemplary anti-PRLR antibodies derived from AB000 as disclosed herein exhibit improved features such as high binding affinity, solubility, stability, or a combination thereof as compared with AB000.

The heavy chain and light chain complementarity determining regions (CDRs) of AB000 were grafted into IGHV3-66*01 and IGKV4-1*01 germline framework regions (FRs) respectively. AI models were used for designing variations in both CDRs and FRs for improving antibody features such as PRLR binding affinity, solubility, stability, or a combination thereof.

Briefly, training datasets for AI models were generated using either a high throughput ACE assay or lower throughout SPR assay. After dataset generation, high throughput ACE assays were validated against SPR for assay validation. For the heavy chain, datasets were generated at multiple pHs to design datasets for conferring pH sensitivity. For both heavy and light chains, a suite of models were generated depending on dataset size and data quality. Some examples of models include fine-tuned pre-trained protein language models on top of amino acid sequences. Other instances include polynomial feature embedding of the mutated amino acid followed by a linear ridge regression model. After model training, many possible heavy and light chains were screened in silico via the models and top predictions were validated in the lab. Post validation, a subset of heavy and light chains was combined to generate a combinatorial dataset for a second round of modeling. The predictions from this second round of modeling were validated in vitro prior to selection of the final lead test candidates. More details of the AI modeling approach can be found in WO2023133462 and WO024040020, the relevant disclosures of each of which are incorporated by reference for the subject matter and purpose referenced herein. Exemplary clones AB001-AB014 were generated using the AI modeling approach. Structural features of these exemplary anti-PRLR antibodies are provided above. Characterization of their bioactivity and developability is provided in Examples below.

Example 2. Characterization of Exemplary Anti-PRLR Antibodies to Species-Specific PRLR This example describes assessments of exemplary anti-PRLR antibodies' binding affinity and estimates binding kinetics of PRLR antigens from various species, including human, cynomolgus, and mouse. Characterizing the affinity and species cross reactivity of an antibody to its target is critical to informing the preclinical development of a biologic. This example also describes assessments of solubilities of the exemplary anti-PRLR antibodies.

All experimental monoclonal antibodies (mAbs) were produced in a CHO-K1 expression system. Samples were purified via protein A affinity chromatography purification, further purified by size exclusion chromatography (SEC), and kept in a storage buffer. Concentration of mAbs was determined by A280 using the SoloVPE instrument (Repligen). Suitable protein quality was confirmed by SEC, reduced capillary gel electrophoresis (CGE) or non-reduced CGE (NR-CGE), imaging capillary isoelectric focusing (icIEF), and intact mass spectrometry after deglycosylation. For aggregation determination, SEC was performed using 1×PBS, pH 7.4 as a mobile phase and a 30 cm column TSKgel UP-SW2000 (Tosoh). To evaluate fragmentation, NR-CGE was performed with SDS-MW Analysis Kit (Sciex) together with the SDS sample buffer with iodoacetamide; the separation method was performed using the high-speed setup. When CGE was performed under reducing conditions, 5% (v/v) 2-mercaptoethanol was added to the SDS sample buffer, and the separation method was also performed using high-speed setup. Charge distribution and pI of the candidates were determined by icIEF using the Maurice system (Protein Simple). Samples were prepared by mixing 1:9 (v:v) of 1.0 mg/mL mAb samples and the following master mix: 0.35% (v/v) 1% methylcellulose, 2 M urea, 4% (v/v) Pharmalyte® 3-10 (Cytiva), 0.5% (v/v) pI marker 4.05 (Protein Simple), 0.5% (v/v) pI marker 9.99 (Protein Simple), and 10 mM arginine.

A. Binding Affinity to PRLR of Various Species

The antigen binding affinity of the exemplary antibodies was measured by surface plasmon resonance (SPR), a preferred method that allows for estimation of the kinetic parameters $k_{on}$ and $k^{off}$ as well as the dissociation constants (KD). Briefly, high-throughput SPR experiments were conducted on a Carterra LSA SPR Instrument using SPR running buffer (10 mM HEPES, 150 mM NaCl, 3 mM EDTA, 0.05% w/v Tween-20, 0.5 mg/mL BSA, pH 7.4; 1×PBS, 3 mM EDTA, 0.05% w/v Tween-20, 0.5 mg/mL BSA, pH 5.8) and SPR wash buffer (10 mM HEPES, 150 mM NaCl, 3 mM EDTA, 0.05% w/v Tween-20 pH 7.4; 1×PBS, 3 mM EDTA, 0.05% w/v Tween-20, pH 5.8). Carterra SAHC30M chips were functionalized with 10 ug/mL biotinylated kappa light chain antibody capture reagent and 10 μg/mL biotinylated lambda light chain antibody capture reagent for 600 seconds prior to conducting experiments.

Samples were immobilized onto chip surfaces for 600 seconds followed by a 30 second washout step for baseline stabilization. Antigen binding was conducted using a 300 second association phase followed by a 600 second dissociation phase. Six leading blanks of SPR running buffer were injected to create a consistent baseline prior to monitoring antigen binding kinetics. After the leading blanks, six concentrations of Human FcRn/FCGRT&B2M Heterodimer Protein (ACRO Biosystems, three-fold serial dilutions from 1000 nM) were injected. Four replicates were tested per clone.

For measuring binding kinetics of the antibodies by SPR, Protein A/G sensor chips were used to immobilize mAb samples via binding to the Fc region and the Fab arms were subsequently probed with a 6-point 2-fold serial dilution of test candidates injected as the analyte with concentration ranging from 1.56-50 nM. Assays were run in buffer solutions that were adjusted to pH 7.4 and pH 5.8 to measure binding affinities at both conditions. Kinetic parameters $k_{on}$, $k_{off}$, of test candidate binding to the immobilized IgGs were estimated from non-linear regression analysis and dissociation constants (KD) were calculated for each immobilized IgG1. Tables 6-8 show that certain exemplary anti-PRLR antibodies designed as described in Example 1 showed enhanced binding affinity to human PRLR with cross-reactivity to cynomolgus and mouse PRLR.

TABLE 6

Binding Affinities (KD) of Exemplary Anti-PRLR Antibodies to Human PRLR

| Name | Average $K_D$/ SD (nM) at pH 7.4 | Average $K_D$/ SD (nM) at pH 5.8 | Number of replicate measurements |
|---|---|---|---|
| AB001 | 0.42 (0.15) | 0.21 (0.03) | 4 |
| AB012 | 2.19 (0.33) | 3.14 (0.51) | 4 |
| AB007 | 0.41 (0.15) | 1.10 (0.18) | 4 |
| AB005 | 0.30 (0.02) | 0.29 (0.04) | 4 |
| AB009 | 1.16 (0.26) | 10.05 (1.84) | 4 |
| AB013 | 0.77 (0.16) | 2.16 (0.19) | 4 |
| AB000 | 3.03 (0.29) | 4.36 (0.56) | 4 |

TABLE 7

Binding Affinities (KD) of Exemplary Anti-PRLR Antibodies to Cynomolgus PRLR

| Name | Average $K_D$/ SD (nM) at pH 7.4 | Average $K_D$/ SD (nM) at pH 5.8 | Number of replicate measurements |
|---|---|---|---|
| AB001 | 0.30 (0.07) | 1.02 (0.09) | 4 |
| AB012 | 2.38 (0.56) | 5.72 (0.45) | 4 |
| AB007 | 0.37 (0.09) | 2.35 (0.08) | 4 |
| AB005 | 0.27 (0.07) | 0.20 (0.02) | 4 |
| AB009 | 1.49 (0.14) | 13.26 (1.32) | 4 |
| AB013 | 2.00 (0.53) | 7.47 (0.11) | 4 |
| AB000 | 9.38 (1.45) | 6.85 (0.84) | 4 |

TABLE 8

Binding Affinities (KD) of the Exemplary Anti-PRLR Antibodies to mouse PRLR

| Name | Average $K_D$/ SD (nM) at pH 7.4 | Average $K_D$/ SD (nM) at pH 5.8 | Number of replicate measurements |
|---|---|---|---|
| AB001 | 0.56 (0.09) | 2.22 (0.19) | 4 |
| AB012 | 0.85 (0.09) | 1.49 (0.07) | 4 |
| AB007 | 0.28 (0.08) | 2.71 (0.37) | 4 |
| AB005 | 0.24 (0.08) | 0.13 (0.02) | 4 |
| AB009 | 1.96 (0.37) | 10.34 (2.22) | 4 |
| AB013 | 0.43 (0.18) | 1.83 (0.23) | 4 |
| AB000 | 0.26 (0.02) | 1.040.11) | 4 |

B. Solubility of Exemplary Anti-PRLR Antibodies

To screen for the solubility of the monoclonal antibodies prepared as described herein, samples were prepared at 0.5 mg/mL in the presence of PEG from 8 to 22% and incubated overnight (18 hours) at 5±3 °C under gentle agitation. Precipitation onset was reported as the PEG percentage that induced a higher than 2-fold absorbance at 520 nm over samples that did not contain protein.

Three buffers (20 mM sodium phosphate at pH 7.0, 20 mM citrate at pH 6.0 and 20-mM histidine at pH 5.5) with and without 150 mM sodium chloride were used to identify the optimal pH and NaCl presence and absence for additional evaluations. PEG onset results demonstrated that all candidate antibodies had a much greater solubility in histidine pH 5.5 with no salt. The test candidates were then concentrated, and buffer exchanged into the highest solubility buffer (10 mM Histidine pH 5.5 with no salt) using a pPulse instrument from Formulatrix. Diffusion coefficient parameters were determined for all antibodies using the Prometheus Panta instrument and data processing software from NanoTemper. Samples were analyzed at 10.0, 8.0, 6.0, 4.0 and 2.0 mg/mL. The diffusion coefficient parameter represents the dependence of molecular diffusivity over different protein concentrations. When the diffusion interaction parameter coefficient is negative, it indicates a tendency for self-interaction, which is known to be a surrogate of viscosity at high concentrations1. The anti-PRLR lead candidates showed diffusion interaction parameters greater than the putative clinical competitor molecule with R2 values above 0.90. Connolly B D, et al., Biophys J., 103 (1):69-78 (2012).

Table 9 below shows the solubility results obtained from this study. In sum, the tested exemplary anti-PRLR antibodies are more soluble in histidine-Ac buffer at pH 5.5 without sodium chloride and are more soluble compared to the parent AB000 antibody in the same buffer.

°C/min. Prometheus Panta software v1.1 (Nanotemper) was used for data analysis. The exemplary anti-PRLR antibodies were comparable to the reference AB000 antibody in terms of self-association, non-specific binding, hydrophobicity, antibody/FcRn binding at a gradient of pH, melting temperature and size distribution as determined by dynamic light scattering.

To assess stability of the exemplary antibodies, a high concentration formulation of the exemplary anti-PRLR antibodies was prepared as follows. Briefly, 175 mg of antibody in storage buffer (20 mM His-acetate, 150 mM NaCl, pH 5.5) was concentrated by Tangential Flow filtration (TFF) with a Formulatrix pPulse holding a 30 kDa PES chip using the Concentration Auto Profile to a volume of 3 mL. Protein concentration of the retentate was confirmed to be >50 mg/mL by absorbance at A280. The retentate was buffer exchanged into formulation buffer (20 mM His-acetate, pH 5.5) on the Formulatrix pPulse using the Buffer Exchange Auto Profile and 10 diavolumes of formulation buffer. After buffer exchange, Polysorbate-80 was added to a final concentration of 0.05% v/v and the sample was sterile filtered through a 0.22 μm PES filter. The final protein concentration was determined by absorbance at A280.

TABLE 9

Solubility and Diffusion Coefficient of Exemplary Anti-PRLR Antibodies

| Sample | PEG Solubility % PEG Turbidity Onset | | | | | | Diffusion Coefficient Slope | | | |
|---|---|---|---|---|---|---|---|---|---|---|
| | Phosphate, pH 7.0 | | Citrate, pH 6.0 | | Histidine-Ac, pH 5.5 | | Histidine-Ac, pH 5.5 | | | |
| name | +Salt | −Salt | +Salt | −Salt | +Salt | −Salt | −Salt | $R^2$ | +Salt | $R^2$ |
| AB000 | 10 | ≤8 | 12 | 12 | 12 | 16 | 5.73 | 0.76 | −7.30 | 0.90 |
| AB001 | 10 | ≤8 | 14 | 12 | 14 | >22 | 22.60 | 0.97 | −4.56 | 0.79 |
| AB005 | 12 | 10 | 12 | 10 | 10 | 20 | 11.68 | 0.93 | −7.76 | 0.85 |
| AB007 | ≤8 | ≤8 | 12 | 10 | 14 | 22 | 20.16 | 0.98 | −5.69 | 0.82 |
| AB009 | 14 | 12 | 14 | 14 | 16 | >22 | 20.99 | 0.95 | −3.33 | 0.51 |
| AB012 | ≤8 | ≤8 | 14 | 12 | 14 | 20 | 13.38 | 0.94 | −5.77 | 0.81 |
| AB013 | 14 | 12 | 16 | 14 | 16 | 20 | 15.83 | 0.94 | −6.26 | 0.81 |

Example 3: Stability of Exemplary Anti-PRLR Antibodies

This example describes and assesses stability of exemplary anti-PRLR antibodies that bind to the human prolactin receptor (PRLR) compared to the parent anti-PRLR antibody AB000 by measuring self-interaction, polyspecificity, hydrophobicity.

Briefly, affinity capture-self interaction nanoparticle spectroscopy (AC-SINS), anti-insulin and anti-DNA ELISA, and hydrophobic interaction chromatography (HIC) were performed. FcRn chromatography was performed to assess predictive pharmacokinetics of the exemplary anti-PRLR antibodies. Briakinumab (Leinco Technologies, P/N LT500) and Herceptin (Genentech) were used as positive and negative controls, respectively. A cutoff of 2× background on polyspecificity was implemented. To assess particle size and melting temperature, Dynamic Light Scattering and nano Differential Scanning Fluorimetry (DLS/DSF) were performed using a Prometheus Panta (Nanotemper). Antibodies were diluted to 0.5 mg/mL using 1×PBS μLand spun down and loaded into Prometheus High Sensitivity Capillaries (Nanotemper). DLS measurements were taken at 25 °C under high sensitivity settings. Thermal denaturation was performed from 25 °C to 90 °C using a ramp rate of 0.5

Stability of the exemplary anti-PRLR antibodies were measured against the reference AB000 antibody. Time points were taken for heat stress at 50 °C, 4 °C, room temperature at 25 °C, and following multiple freeze thaw cycles. All antibodies showed similar stability compared to reference AB000 (Table 10). Further, acidic and basic stress timepoints were collected and size exclusion chromatography (SEC), Non-Reduced capillary gel-electrophoresis (NR-CGE) and icIEF (charge distribution) were performed to monitor changes in material quality. SEC testing showed nearly no changes in product quality. Changes in NR-CGE were analyzed for trends over time and were indicative of degradation. Trends for icIEF data were observed for acidic and basic conditions to determine changes to molecular charge distribution. Slopes for NR-CGE purity indicate mild susceptibility of one of the exemplary anti-PRLR antibody to heat stress (Table 11). Finally, scores of 1 (stable), 2 (mild changes), and 3 (large changes) and scores for each condition evaluated were summed and then divided by four (four conditions) to report a weighted forced degradation score (Table 12).

TABLE 10

Forced Degradation of Exemplary Anti-PRLR Antibodies under Different Temperatures and Freeze-and-Thaw Conditions

| Sample | 25° C. (% Main/day | | 4° C. (% Main/day) | | 50° C. (% Main/day) | | Freeze-Thaw (% Main/cycle) | |
|---|---|---|---|---|---|---|---|---|
| Name | Slope | $R^2$ | Slope | $R^2$ | Slope | $R^2$ | Slope | $R^2$ |
| AB000 | 0.3 | 0.55 | 0.4 | 0.09 | −0.1 | 0.04 | −0.3 | 0.44 |
| AB001 | 0.1 | 0.49 | −0.3 | 0.28 | 0.1 | 0.75 | 0.5 | 0.85 |
| AB005 | −0.4 | 0.10 | −0.1 | 0.10 | 0.1 | 0.79 | 0.4 | 0.94 |
| AB007 | −0.6 | 0.44 | 0.0 | 0.00 | 0.5 | 0.30 | 1.2 | 0.99 |
| AB009 | 1.6 | 0.85 | 0.0 | 0.00 | 0.6 | 0.32 | 0.7 | 0.90 |
| AB012 | 0.0 | 0.09 | 0.0 | 0.05 | −0.1 | 0.07 | −0.3 | 1.00 |
| AB013 | 0.2 | 0.35 | 0.2 | 0.27 | 0.0 | 0.11 | 0.0 | 0.16 |

TABLE 11

Slopes for NR-CGE Purity of Exemplary Anti-PRLR Antibodies

| | Acidic Stress (% Main/day) | | | | Basic Stress (% Main/day) | | | |
|---|---|---|---|---|---|---|---|---|
| Sample | NR-CGE, fragmentation | | icIEF, charge profile | | NR-CGE, fragmentation | | icIEF, charge profile | |
| name | Slope | $R^2$ | Slope | $R^2$ | Slope | $R^2$ | Slope | $R^2$ |
| AB000 | −0.8 | 0.44 | −2.9 | 0.68 | −1.5 | 0.44 | −11.8 | 0.71 |
| AB001 | −0.1 | 0.12 | −1.1 | 0.85 | −8.0 | 0.63 | −4.9 | 1.00 |
| AB005 | 0.1 | 0.79 | −0.9 | 1.00 | 1.2 | 0.48 | −2.7 | 1.00 |
| AB007 | −0.9 | 0.84 | −0.6 | 0.46 | −1.9 | 0.11 | −8.6 | 0.99 |
| AB009 | 1.0 | 0.38 | 0.2 | 0.36 | 3.2 | 1.00 | −4.2 | 0.93 |
| AB012 | −0.2 | 0.91 | 0.2 | 0.18 | −0.6 | 0.31 | −4.3 | 0.53 |
| AB013 | −0.3 | 0.89 | −2.2 | 0.83 | −0.5 | 0.82 | −6.5 | 0.62 |

TABLE 12

Scoring Analysis of the Exemplary Anti-PRLR Antibodies for Forced Degradation

| Sample name | Heat | FT | Acidic | Basic | Sum of scores | Weighted |
|---|---|---|---|---|---|---|
| AB000 | 0 | 1 | 2 | 3 | 6 | 1.5 |
| AB001 | 0 | 0 | 1 | 3 | 4 | 1 |
| AB005 | 0 | 0 | 1 | 1 | 2 | 0.5 |
| AB007 | 0 | 0 | 1 | 3 | 4 | 1 |
| AB009 | 0 | 0 | 0 | 2 | 2 | 0.5 |
| AB012 | 0 | 1 | 1 | 2 | 4 | 1 |
| AB013 | 0 | 0 | 2 | 2 | 4 | 1 |

Example 4. Binding Affinity of Exemplary Anti-PRLR Antibodies to Fc Receptors This example describes binding activities of the exemplary anti-PRLR antibodies to Fe receptors such as Fcγ receptors and FcRn. The mAbs are in IgG1 format comprising a heavy chain constant region with variations of L234A, L23 5A, D265 S, M428L, and N434S relative to the wild-type human IgG1 counterpart. The heavy chain and light chain constant region sequences of the mAbs tested here are provided in Tables 1 and 2 above.

A. Binding Activity to FcRn

The high affinity of FcRn for IgG Fc region at low pH, and low affinity at neutral pH, is central to its role in regulating and extending the serum half-lives of IgGs. Surface Plasmon Resonance (SPR) is a widely preferred method that allows estimating the kinetic parameters $k_{on}$ and $k_{off}$ of FcRn binding to test candidates and calculate dissociation constants (KD) for the test candidates at acidic (pH 5.8) and neutral (pH 7.4) pH.

The binding activities to FcRn by the exemplary anti-PRLR antibodies were measured by SPR as described in Example 2 above.

For measuring binding kinetics to the Fc region in IgG1 format, a biotinylated capture reagent on a streptavidin chip was used to immobilize mAbs via the two Fab arms, orienting the Fc region to be subsequently probed with a 6-point, 3-fold serial dilution of FcRn injected as the analyte starting at 1000 nM. The affinity at pH 7.4 was insufficient to yield too low to provide a meaningful average, but all measured values were consistently greater than 1 μM. Combined, the results indicate that the test candidates bind with nanomolar affinity at pH 5.8 and micromolar affinity at pH 7.4. See Table 13 below.

TABLE 13

Average KD Measurements for Exemplary Anti-PRLR Antibodies' Binding to FcRn at pH 5.8 and pH 7.4

| Name | $K_D$ at pH 7.4 | Average $K_D$/ SD (nM) at pH 5.8 | Number of replicate measurements |
|---|---|---|---|
| AB001 | >1000 nM | 8.03 (0.56) | 4 |
| AB012 | >1000 nM | 9.78 (0.58) | 4 |
| AB007 | >1000 nM | 9.80 (0.41) | 4 |
| AB005 | >1000 nM | 12.2 (0.85) | 4 |
| AB009 | >1000 nM | 9.32 (1.3) | 4 |
| AB013 | >1000 nM | 10.09 (0.86) | 4 |
| AB000 | No binding observed | 45.89 (0.12) | 4 |

B. Binding Activity to Fcγ Receptors

Binding affinity of the exemplary anti-PRLR antibodies to FcγRs was assessed by SPR as described in Example 1 above to evaluate silencing of the effector function.

To assess binding of the test candidates to FcγRs, a biotinylated capture reagent on a streptavidin chip was used to immobilize mAbs via the two Fab arms, orienting the Fc region to be subsequently probed with the analytes consisting of a panel of FcγR including FcγRI, FcγRII, and FcγRIII (ACRO Biosystems) at a single concentration of 1000 nM, with two buffer injections in between each association and dissociation phase to return to baseline. Four replicates were tested per clone. As shown in Table 14 below, the exemplary anti-PRLR antibodies exhibited no binding activity to the tested Fcγ receptors, similar to the IgG1 control with the L234A/L235A mutations, indicating that the effector function of the exemplary anti-PRLR antibodies was silenced.

then incubated for 18 hours at 37 °C with 5% $CO_2$. After overnight incubation, the supernatant from the culture was collected, the cells were washed twice with HSBS, and lysed in 60 μL of RIPA buffer. Supernatants (recycled antibody) and cell lysates (residual antibody) were serially diluted and assayed using a sandwich ELISA. Statistical analysis of the data was performed using Prism (GraphPad) software. The raw data were fitted to four-parameter logistic curves, and antibody concentrations were extrapolated from standard curves. The relative recycling, residual levels, and HERA scores were calculated using Herceptin as the control wild type. The HERA score was calculated as the ratio of relative recycling to relative residual antibody levels. Results indicate that several test candidates had a significantly higher HERA score compared to the clinical benchmark antibody (FIG. 1).

TABLE 14

Binary B Activity of Exemplary Anti-PRLR Antibodies to FcγRs.

| Sample Name | FcγRIIIB CD16b (NA1) | FcγRIIIA CD16A (V176) | FcγRIIIA CD16A (F176) | FcγRIIB/ CCD32b/c | FcγRIIA CD32a (R167) | FcγRIIA CD32a (H167) | FcγRI/ CD64 | # |
|---|---|---|---|---|---|---|---|---|
| AB000 IgG1 | N | Y | Y | Y | Y | Y | Y | 4 |
| AB000 IgG2 | N | N | N | N | Y | Y | Y | 4 |
| AB000 IgG1-LALAGR | N | N | N | N | N | N | N | 4 |
| AB001 | N | N | N | N | N | N | N | 4 |
| AB012 | N | N | N | N | N | N | N | 4 |
| AB007 | N | N | N | N | N | N | N | 4 |
| AB005 | N | N | N | N | N | N | N | 4 |
| AB009 | N | N | N | N | N | N | N | 4 |
| AB013 | N | N | N | N | N | N | N | 4 |

Key: “Y” indicates binding was observed, “N” indicates no binding was observed. “#” indicates number of replicate measurements.

Example 5. Assessing Endothelial Recycling of Exemplary Anti-PRLR Antibodies

This example describes assessment of anti-PRLR antibody recycling as a direct measure of their in vivo half-life.

Plasma half-life dramatically affects the therapeutic potential of a monoclonal antibody. Among many plasma proteins, immunoglobulins and human serum albumin (HSA) exhibit some of the longest half-lives. The recycling of immunoglobulins and HSA by endothelial cells through interaction with the neonatal fragment crystallizable receptor (FcRn) is a key process that mediates the long half-life of these proteins. the degree of an antibody’s recycling in an in vitro assay using immortalized human endothelial cells correlates well with the in vivo half-life of antibodies in FcRn transgenic mice.

To assess endothelial recycling, an immortalized human microvascular endothelial cell line, HMEC-1 (ATCC), was transduced with the human FcRn receptor using a lentiviral vector. The resulting cell line overexpressed the human FcRn receptor, as confirmed by qRT-PCR. Cells were plated in a standard tissue culture-treated 96-well plate at a density of 100,000 cells per well in 100 μL of growth medium and incubated overnight at 37 °C with 5% $CO_2$. The following morning, the growth medium was aspirated, and 400 nM of test antibodies were added in a volume of 100 μL of HSBS per well for 4 hours. After incubation, the cells were washed four times with 100 μL of HSBS, and 100 μL of growth medium without FBS was added to each well. The cells were

Example 6. Engagement of Anti-PRLR Antibodies with PRLR Receptor

This example describes the engagement and inhibition of signaling through prolactin receptor of the exemplary anti-PRLR antibodies by measuring downstream activity upon treatment with the anti-PRLR antibody using a commercially available PathHunter functional assay.

Engagement of prolactin (PRL) with the prolactin receptor (PRLR) on the surface of mammalian cells triggers the recruitment of JAK2 tyrosine kinase and STAT5 to the cytoplasmic region of PRLR, culminating in the phosphorylation and activation of STAT5. A commercially-available PathHunter Assay utilizes cells that overexpress a PRLR-enzyme fragment fusion. Upon PRL binding, the activation of the PRLR signaling cascade recruits another fragment of the enzyme to the PRLR fusion, forming an active enzyme. This enzyme’s activity in processing a chemiluminescent substrate is highly correlated with changes in PRLR signaling.

A. Engagement with PRLR Measured by PathHunter Assay

Figure 2:
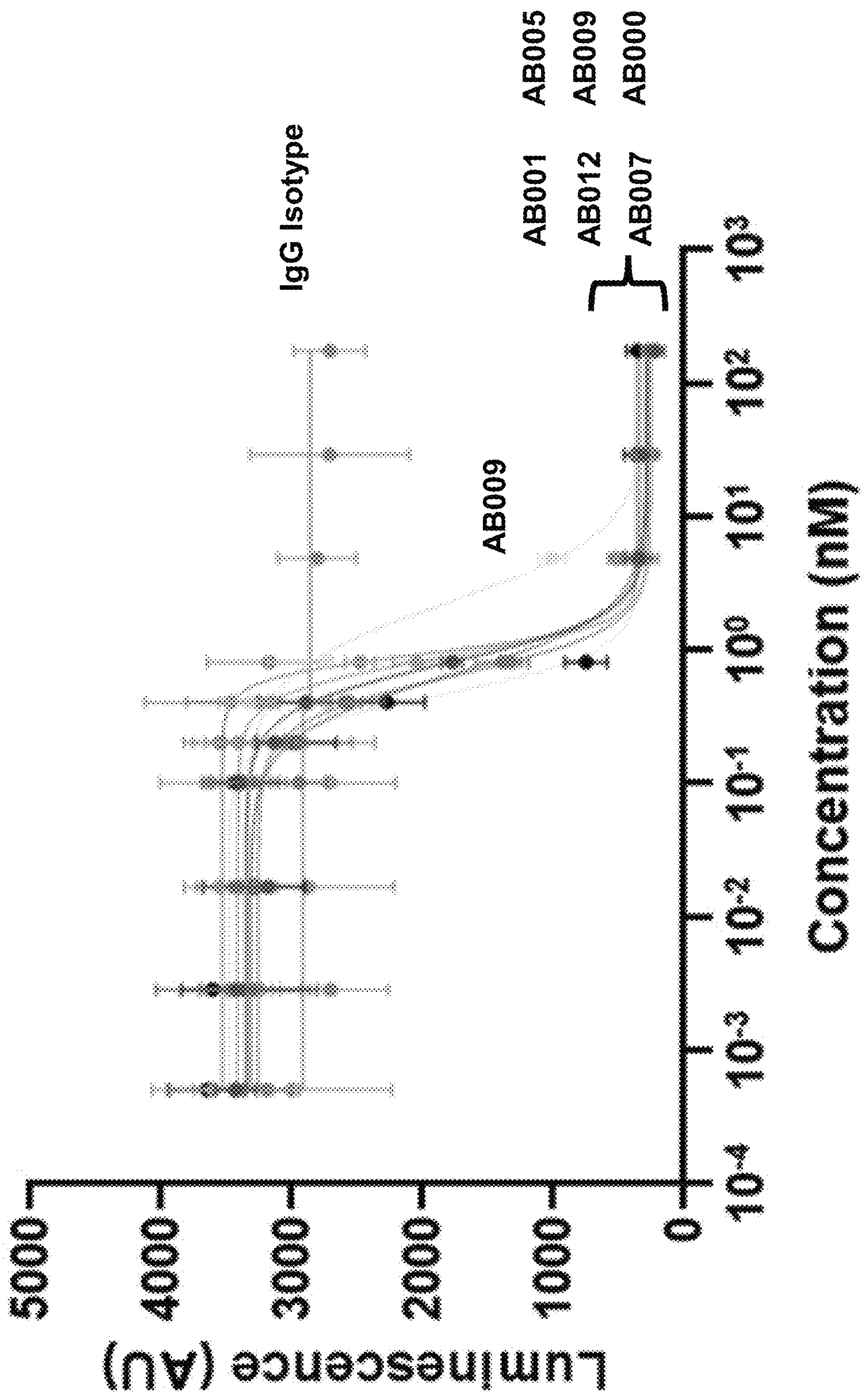
FIG. 2 is a graph illustrating dose response curves of the tested, the clinical benchmark and IgG isotype control antibodies using the PathHunter PRLR functional assay tested for their activities against PRLR activation in the assay cells overexpressing a PRLR-enzyme fragment fusion.

To measure the engagement of PRLR upon treatment with the exemplary anti-PRLR antibodies, freshly-thawed assay cells were plated on a 96-well plate overnight and treated with an IgG isotype control antibody, the test candidates, and a clinical benchmark under 10-point serial dilutions for 1 hour. The cells were then exposed to PRL at a predefined concentration for 3 hours before measuring the chemiluminescence signal using a plate reader. Curve fitting was performed using the four-parameter non-linear regression model. The in vitro potency of the tested antibodies was reported as the half-maximal inhibitory concentration ($IC_{50}$) values. Results indicate a decrease in luminescence when treated with the exemplary anti-PRLR antibodies compared with the IgG isotype control (FIG. 2). Corresponding $IC_{50}$ values are noted in Table 15.

TABLE 15

$IC_{50}$, 95% CI and R-squared (R2) Values Determined in the PathHunter Assay

| | AB001 | AB012 | AB007 | AB005 | AB009 | AB013 | AB000 |
|---|---|---|---|---|---|---|---|
| IC50 | 0.79 | 0.64 | 0.86 | 0.63 | 2.22 | 0.94 | 0.44 |
| 95% CI | 0.69-0.97 | 0.53-0.75 | 0.76-1.12 | 0.55-0.73 | 1.36-3.21 | N.D.-1.70 | 0.38-0.51 |
| $R^2$ | 0.97 | 0.97 | 0.97 | 0.97 | 0.94 | 0.97 | 0.97 |

B. Engagement with Human and Mouse PRLRs Measured by Meso Scale Discovery Assay

The engagement of the exemplary anti-PRLR antibodies with human and mouse prolactin receptors was determined by measuring downstream activity of the receptor upon treatment with the antibody using a Meso Scale Discovery assay.

Engagement of prolactin (PRL) with the prolactin receptor (PRLR) on the surface of mammalian cells triggers the recruitment of JAK2 tyrosine kinase and STAT5 to the cytoplasmic region of PRLR, culminating in the phosphorylation and activation of STAT5. Meso Scale Discovery (MSD) assay is a widely used immunoassay that uses electrochemiluminescence (ECL) and multiarray technology to detect multiple proteins from a single sample. Specifically, an MSD phospho-Y694 (p-Y694)/total STAT5A/B assay, a multiplex assay that is compatible with human and mouse PRLR (hPRLR and mPRLR respectively) was utilized to assess the efficacy of the test candidates to engage the prolactin receptor compared to the clinical benchmark antibody.

To measure the engagement of Anti-PRLR antibodies with the PRLR receptor, PRLR-expressing and -responsive human mammary carcinoma T47D cell line or immortalized mouse mammary epithelial cell line HC11 were plated in a 96-well plate and incubated overnight. Both these cell lines exhibit activation of the PRLR/JAK2/STAT5 signaling pathway upon PRL binding. The cells were subsequently treated with a control antibody, the test candidates, and a clinical benchmark antibody under 10-point serial dilutions for 1 hour. The cells were exposed to species-matching PRL at a predefined concentration for 15 minutes before lysis. The resulting cell lysates were transferred to the MSD MULTI-SPOT 96-well 4-spot plate that was pre-coated with capture antibodies specific for p-Y694 and total STAT5A/B, strategically placed on distinct spots within each well. The immobilized p-STAT5A/B and total STAT5A/B in T47D cell lysates are detected using an anti-total STAT5A/B antibody conjugated with the electrochemiluminescence compound MSD SULFO-TAG™. The signals emitted from each spot are then quantified and analyzed using the MSD plate reader and corresponding MSD software. The efficacy of the test candidates was evaluated by measuring the ratio of pY694 STAT5 to total STAT5 in T47D or HC11 cells subjected to various treatments in triplicates. The in vitro potency of the test candidates was reported as the half-maximal inhibitory concentration ($IC_{50}$) values calculated using the four-parameter non-linear regression model for each treatment variable.

Figure 3:
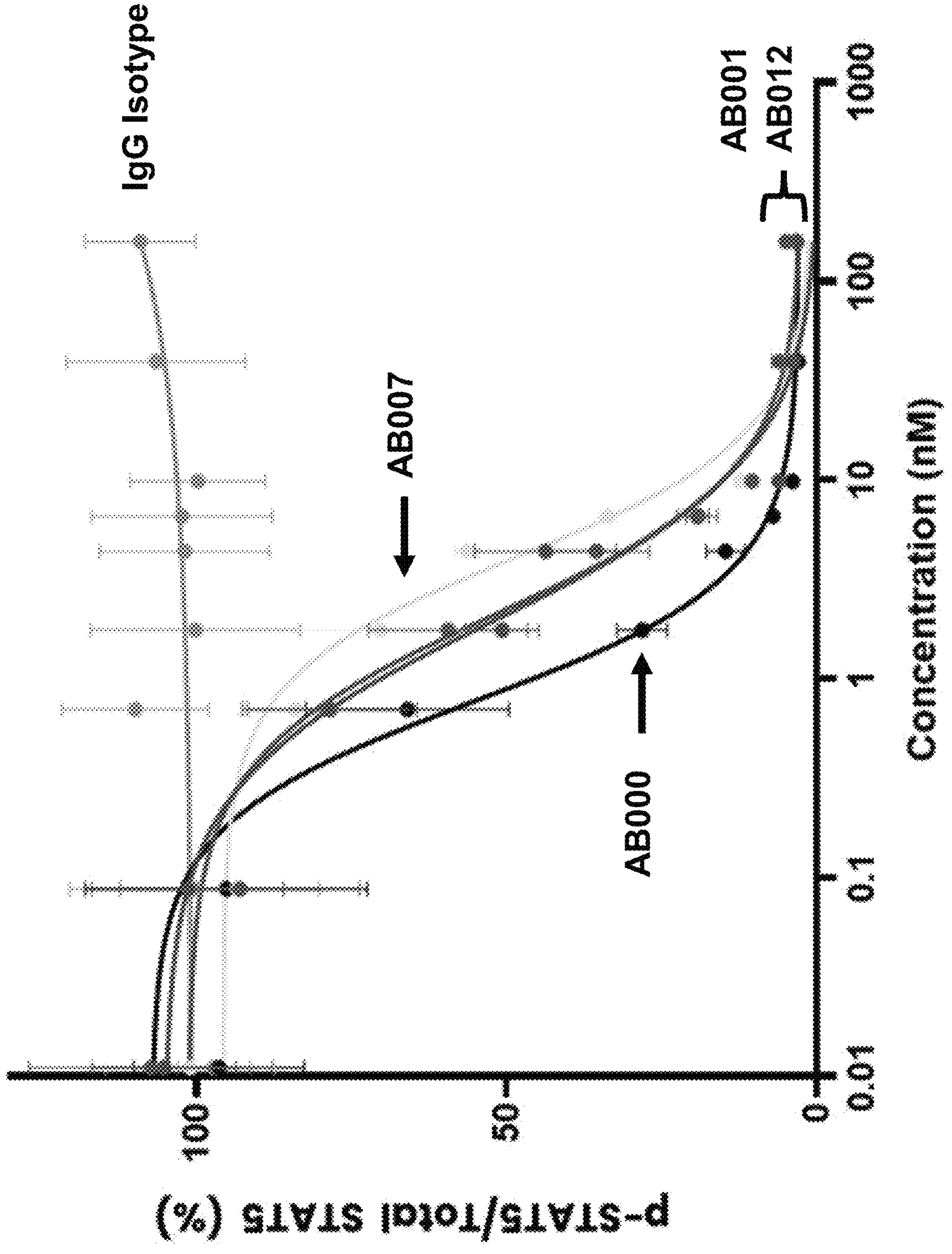
FIG. 3 is a graph illustrating dose response curves of the tested, the clinical benchmark and IgG isotype control antibodies against PRLR activation in T47D cells using the MSD p-STAT5/total STAT5 assay.

While the in vitro efficacy of the test candidates was lower in the mouse HC11 cells compared to the human T47D cells, both T47D (FIG. 3) and HC11 (FIG. 4) cells, the test candidates and the clinical benchmark antibody showed a reduction in the percentage of p-STAT5/Total STAT5 compared to the isotype control. This was also reflected in the corresponding differences in the IC50 values for the test candidates between the two model systems (Tables 16 and 17).

TABLE 16

$IC_{50}$, 95% CI and R-squared (R2) Values for MSD Assay from T47D Cells

| | AB001 | AB012 | AB007 | AB000 |
|---|---|---|---|---|
| IC50 | 2.10 | 1.93 | 4.092 | 0.77 |
| 95% CI | 1.27 to 3.00 | 1.32 to 2.75 | 3.06 to 5.19 | 0.63 to 0.99 |
| $R^2$ | 0.93 | 0.95 | 0.96 | 0.98 |

TABLE 17

$IC_{50}$, 95% CI and R-squared (R2) values for MSD Assay from HC11 Cells

| | AB001 | AB012 | AB007 | AB000 |
|---|---|---|---|---|
| IC50 | 4.28 | 5.71 | 7.67 | 1.76 |
| 95% CI | 2.43 to 7.74 | 2.96 to 16.6 | 3.98 to 30.8 | 1.34 to 2.42 |
| $R^2$ | 0.82 | 0.91 | 0.9 | 0.97 |

Example 7. Ex Vivo Immunogenicity of Exemplary Anti-PRLR Antibodies

This example summarizes an assay performed to assess ex vivo immunogenicity of the test candidates. Assessment of ex vivo immunogenicity is critical for ensuring safety and efficacy of biotherapeutics. Biotherapeutics can be screened for eliciting CD4+ T cell expansion and/or cytokine secretion in PBMCs (human peripheral blood mononuclear cells) to de-risk immunogenicity. Specifically, measuring CD4+ T cell activation markers, CD134 and CD137 has been found to correlate well with clinical ADA levels.

The following is an exemplary protocol to measure immunogenicity. PBMCs for seven HLA supertypes (two from each supertype) were incubated with test candidates, a program reference molecule, media only, the positive control protein KLH (keyhole limpet hemocyanin), or benchmark clinical mAbs (bevacizumab, bococizumab, or huA33) with low, middle, and high ADA rates, respectively. After stimulation for 72-80 hrs, cells were stained with anti-CD4, CD137, and CD134 antibodies. The SI for each condition was calculated as the fraction of CD4 positive cells positive for either CD137, or CD134, or both in mAb stimulated cells divided by the fraction of cells positive in media only, thus the media only SI was normalized to 1. Each condition was analyzed in triplicate and averaged.

Figure 5A:
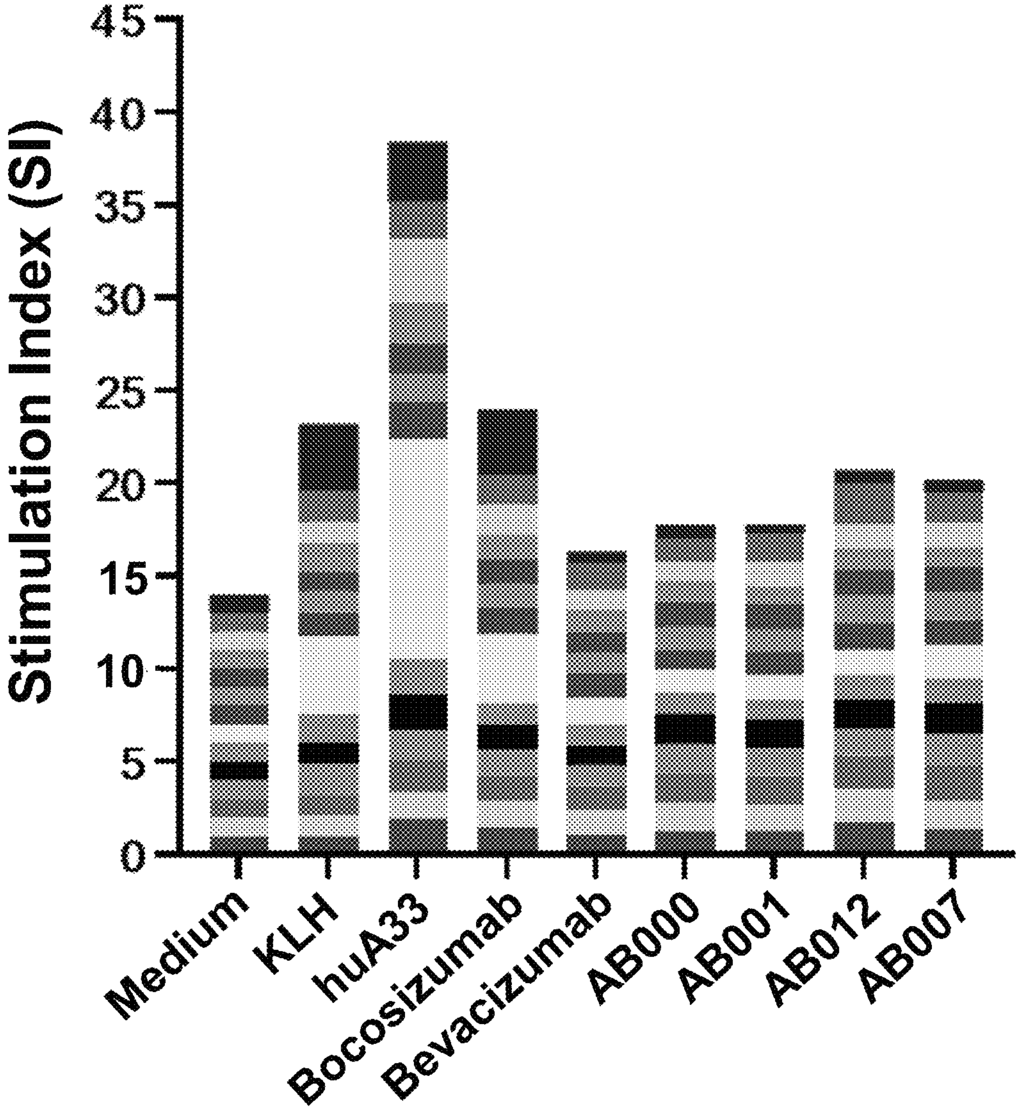
FIGS. 5A-5B include graphs showing ex vivo immunogenicity measurements of exemplary anti-PRLR antibodies as indicated.
Figure 5B:
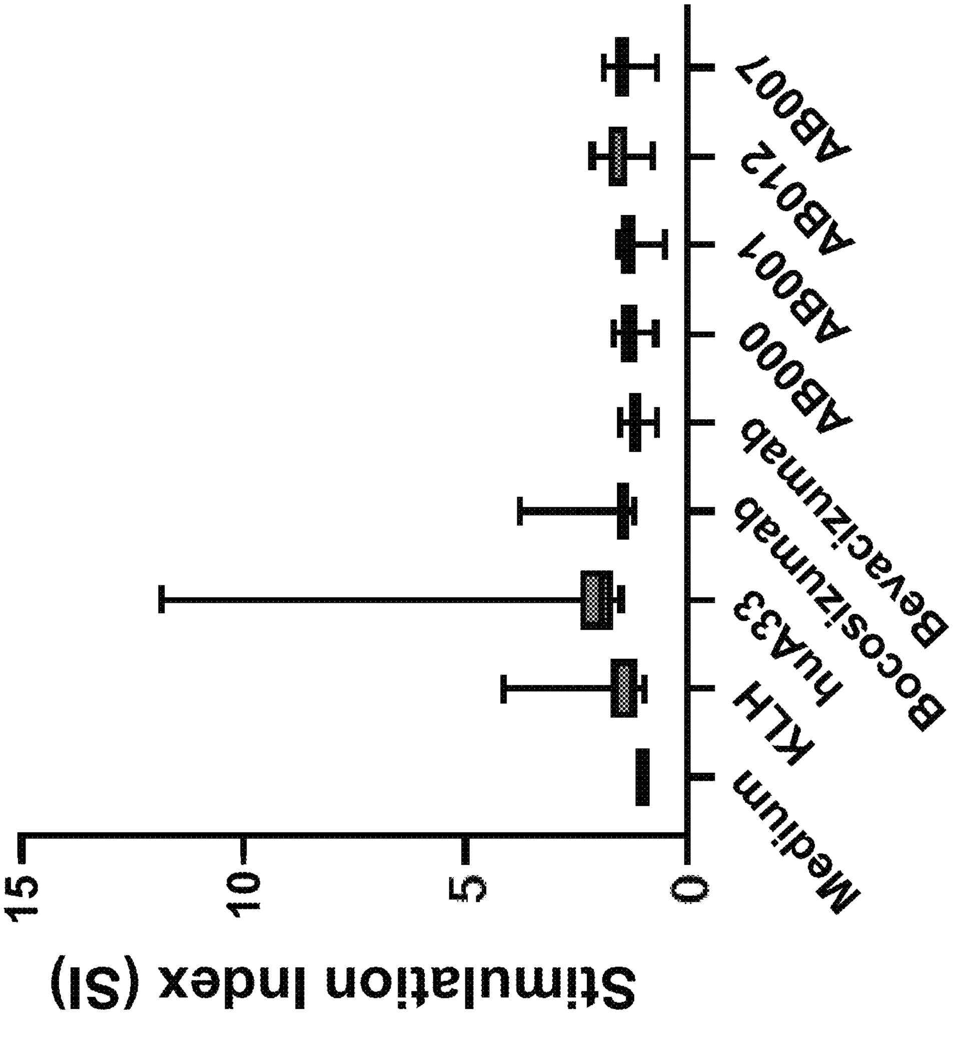

Assay technical controls met performed as expected. The cumulative stain index values (shown in Table 18 below) for assay positive control, KLH, along with benchmark mAbs represent T cell activation over the medium only condition by paired t-test (p-value range 0.006, 0.030). Low SI was observed for the media control, and a high SI was observed for the positive control and the benchmark antibody with expected SI values as predicted by their known ADA rates FIGS. 5A and 5B). The exemplary anti-PRLR antibody AB001 exhibited cumulative stimulation index values that align closely with the low Immunogenic benchmark Bevacizumab. Similarly, exemplary anti-PRLR antibodies AB012 and AB007 showed cumulative Stimulation Index values that were low within the low-to-medium benchmark range (FIGS. 5A and 5B). The summation of SI across 14 donors has been shown to correlate closely to clinical ADA rate. Combined, these results shows that test candidates do not demonstrate substantial risk in this ex vivo immunogenicity assay.

TABLE 18

Cumulative Drug Stimulation Index (SI) Values Across Fourteen HLA-Typed Donors

| | | Donors | | | | | | |
|---|---|---|---|---|---|---|---|---|
| | SI SUM | A | B | C | D | E | F | G |
| Medium | 14.00 | 1 | 1 | 1 | 1 | 1 | 1 | 1 |
| KLH | 23.18 | 3.57 | 1.7 | 1.22 | 1.51 | 1.01 | 1.13 | 1.29 |
| huA33 | 38.39 | 3.24 | 2.02 | 3.4 | 2.15 | 1.71 | 1.52 | 2.01 |
| Bococizumab | 23.99 | 3.56 | 1.54 | 1.7 | 1.29 | 1.34 | 1.28 | 1.38 |
| Bevacizumab | 16.33 | 0.69 | 1.38 | 1.08 | 1.24 | 1.1 | 1.1 | 1.28 |
| AB000 | 17.76 | 0.72 | 1.25 | 1.1 | 1.1 | 1.31 | 1.27 | 1.04 |
| AB001 | 17.79 | 0.49 | 1.57 | 1.26 | 0.97 | 1.33 | 1.31 | 1.19 |
| AB012 | 20.71 | 0.77 | 2.14 | 1.33 | 1.15 | 1.34 | 1.55 | 1.38 |
| AB007 | 20.19 | 0.7 | 1.64 | 1.31 | 1.07 | 1.33 | 1.5 | 1.34 |

| | Donors | | | | | | |
|---|---|---|---|---|---|---|---|
| | H | I | J | K | L | M | N |
| Medium | 1 | 1 | 1 | 1 | 1 | 1 | 1 |
| KLH | 4.15 | 1.55 | 1.16 | 1.71 | 1.07 | 1.14 | 0.97 |
| huA33 | 11.85 | 1.91 | 1.93 | 1.58 | 1.7 | 1.49 | 1.88 |
| Bococizumab | 3.77 | 1.19 | 1.27 | 1.45 | 1.37 | 1.38 | 1.47 |
| Bevacizumab | 1.5 | 1.11 | 1.04 | 1.13 | 1.27 | 1.32 | 1.09 |
| AB000 | 1.29 | 1.11 | 1.59 | 1.66 | 1.58 | 1.45 | 1.29 |
| AB001 | 1.33 | 1.07 | 1.52 | 1.5 | 1.58 | 1.4 | 1.27 |
| AB012 | 1.35 | 1.35 | 1.55 | 1.49 | 1.77 | 1.78 | 1.76 |
| AB007 | 1.81 | 1.35 | 1.64 | 1.72 | 1.89 | 1.52 | 1.37 |

Example 8. ADCC Activity of Exemplary Anti-PRLR Antibodies

This example describes experiments conducted to quantitate presence or absence of Antibody-dependent cell toxicity (ADCC) in target cells treated with the test candidates.

Antibody-dependent cell cytotoxicity (ADCC) is an important mechanism by which the immune system recognizes and destroys virus-infected or other diseased cells (e.g., tumor/cancer cells) through immune cells activated by antibodies bound to the target cells. Some population of immune cells, such as natural killer (NK) cells recognize antibody bound to a target cell through interaction with CD16A receptor that interacts with Fc region of the antibody. CD16A activates upon tight binding to the Fc part of IgG on the surface of a target cell and triggers a chain of signal transduction events culminating in the activation of the transcription factor NFAT. Although ADCC is desirable for some therapeutic applications, for example, to mediate anti-tumor activity, in the context of a proposed application, ADCC will be deleterious and thus undesirable.

Figure 6:
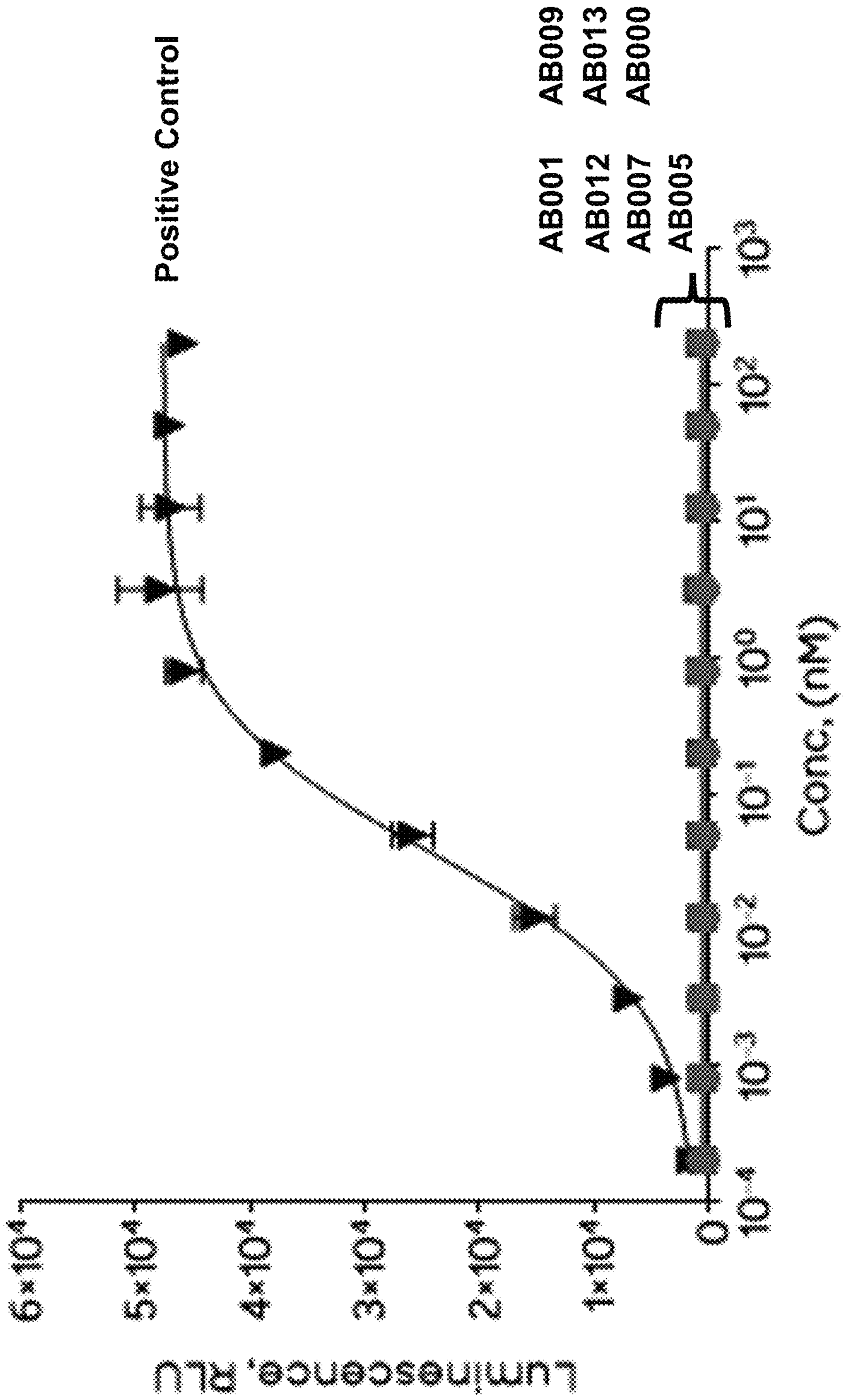
FIG. 6 is a graph illustrating Antibody-dependent cellular cytotoxicity (ADCC) activity of test candidates.

To test for ADCC activity of the test candidates, an in vitro ADCC reporter cell line assay with PRLR-positive cells (T47D) as target cells and Jurkat-Lucia-CD16a-NFAT-Luc ADCC reporter cells (InvivoGen) as effector cells was performed. The expression level of luciferase can be precisely measured and represents the degree of NK cell activation by a given antibody with given target cells. For this assay, target T47D were plated in a standard tissue culture-treated 96-well plate at a density of 80,000 cells per well in 100 μL of growth medium and incubated overnight at 37 °C with 5% $CO_2$. The following morning, the growth medium was aspirated from the 96-well plate containing the T47D cells, and serially diluted antibodies were added in a volume of 50 μL per well. The target cells were then incubated with the diluted antibodies for two hours under the same conditions. Effector cells were thawed from cryostorage, added to achieve a final plating density of 80,000 cells per well in 50 μL of growth medium, and incubated for 18 hours at 37 °C with 5% $CO_2$. After overnight incubation, 20 μL of supernatant from the co-culture of T47D and ADCC reporter cells was transferred to a fresh white opaque 96-well plate and mixed with 50 μL of luciferase substrate. The luminescent signal intensity was measured using a multimode microplate reader (Spectra Max i3x, Molecular Devices). The raw data were fitted to four-parameter logistic curves. The results from this assay show absence of ADCC activity in the test exemplary anti-PRLR antibodies (FIG. 6).

Example 9: Improvement of Hair Growth by Exemplary Anti-PRLR Antibodies

This example explores preclinical efficacy of exemplary anti-PRLR antibodies provided herein for enhancing hair growth using a mouse hair growth/alopecia model in ~6-7 week old C57BL/6 female mice.

Methods: Efficacy of test articles (including AB000 as a control and AB001) were evaluated in a randomized, controlled preclinical study. Animals were shaved until the skin was visible, then randomized into treatment groups based on skin color and initial body weight. Hair growth scores were recorded twice weekly using a predefined scale (see Table 19). Key endpoint included time to dense, normal coat hair regrow. Antibodies were administered twice weekly i.p. at 30 or 60 mg/kg, minoxidil 5% topical was applied once daily.

Figure 7:
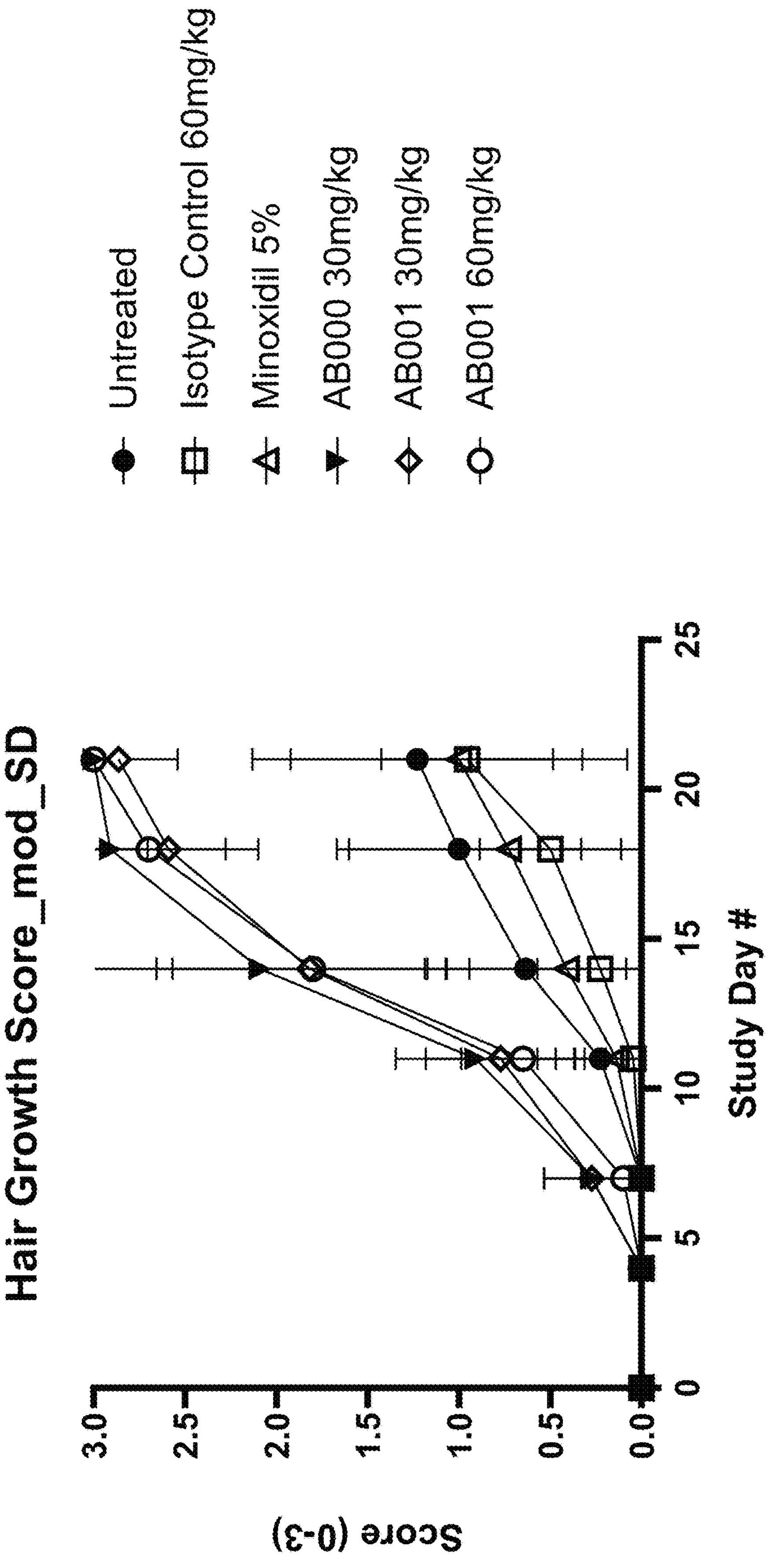
FIG. 7 is a graph illustrating the hair growth improvement effect of exemplary anti-PRLR antibody AB001 provided herein.

Results: Table 19 below summarizes the hair growth scoring criteria. As shown in FIG. 7, AB001 significantly increased hair regrowth compared to 5% topical minoxidil ($p<0.0001$—2way ANOVA).

TABLE 19

Hair Growth Scoring Criteria

| SCORE | SCALE |
|---|---|
| 0 | Initial state-pink/grey skin with no hair growth. |
| 0.5 | Skin color changes from pink/grey to bluish or contains dark pigment spots without visible hair growth |
| 1 | Skin color changes from pink/grey to bluish or contains dark pigment spots with visible hair growth (<20% coverage) |
| 1.5 | Grey/blue pigmentation with sparse hair growth (20-40% coverage) |
| 2 | Grey/blue pigmentation with Sparse or diffuse short hair growth (40-60% coverage) |
| 2.5 | Grey/blue pigmentation with moderate hair growth (60-80% coverage) |
| 3 | Dense, normal coat hair (80-100% coverage) |

Example 10: Mutagenesis Studies on AB001 Yeast Surface Display High-Throughput Screening Yeast surface display (YSD) paired with flow cytometry and deep gene sequencing ("Sort-Seq") allows for the construction of antigen binding curves of all observed members of a genetic library in parallel. This example describes a deep mutational scan of AB001 to determine binding affinity, or lack thereof, of each possible single mutant in a CDR region with YSD high-throughput screening. The CDR definition used here is Kabat. See Tables 1 and 2 above.

HC and LC Library Construction

For each residue in the CDRs (Kabat definition), YSD scFv variants were produced with all possible single mutants excluding the amino acid cysteine. A heavy chain library (HC or HCDR library) and a light chain library (LC or LCDR library) were generated and screened independently due to sequencing method limitations. These libraries were generated, cloned, cultivated, and screened in parallel to generate KD estimates for each variant in the libraries.

All possible single mutants for each HCDR position were generated in duplicate as well as 5 copies of the AB001 sequence. Any mutation that introduces an N-linked glycosylation motif is automatically removed from the library. This process results in 1,077 DNA sequences that encode 537 unique antibodies. To get under the 1,000 oligo tier, duplicates were removed for any mutant that changes the parental residue to either "M", "P", or "W". This ensures that all possible mutants are present and allows for duplicate measurements of most variants. The final HC library has 991 unique DNA sequences encoding 537 unique antibodies.

The same process is used to create the LC library. The LC library produced 1,107 DNA sequences that encode 552 unique antibodies. The same sampling was done with the additional deduplication of mutations to "Q". The final LC library has 987 DNA sequences encoding 552 unique antibodies, including 5 copies of the AB001 LC sequence.

The libraries were cloned and cultivated using standard methods. In brief, the oligos were amplified before ligating it to an intermediate vector generating an intermediate library. The QC of these libraries suggests 100% representation of the variants designed. Post sequencing QC, the desired region of interest containing the scFv component was digested out of the intermediate library and transformed using electroporation in yeast host EB622 with a static fragment in equimolar conc. which contains elements required for selection and propagation of vectors in yeast host. Post transformation, the libraries went through seed culture in CM-CAA (chemically defined media with casamino acid and 2% glucose) media followed by induction in SG-CAA media (Synthetic media containing 2% galactose as an inducer and 0.2% glucose). Post transformation and at the start of cultivation, another round of QC is performed to analyze representation of designed sequences in the library to be screened. Based on the information, there was 100% representation of sequences designed in the library Screening.

Before screening, an analytical flow cytometry run with control strains and the two libraries were performed to assess expression and binding of the libraries to PRLR.

The libraries were subjected to one titration sort without prior enrichments. Standard overnight staining and sorting was implemented. Gating for all samples labeled with PRLR is standard and as follows. Gating is performed on a histogram of PRLR binding (AF647). The positive binding distribution is divided into 3 equivalent gates (P1-3) on a biexponential axis, with one additional gate to cover the binding negative population (P4).

During our pre-sort analytical flow cytometry run, expression of the AB001 scFv and its binding to PRLR were observed. scFv expression, based on the presence of a cMyc tag, was 46% and 38% for the HC and LC libraries, respectively. Of the expressing cells in the HC and LC libraries, 91% and 97% exhibited binding to 500 nM PRLR, respectively. Based on these results, the HC and LC libraries were further investigated for binding to PRLR using the YSD AB001 scFv as a positive control.

HC and LC libraries were labeled with an anti-cMyc Alexa Fluor 488 antibody to confirm scFv expression and PRLR at the following concentrations: 500 nM, 200 nM, 80 nM, 32 nM, 12.8 nM, 5.12 nM, 2.05 nM, 0.819 nM, 0.328 nM, or 0 nM. Singlets and size gates were applied prior to sorting to exclude cell debris, aggregates, and outliers based on size. An expression gate based on the presence of a cMyc tag was applied to exclude non-expressing yeast from titration sorts.

Figure 4:
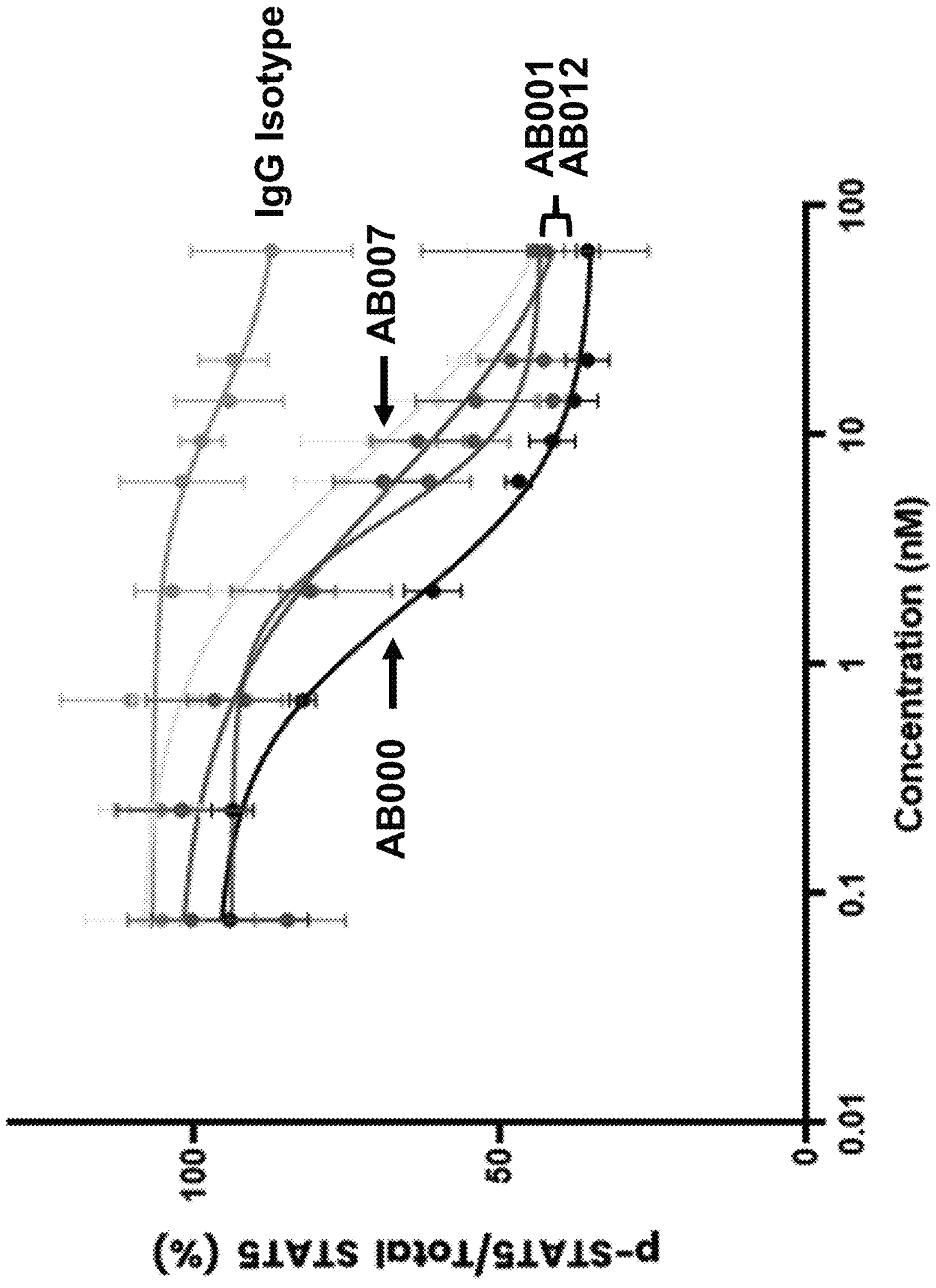
FIG. 4 is a graph illustrating dose response curves of the tested, the clinical benchmark and IgG isotype control antibodies against PRLR activation in HC11 cells using the MSD p-STAT5/total STAT5 assay.

At all concentrations of PRLR except 0 nM, expression+/binding+ cells were sorted into three gates of equal size based on antigen binding on a biexponential distribution (P1, P2, and P3). Expression+/binding− cells were sorted into an additional gate (P4). The gating scheme for these samples is shown in FIG. 4. At 0 nM PRLR, cells were sorted into three gates: expression+/binding+(P1+P2+P3), expression+/binding− (P4), and expression-/binding-. The expression−/binding− gate was drawn on a histogram showing cMyc expression and was the inverse of the expression gate drawn for backgating.

Figure 8A:
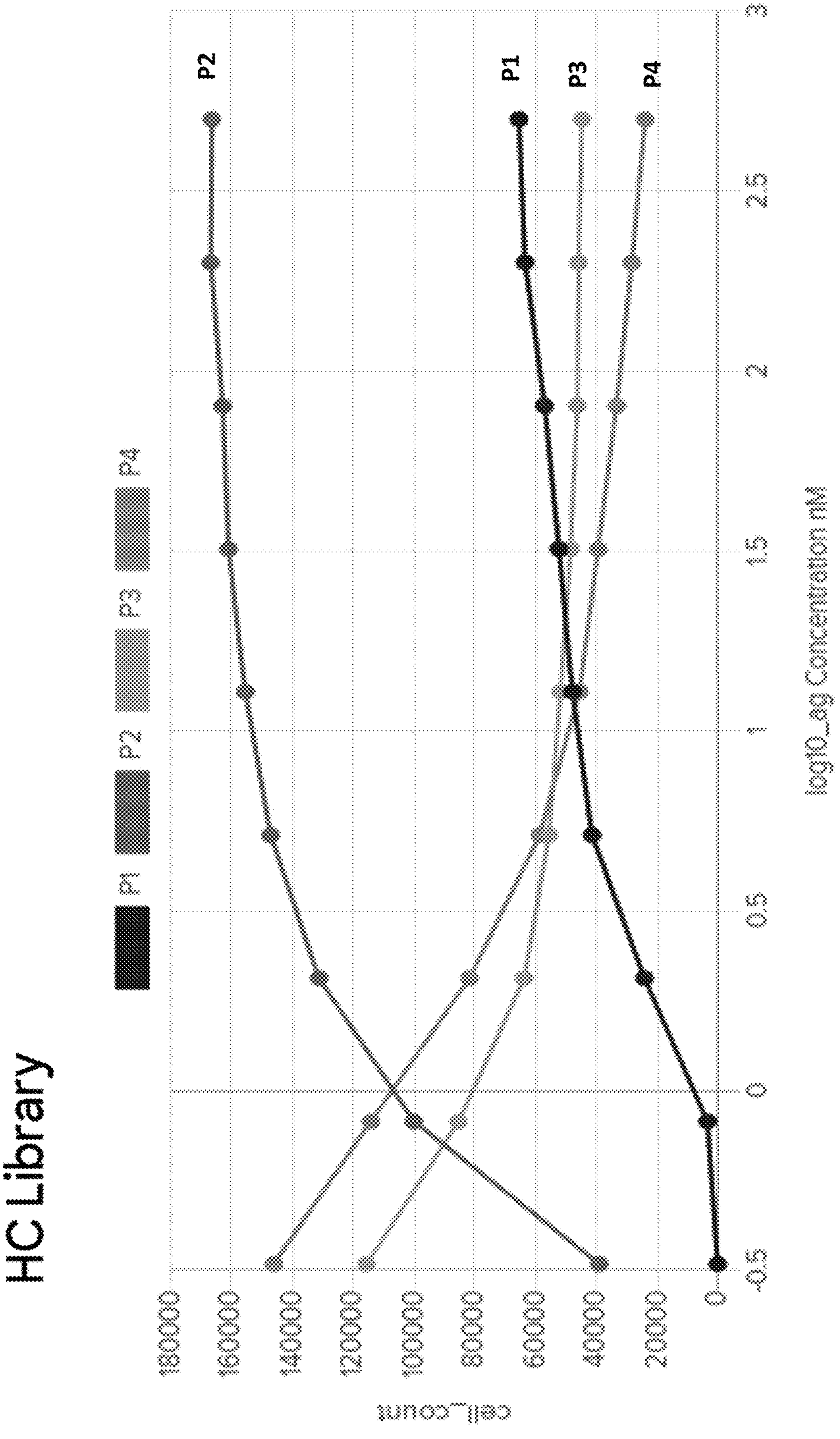
FIGS. 8A-8B include graphs showing cell counts in P1-P4 gates.
Figure 8B:
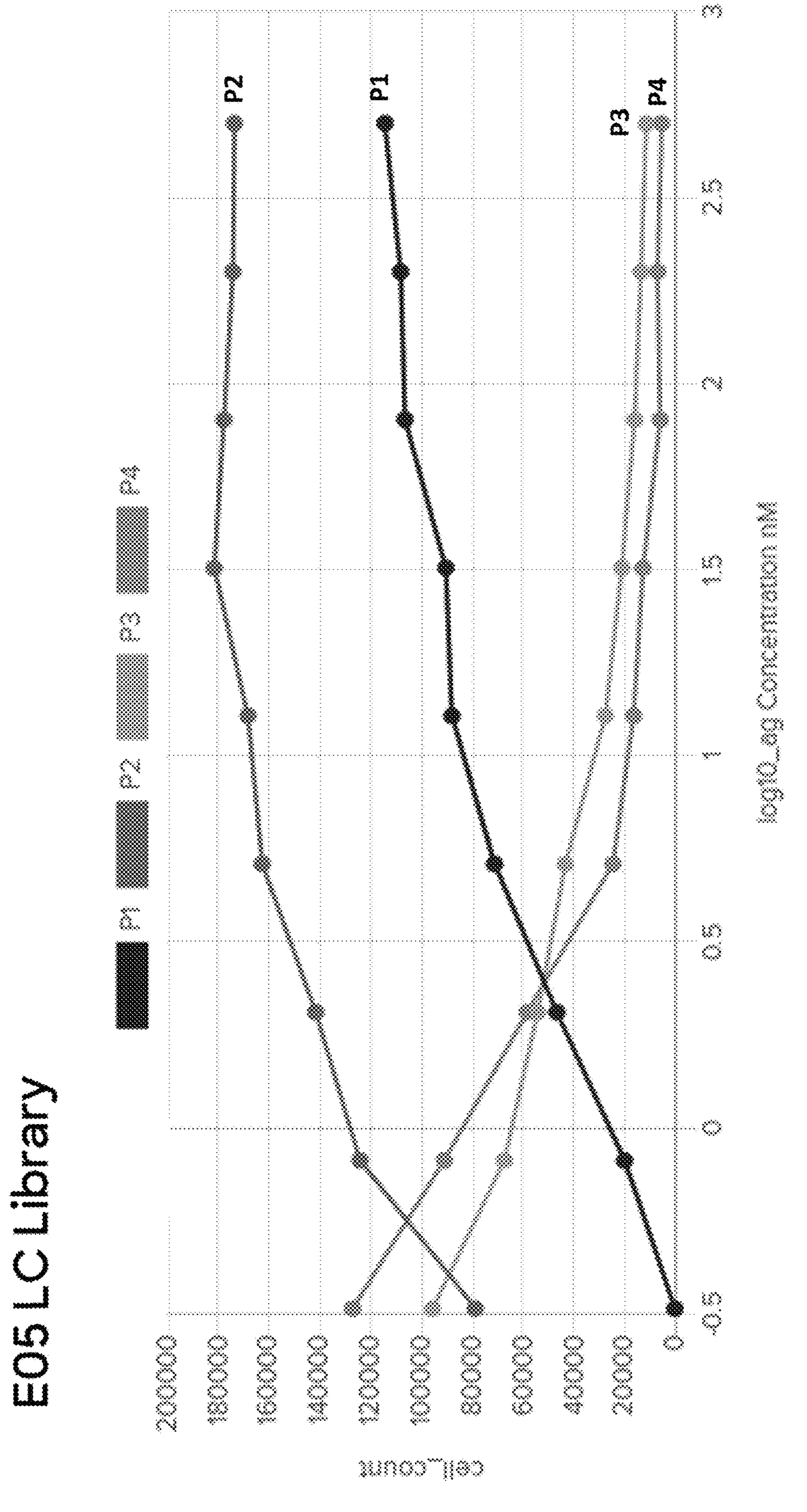

Across all gates at each concentration of PRLR, approximately 300× the library diversity, or 300,000 cells were collected. Cell counts in each gate P1, P2, P3, or P4 are shown for each concentration of PRLR in FIGS. 8A and 8B.

Results

Table 20A and Table 20B below lists impact of mutations at each heavy chain CDR position and each light chain CDR position on binding affinity to PRLR.

TABLE 20A

Mutagenesis Results of Heavy Chain CDR Positions

| | CDR Residues in AB001 | Binding not Detected | Similar Binding Activity to AB001 | Reduced Binding Activity |
|---|---|---|---|---|
| HCDR 1 | D ($X_1$) | | E | P, H, G, R, Y, T, V, L, W, Q, S, A |
| | Y ($X_2$) | | V, H, M, T, S, A, F | L, N, D, G, Q, E, R, P, I, W, K |
| | W | | | N, G, E, L, Q, H, M, I, V, D, F, T, S, A, K, P, Y, R |
| | M ($X_3$) | P, W | F, L | D, A, K, R, T, S, I, N, E, V, Y, G, Q, H |
| | H | P, K, W, R | | T, A, S, E, V, Q, M, N, D, G, Y, F, I, L |
| HCDR 2 | D | | | |
| | I ($Z_1$) | P | V | A, W, T, D, Y, N, L, R, H, S, K, E, G, Q, F, M |
| | S | | | T, P, E, D, Q, V, H, M, G, F, N, R, L, K, W, Y, A, I |
| | R | | | W, E, L, A, M, D, S, T, V, Y, K, N, F, G, H, I, P, Q |
| | L ($X_4$) | | I, F, V, M | E, S, N, R, G, H, A, T, W, Q, Y, D, K, P |
| | K ($X_5$) | | L, N, S, A, G, Q, P, Y, T, V, M, I, W, E, D, F, R, H | |
| | P ($Z_2$) | | G, D, S | I, F, L, K, R, A, V, M, H, Q, E, T, Y, W |
| | Y ($Z_3$) | | W, F | L, I, H, N, S, D, K, P, T, M, V, Q, R, E, G, A |
| | T ($X_6$) | | V, R, M, S | Q, I, E, A, F, W, Y, K, D, H, P, G, N, L |
| | N ($X_7$) | | A, G, S, Q | F, P, M, H, D, W, L, I, V, Y, K, E, R, T |
| | Y | | | T, Q, N, A, I, F, W, V, G, P, D, M, S, L, H, E, K, R |
| | A ($Z_4$) | | K, L, H, I, M, V, R | E, W, D, P, F, Q, G, Y |
| | D ($X_5$) | | S, W, G, K, Q, A, E, L, M, H, Y, T, F, I, N, R | P, V |
| | S ($Z_6$) | | D, A, R, T, K, N, M, P, H, W, Y, V, F, G, I, L, Q | E |
| | V ($Z_7$) | | M, A, L, T, F, I | Q, G, P, W, D, Y, E, N, H, S, R, K |
| | K ($Z_8$) | | N, Q, A, R, Y, T, W, I, F, V, G, H, S, L, E, D, M | P |
| | G ($Z_9$) | | H, N, T, F, R, K, Y, Q, S, D, P, A | L, E, W, V, I, M |
| HCDR 3 | G | W, V, T, R, Q, P, N, M, L, K, I, H, F, E, D, A, Y | | S |
| | L ($X_8$) | | T, E, A, M, R, Q | P, F, W, I, H, V, D, N, K, Y, S, G |
| | D | V, W, F, I, K, L, Y, T, Q, R, P, N | | G, E, M, H, S, A |
| | A ($Z_{10}$) | K | D, E, S | I, Y, W, G, R, F, Q, V, N, H, M, T, P, L |
| | R ($X_9$) | | A, M, I, K, V | W, G, Y, E, S, T, P, H, Q, D, N, L, F |
| | R | E, D | | F, P, L, T, G, I, N, Q, A, H, V, Y, S, W, K, M |
| | M | R, N, S, K, H, D, E, P | | I, V, A, Y, L, G, F, Q, T, W |
| | D ($X_{10}$) | P, R, K | E, S | Y, L, F, T, M, I, A, N, W, V, G, H, Q |
| | Y ($X_{11}$) | | F, N, R, K, W, E | I, L, Q, P, D, A, M, S, G, H, V, T |

TABLE 20B

Mutagenesis Results of Light Chain CDR Positions

| | CDR Residues in AB001 | Binding not Detected | Similar Binding Activity to AB001 | Reduced Binding Activity |
|---|---|---|---|---|
| LCDR1 | T ($Z_{11}$) | | I, R, G, F, S, K, D, A, L, W, H, M, V, Y, Q, E | P |
| | G | | | V, M, F, P, I, A, Y, H, E, K, W, S, N, L, R, Q, T, D |
| | S ($Z_{12}$) | | D, Q, Y, G, E, H, W, R, T, A | M, V, P, F, I, L, K |
| | G ($X_{12}$) | | F, S, P, R, M, E, D, A, H, I, Y, T, W, L, V, N, Q, K | |
| | T ($X_{13}$) | | Y, D, A, E, Q, S, N, H | M, G, V, L, K, P, R, W, F, I |
| | N | | | Y, S, L, K, H, F, I, Q, A, G, E, M, D, P, V, W, R, T |
| | I ($X_{14}$) | | L, M, V | A, R, N, D, E, K, F, Q, H, P, W, G, Y, S, T |
| | G ($X_{15}$) | | | M, D, A, H, I, R, K, F, Y, P, Q, E, W, N, V, L |
| | A ($X_{16}$) | | F, Y, Q, S, G, M | I, E, K, R, H, W, D, P, T, L, N, V |
| | G | | | R, Y, H, I, N, L, E, T, Q, M, K, S, P, D, A, V, F, W |
| | Y | D, P | | T, M, E, A, K, S, H, Q, G, V, I, W, L, N, F, R |
| | V | D, W, K, R | | N, Q, M, T, L, I, A, F, P, E, H, S, Y, G |
| | V ($X_{17}$) | | S, N, L, A, T | P, Y, M, D, G, F, E, H, I, Q, K, W, R |
| | H ($Z_{13}$) | | Q | P, D, A, L, M, V, T, N, S, G, Y, K, E, I, F, R, W |
| LCDR2 | R | | | |
| | N ($X_{18}$) | | | V, Q, S, E, K, W, Y, H, F, G, T, N, A, L, I, D, P, M |
| | N ($X_{19}$) | | S, H, T | V, Y, G, K, P, R, D, M, F, I, Q, A, E, L, W |
| | L ($X_{20}$) | | L, V, M, Q, E, K, I, W, A, Y, R, S, G, F, T, D, H | P |
| | R ($X_{21}$) | | V, H, F, I, Q, K, W, A, Y, R, M, E, N | D, P, G |
| | P ($Z_{14}$) | | I, L, P, W, Y, F, M, V, K, H, Q, N, A | E, G, D |
| | S ($Z_{15}$) | | I, F, M, K, T, G, D, R, L, Y, Q, N, A, E, S, V, H | W |
| LCDR3 | A ($Z_{16}$) | | T, S | Q, N, E, F, L, R, G, H, M, D, V, K, W, Y, P, I |
| | S ($X_{22}$) | | T, V, A | M, N, K, R, I, F, Y, D, G, W, E, Q, L, P, H |
| | W ($X_{23}$) | E | | M, I, S, V, A, F, R, Y, T, D, G, P, L, Q, H, N, K |
| | D | P, M | | H, I, Q, W, R, G, V, L, A, T, K, E, N, S, F, Y |
| | D ($Z_{17}$) | | N | R, E, H, F, P, S, K, A, Q, I, V, G, T, W, L, M, Y |
| | R ($X_{24}$) | | M, E, F, W, L, A, Y, S, T, P, K, H, I, G, D, Q, V, N | |
| | H ($X_{25}$) | | I, D, L, Y, F, V, M, E, K, A, S, N, R, W, T, Q | G, P |
| | Q ($X_{26}$) | | G, T, A, M, F, E, S, N | H, L, Y, K, D, I, W, P, V, R |
| | A ($X_{27}$) | P | K, S, G | Q, E, F, H, D, W, Y, R, L, N, T, V, I, M |
| | W | | | V, A, T, P, Y, Q, N, G, R, S, H, I, F, E, D, L, K, M |
| | L ($Z_{18}$) | | M, I, F, G, A, V | T, Y, K, S, H, P, W, E, Q, R, D, N |

Example 11: Assessing the Efficacy of an Exemplary Anti-PRLR Antibody in Modulating PRL-Induced Anagen-to-Catagen Transition in Human Hair Follicles Using an Ex Vivo Model This example investigates the efficacy of an exemplary anti-PRLR antibody AB001 in modulating prolactin (PRL)-induced transition of human scalp hair follicles from the anagen (growth) phase to the catagen (regression) phase using an ex vivo organ culture model. Functional outcomes were assessed across three key categories: macroscopic and microscopic evaluation of hair cycle progression, analysis of follicular pigmentation and morphology, and characterization of cellular proliferation and apoptosis of follicular keratinocytes.

Briefly, four hairy skin punch biopsies about 4 mm in size were obtained from three male human donors on Day 0. To evaluate the ability of AB001 to modulate PRL-induced alterations in hair follicle biology, human scalp skin punches were treated with the following conditions on Day 0: control IgG1 (1 μM), AB001 (1 μM), control IgG1 (1 μM) plus PRL (400 ng/mL), and AB001 (1 μM) plus PRL (400 ng/mL). The ex vivo cultures of were treated again on Day 3 and Day 5. On Day 6, the control or treated culture supernatants were collected, and the skin cultures were embedded in OCT compound for subsequent analysis.

Figure 9A:
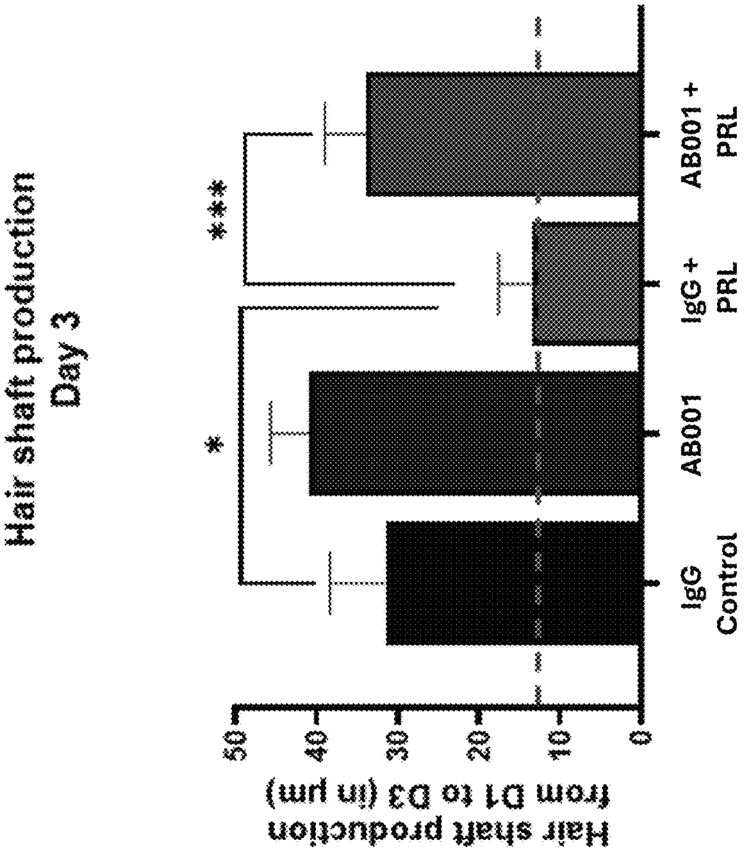
FIGS. 9A-9B are graphs showing phototrichogram analyses of ex vivo cultured human male scalp skin treated as indicated and assessed three days post-treatment.
Figure 9B:
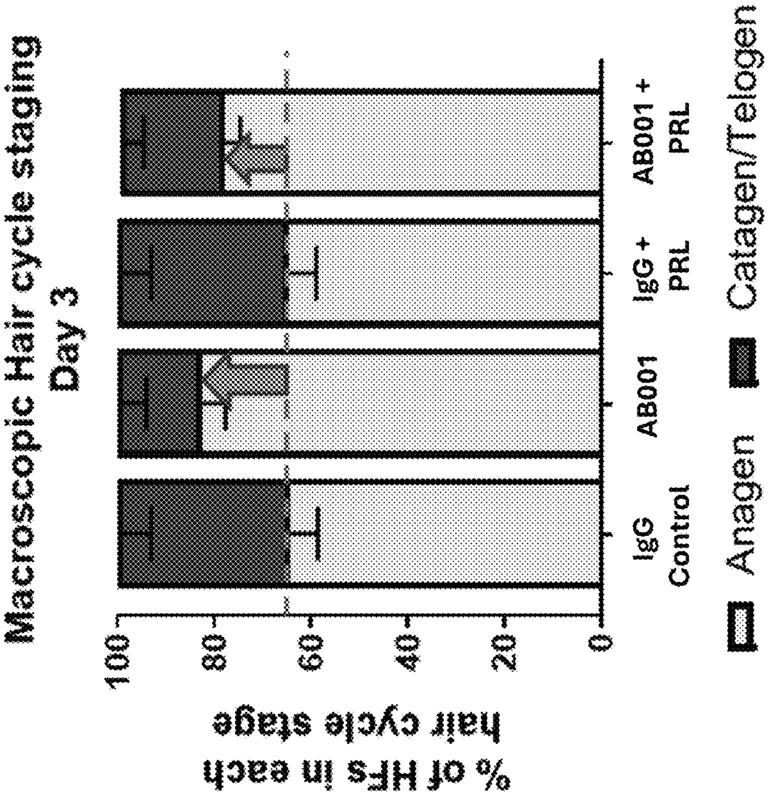
Figure 10A:
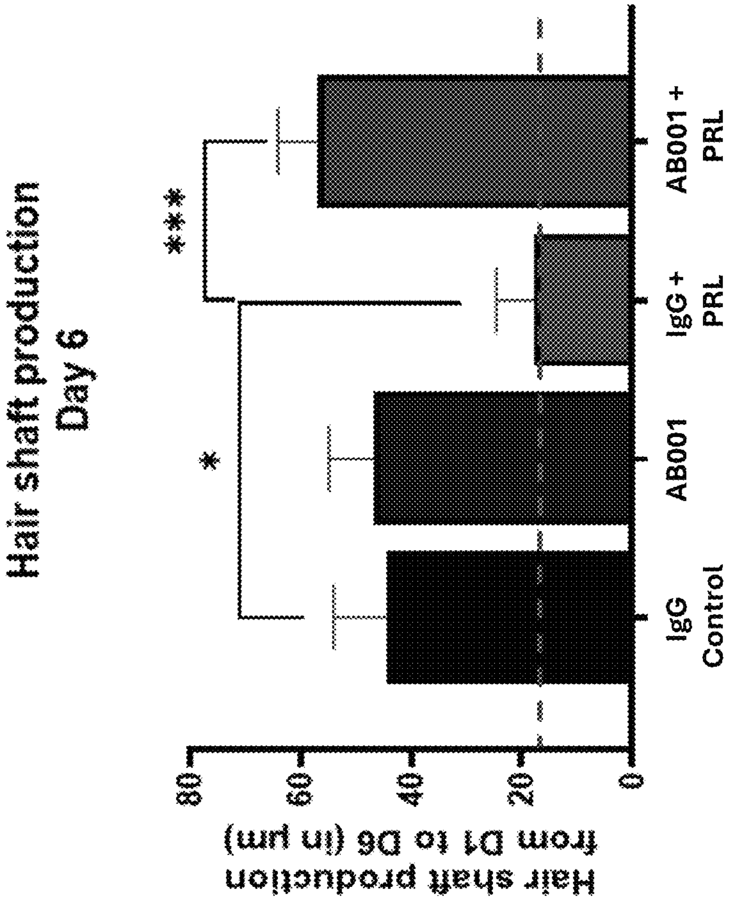
FIGS. 10A-10B are graphs showing phototrichogram analyses of ex vivo cultured human male scalp skin treated as indicated and assessed six days post-treatment.
Figure 10B:
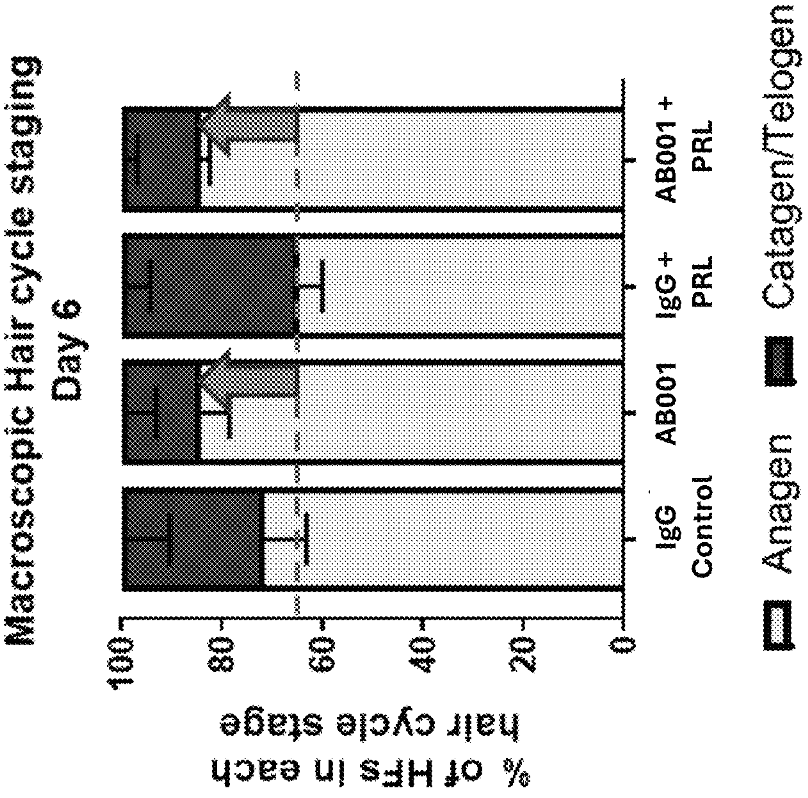
Figure 11:
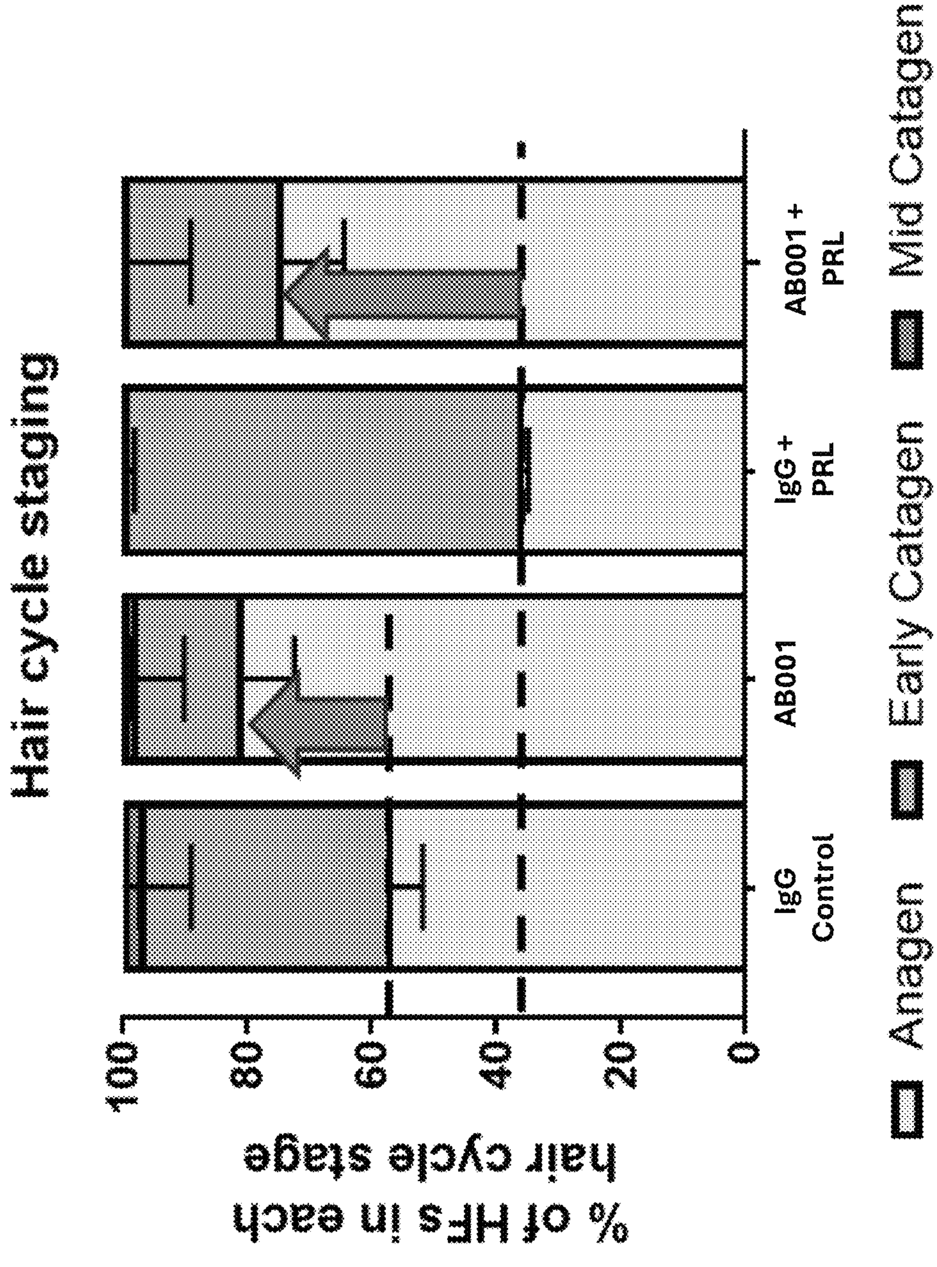
FIG. 11 is a graph showing microscopic hair cycle staging of ex vivo cultured human male scalp skin treated as indicated and assessed six days post-treatment. Data represents mean±SEM; n=35-43 hair follicles from 3 male donors.

As evaluated by phototrichogram analysis, PRL treatment significantly reduced hair shaft production at both short-term (Day 3 post-treatment; FIG. 9A) and long-term (Day 6 post-treatment; FIG. 10A) time points compared to the control. At both these time points, AB001 significantly rescued PRL-induced reduction in hair shaft production (FIGS. 9A and 10A). Further, macroscopic hair staging analysis showed that PRL treatment lowered the percentage of hair follicles in the anagen phase and increased the percentage of hair follicles in catagen/telogen phase as compared to the control. (FIGS. 9B and 10B). Consistent with the observed increase in hair shaft production as described above, AB001 effectively rescued PRL-induced decrease in the percentages of hair follicles in the anagen phase on Days 3 and 6 post-treatment (FIGS. 9B and 10B). AB001 treatment alone also increased anagen as compared to the IgG control (FIGS. 9B and 10B) at both time points tested, demonstrating a role of AB001 in facilitating hair growth. On Day 6 post-treatment, Warthin-Starry histochemistry and Ki-67/TUNEL immunostaining were performed for accurate determination of hair cycle staging of the ex vivo human scalp cultures. This microscopic hair cycle staging demonstrated that AB001 treatment alone increased the percentage of hair follicles in anagen (FIG. 11). As also noted above, while PRL alone reduced the percentage of hair follicles in anagen compared to the control, which is indicative of premature catagen induced by hair follicle PRL, AB001 treatment prevented the premature catagen transition (FIG. 11).

Figure 12:
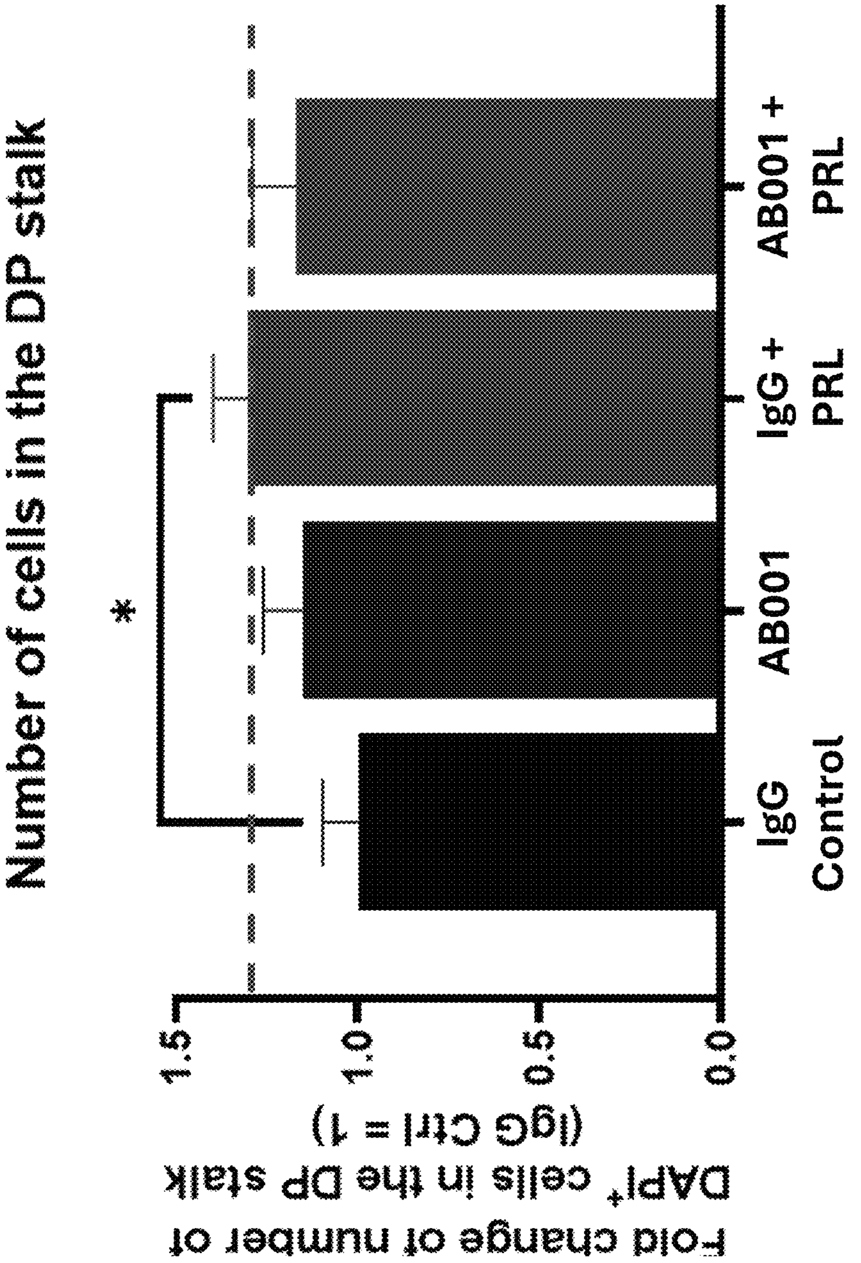
FIG. 12 is a graph showing fold change in the number of cells in the dermal papilla stalk of ex vivo cultured human male scalp skin treated as indicated and assessed six days post-treatment. Data represents mean±SEM; n=29-33 hair follicles from 3 male donors.
Figure 13A:
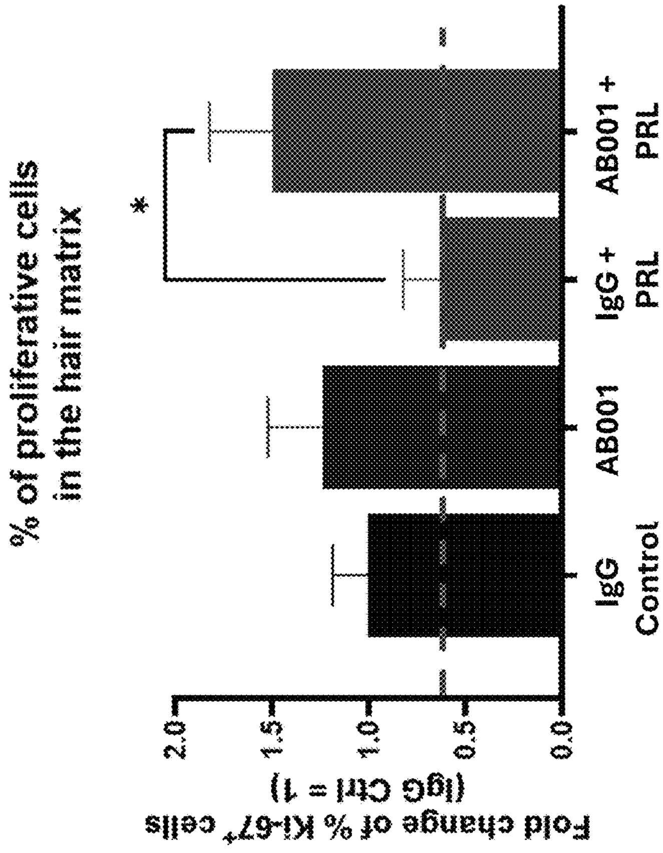
FIGS. 13A-13B are graphs showing fold changes in the number of proliferative and apoptotic cells in the hair matrix of ex vivo cultured human male scalp skin treated as indicated and assessed six days post-treatment.
Figure 13B:
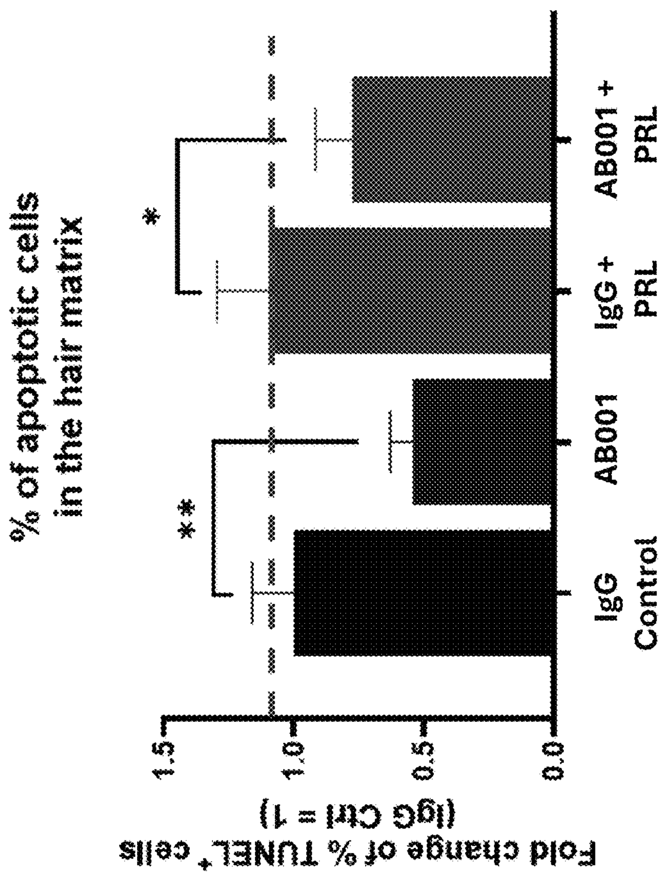

Next, emigration of dermal papilla (DP) fibroblasts, which are located at the base of hair follicles within the dermal papilla (DP) was analyzed as a surrogate for hair follicle miniaturization, a marker for androgenic alopecia. An increase in DP emigration reflects a reduction in the number of DP fibroblasts, which may result in a smaller DP and contribute to hair follicle miniaturization. As shown in FIG. 12, although PRL-treatment significantly increased the number of cells in the DP stalk, AB001 did not alter the number of emigrating DP fibroblasts in the DP stalk in the presence or absence of PRL as compared to the control. Further, AB001 significantly reversed the PRL-induced decrease in proliferation and PRL-induced increase in apoptosis of hair matrix (HM) keratinocytes (FIGS. 13A and 13B). Further, AB001 alone reduced the percentage of apoptotic HM keratinocytes compared to the IgG control (FIG. 13B). These findings support a role of AB001 in counteracting PRL-induced inhibition of hair growth.

Figure 14B:
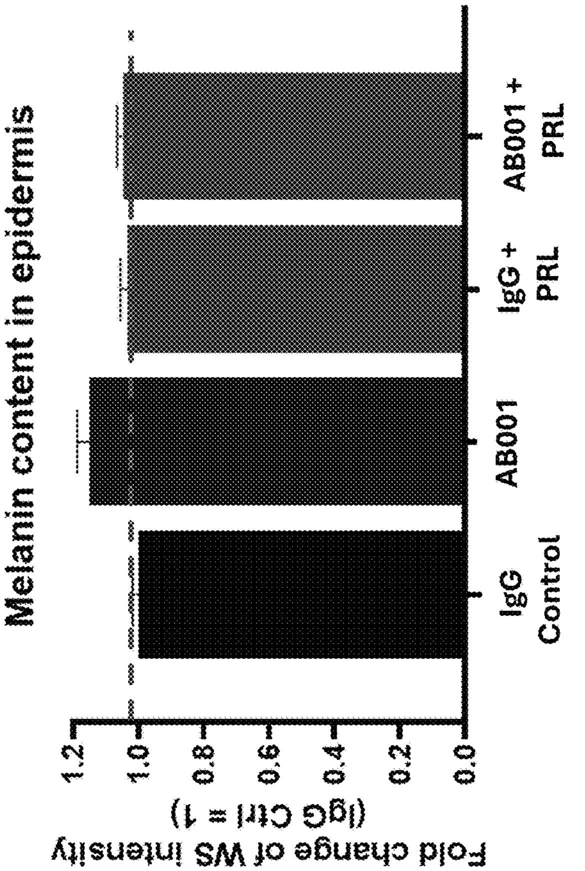
FIGS. 14A-14B is a graph showing fold change in melanin content in anagen phase hair follicles in FIG. 14A and in epidermis in FIG. 14B from ex vivo cultured human male scalp skin treated as indicated and assessed six days post-treatment. Data represents mean SEM; n=14-30 hair follicles from 3 male donors.
Figure 14A:
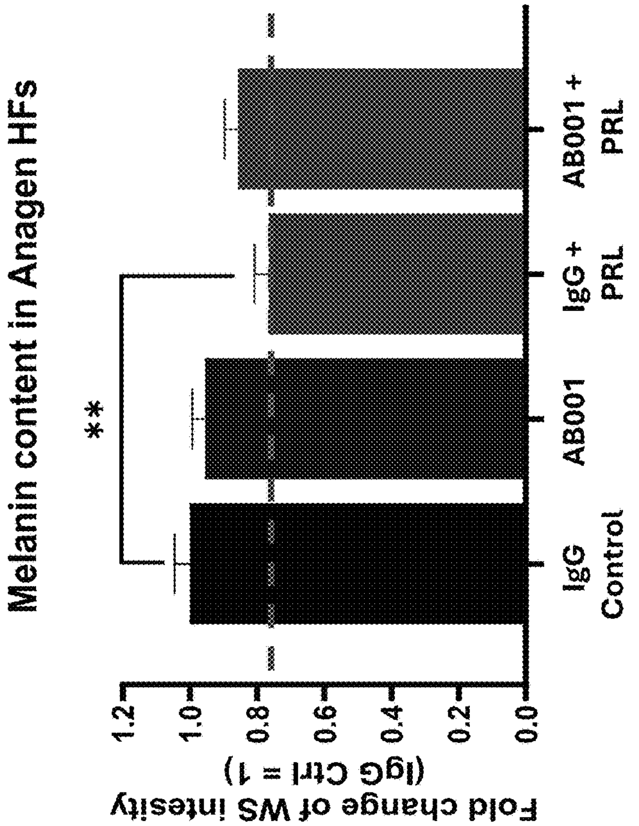

Next, melanin content of treated ex vivo cultures was evaluated by immunostaining. No melanin clumping was observed in AB001-treated samples, indicating a lack of cytotoxicity from the antibody. PRL treatment reduced melanin content of hair follicles in anagen compared to the control, and AB001 rescued the PRL-induced reduction in melanin production observed in anagen VI hair follicles of cultured human male scalp skin (FIG. 14A), demonstrating that AB001 significantly inhibits PRL-mediated suppression of melanogenesis. Further, AB001 alone increased epidermal melanin production in cultured human male scalp skin (FIG. 14B).

Figure 15A:
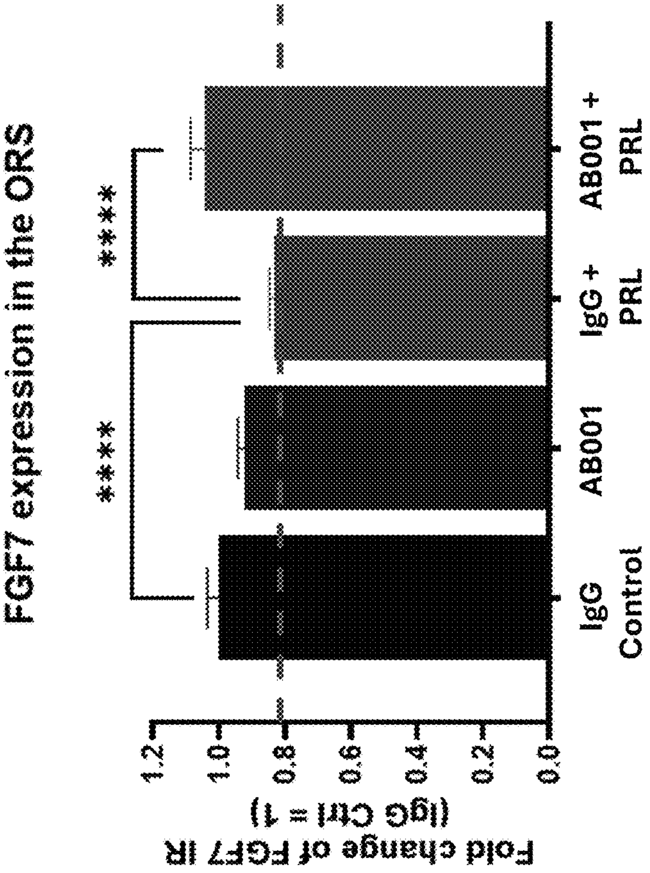
FIGS. 15A-15F are graphs showing fold changes in the expression of molecular markers associated with hair follicle cycling and hair growth, measured in keratinocytes located in the hair matrix, the outer root sheath (ORS) of hair follicles, or fibroblasts in the dermal papilla (DP) from ex vivo cultured human male scalp skin treated as indicated and assessed six days post-treatment.
Figure 15B:
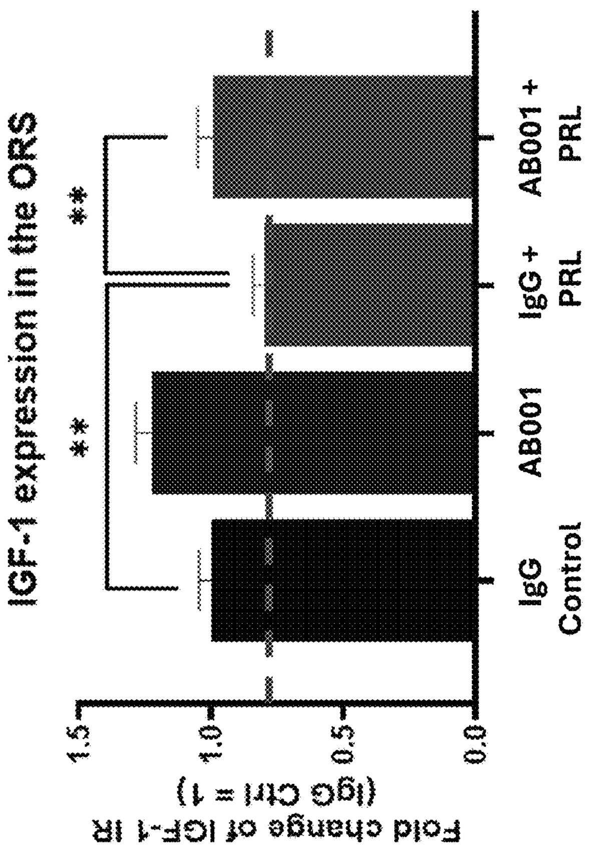
Figure 15C:
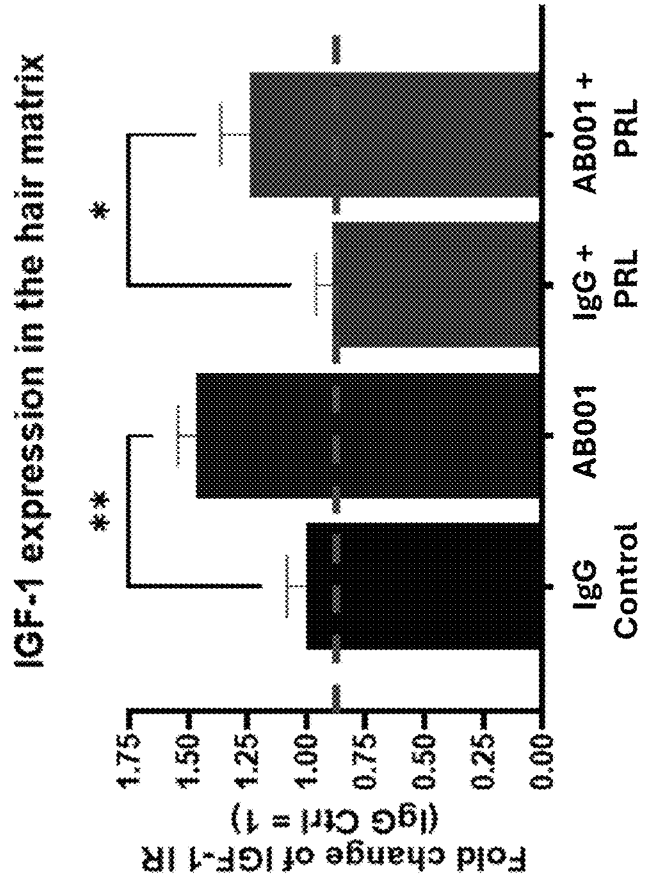
Figure 15D:
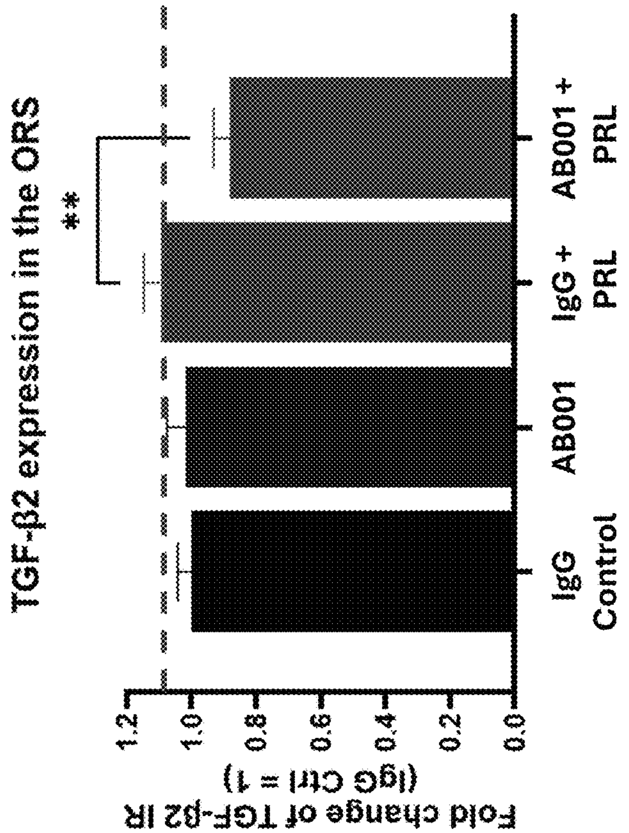
Figure 15E:
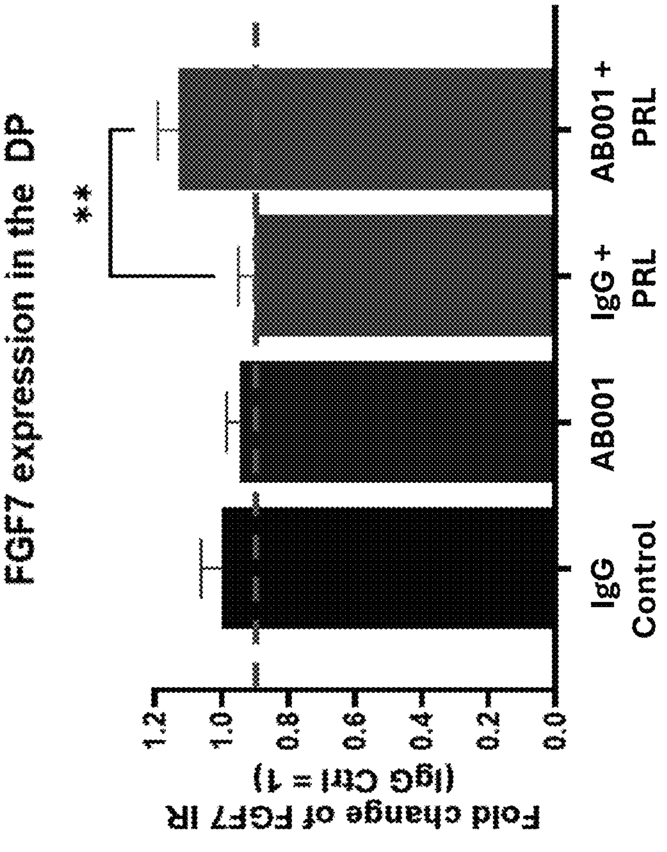
Figure 15F:
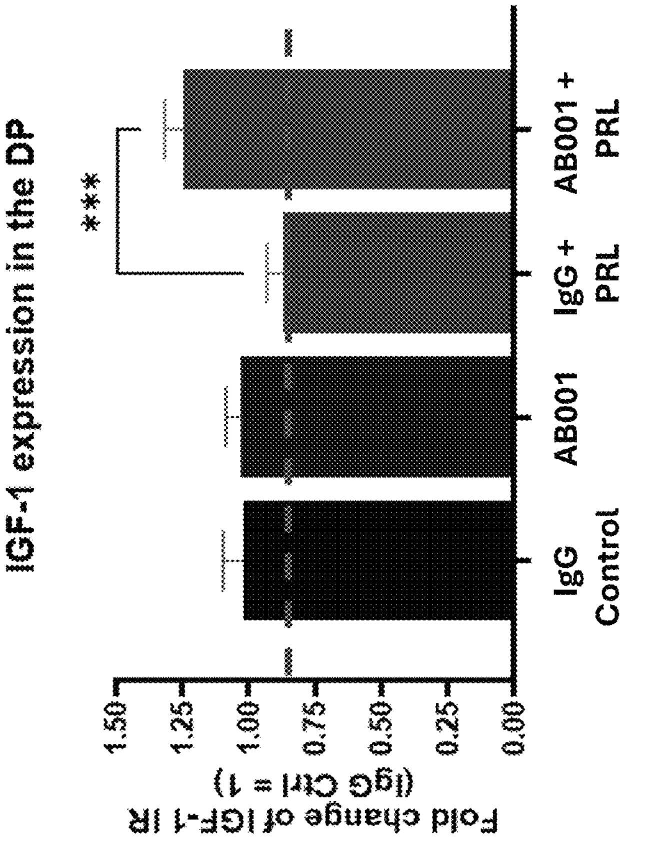

To investigate molecular changes associated with hair follicle cycling and hair growth, expression levels of key signaling molecules and cellular markers were evaluated in the control and treated ex vivo samples by immunofluorescence. This included FGF-7/KGF and IGF-1, which are anagen-prolonging growth factors, and TGFβ2, a growth factor that plays a key role in inducing catagen. In these studies, PRL significantly reduced both FGF7 and IGF-1 expression in keratinocytes from the outer root sheath (ORS) of the hair follicle as compared to their respective controls. AB001 significantly rescued PRL-induced decrease in both FGF-7/KGF and IGF-1 expression in these keratinocytes (FIGS. 15A and 15B). Similarly, AB001 significantly inhibited PRL-induced decrease in FGF7 and IGF-1 expression in dermal papilla (DP) fibroblasts (FIGS. 15E and 15F). Moreover, AB001 alone or in the presence of PRL significantly stimulated IGF-1 expression in the hair matrix keratinocytes (FIG. 15C). In addition, AB001 suppressed the small but notable increase in TGFβ-2 expression by PRL in ORS keratinocytes (FIG. 15D). Taken together, these data suggest that the increase of IGF-1 and FGF-7 expression promote hair growth in presence of PRL.

Figure 16B:
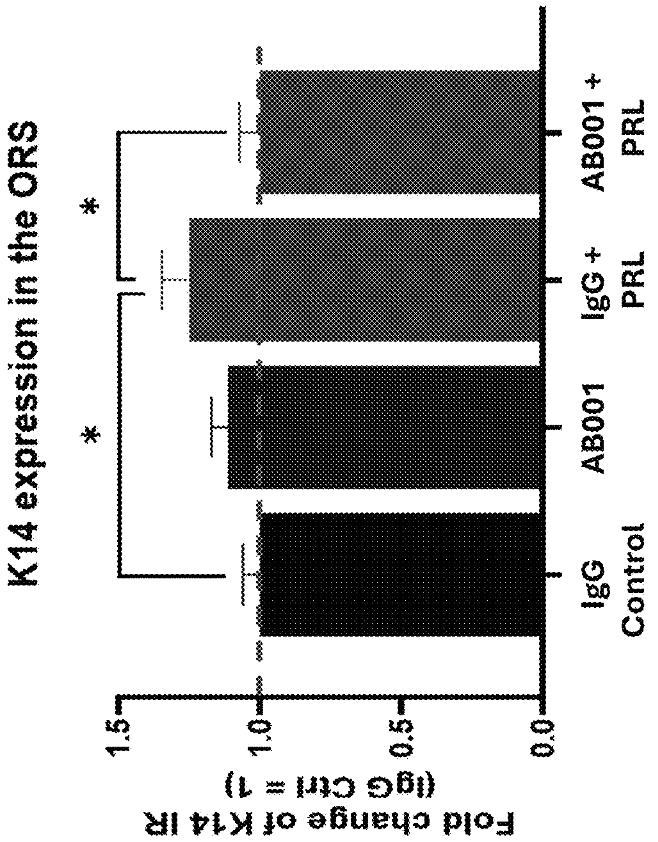
FIGS. 16A-16L are graphs showing fold changes in the expression of molecular markers associated with follicular structure and stem cell status, measured in keratinocytes located in the hair matrix, the outer root sheath (ORS), or in the bulge of hair follicles from ex vivo cultured human male scalp skin treated as indicated and assessed six days post-treatment.
Figure 16A:
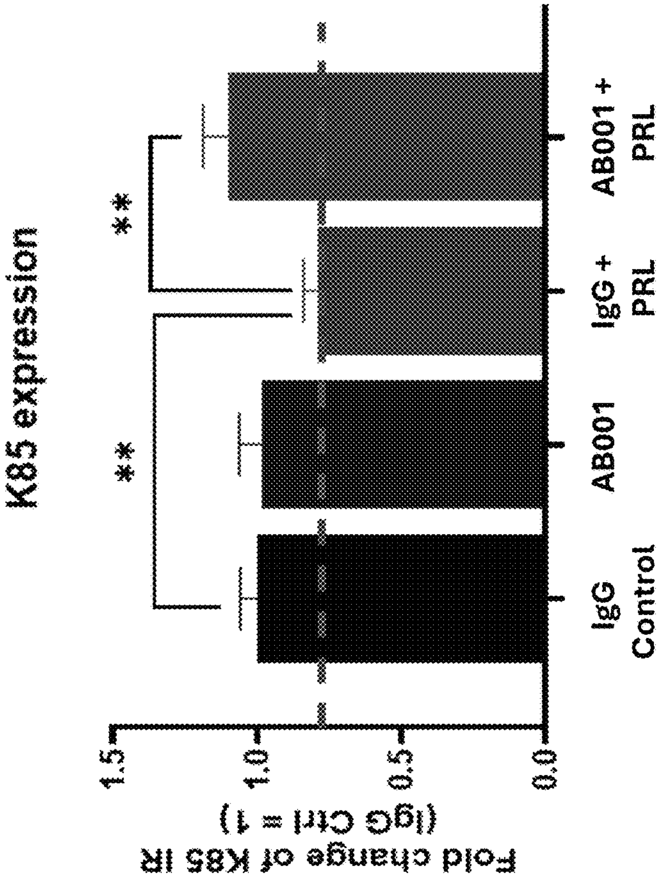
Figure 16C:
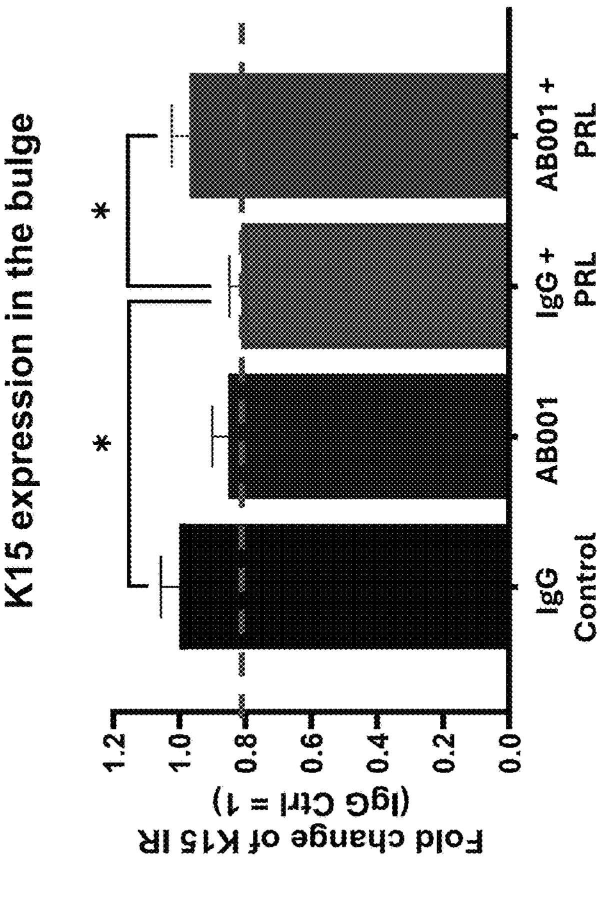
Figure 16D:
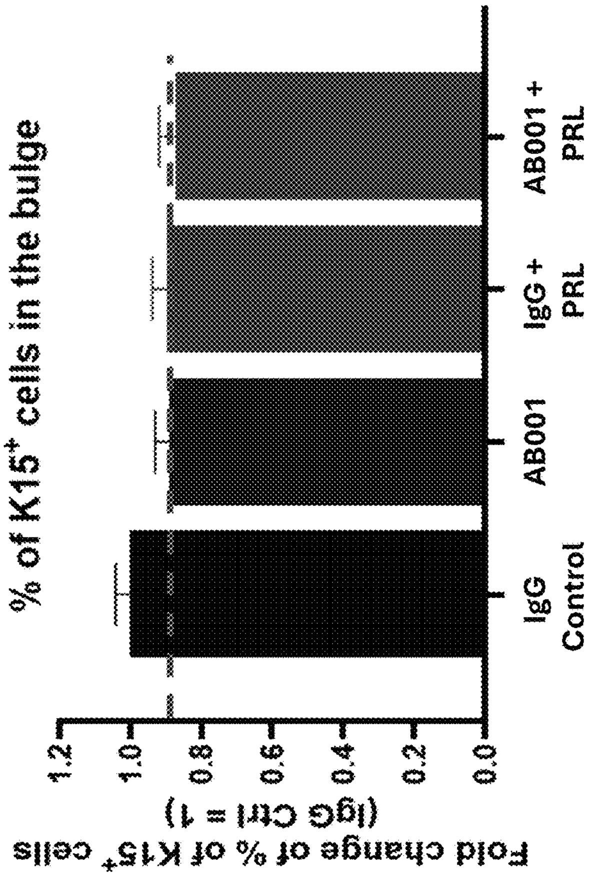
Figure 16F:
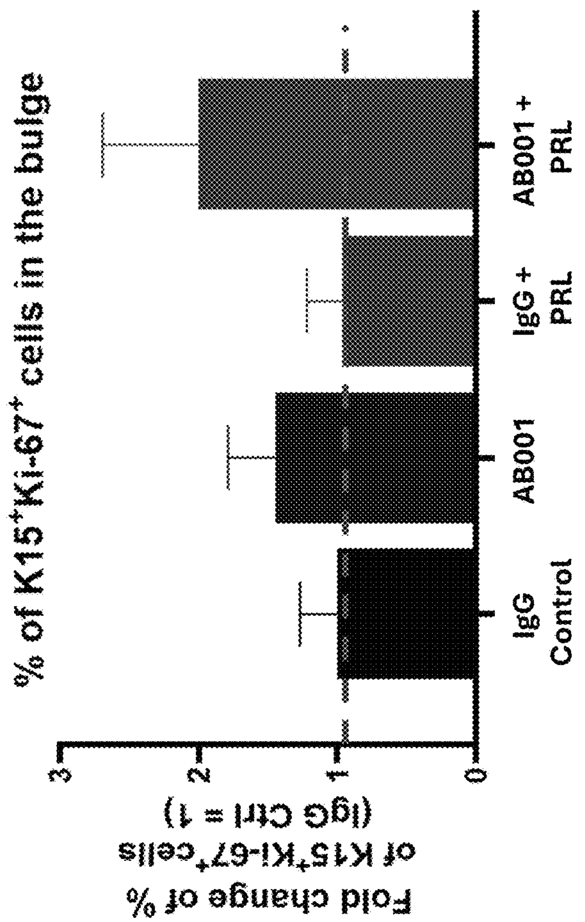
Figure 16E:
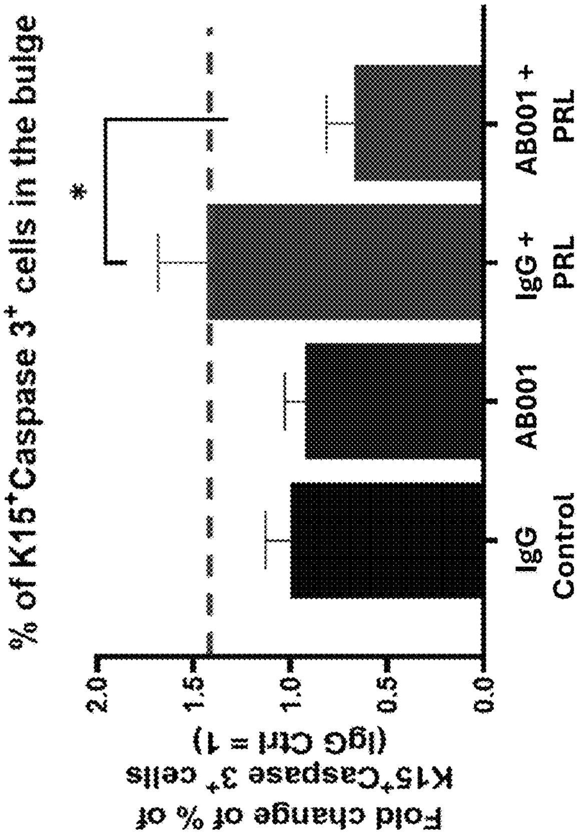
Figure 16G:
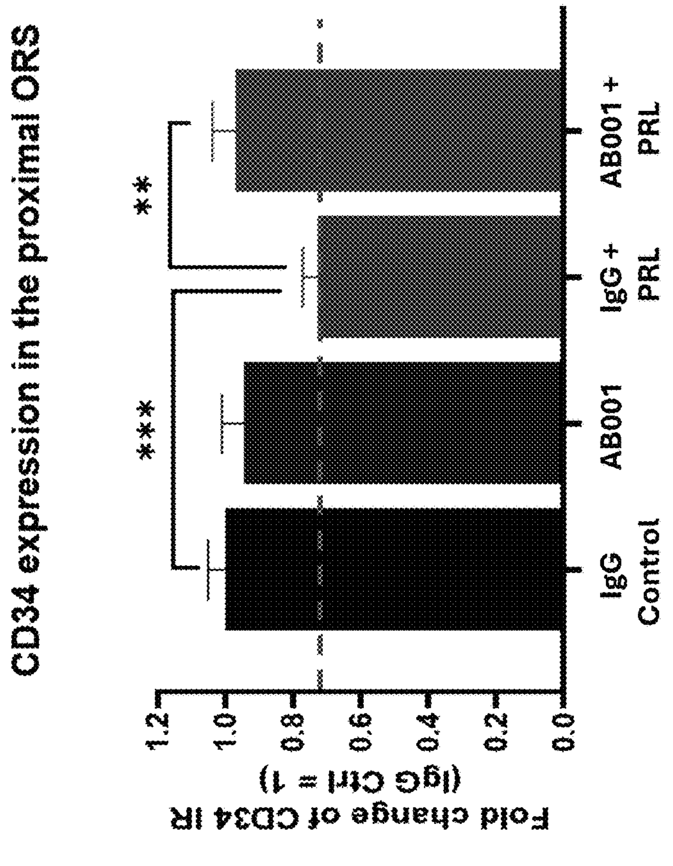
Figure 16H:
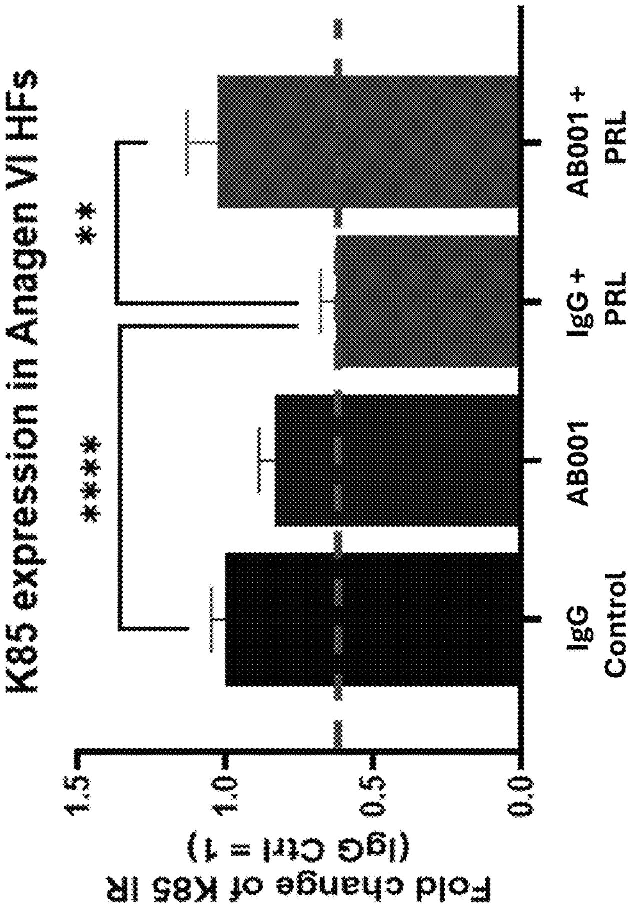
Figure 16J:
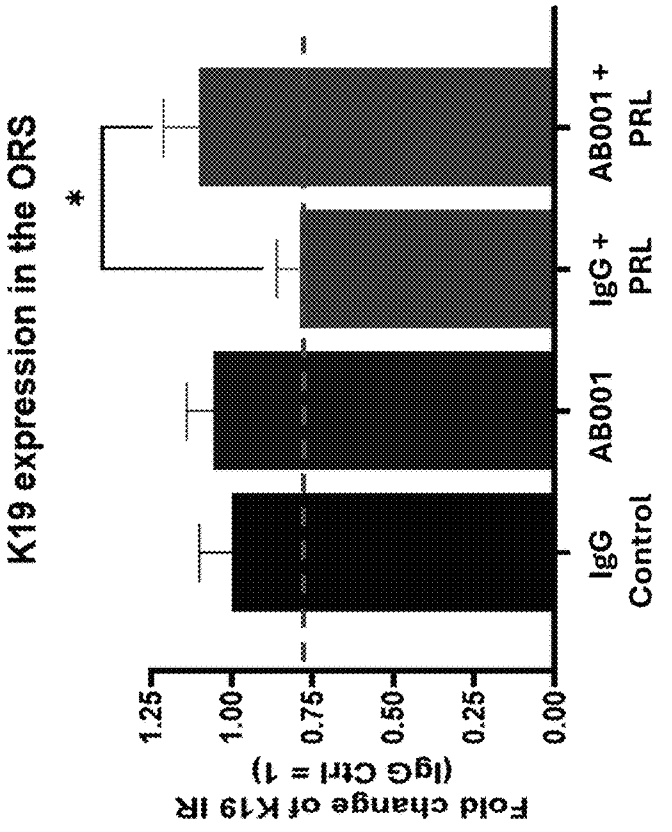
Figure 16I:
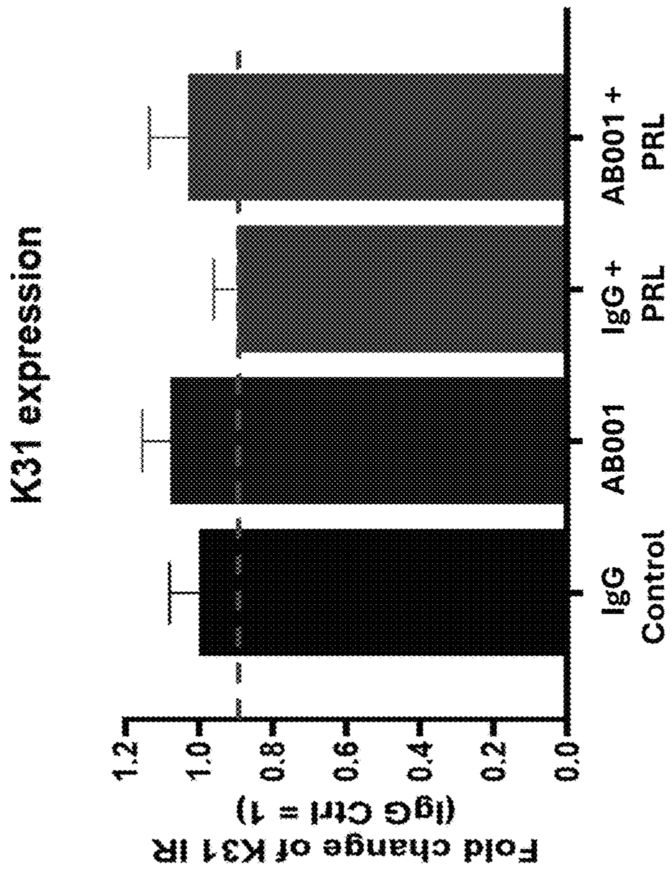
Figure 16K:
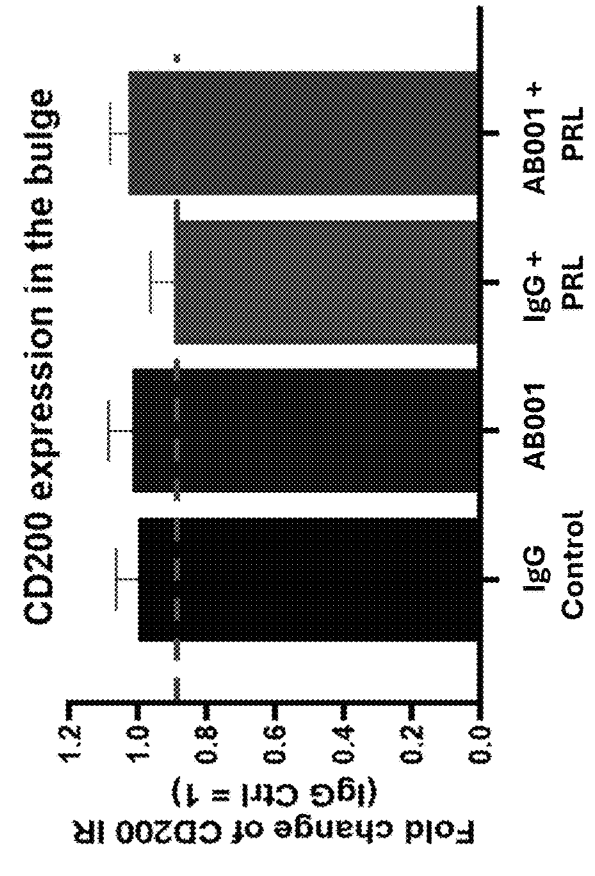
Figure 16L:
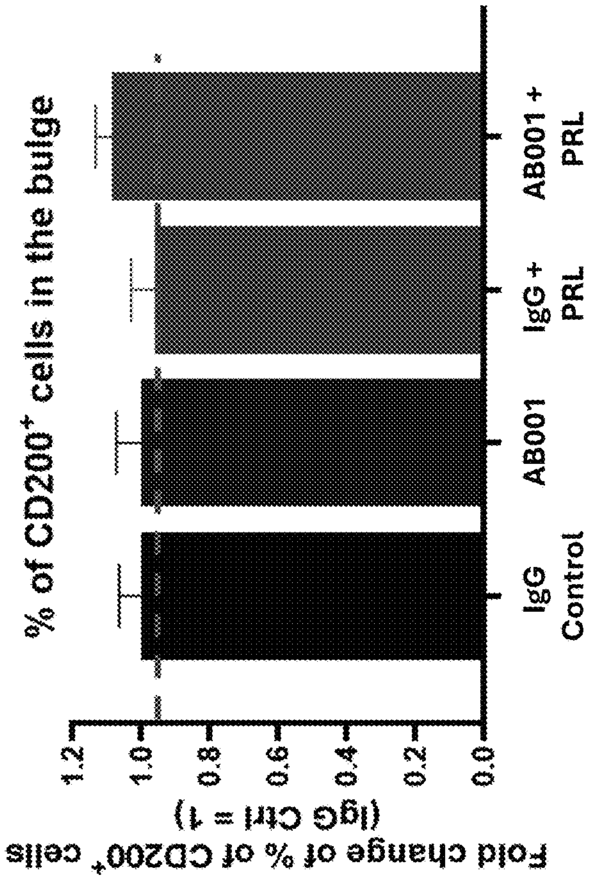

Next, markers of follicular structure and stem cell activity were assessed in the control and treated ex vivo samples by immunofluorescence. AB001 prevented PRL-induced reduction in K85 expression, a marker for hair shaft keratin production. FIGS. 16A and 16H. AB001 inhibited the PRL-induced upregulation of K14, a marker of outer root sheath keratinocytes, and rescued PRL-induced downregulation of K15, a marker of bulge epithelial stem cells, as well as hair cortex K31, and K19, a marker for sub-bulge epithelial stem cells. FIGS. 16B, 16C, 16I, and 16J. These results indicate that AB001 can modulate PRL-mediated changes in keratin expression. In contrast, AB001 did not alter the number of bulge cells expressing K15 in the presence or absence of PRL (FIG. 16D). However, AB001 significantly lowered PRL-induced apoptosis (FIG. 16E) and increased proliferation (FIG. 16F) of K15+ keratinocytes in the bulge. Next, AB001 rescued PRL-induced decrease in CD200 expression in the bulge of hair follicles from cultured human male scalp skin (FIG. 16K). However, no significant change in the number of CD200 positive cells was observed in the bulge (FIG. 16L). Further, AB001 restored PRL-induced decrease in CD34 expression, a marker of bulge epithelial stem cell progeny in the bulge and an important step in the pathogenesis of androgenic alopecia, in keratinocytes from the proximal outer root sheath (ORS) of the hair follicle (FIG. 16G). These data indicate that when co-administrated with PRL, AB001 replenishes the epithelial stem cell pool in the hair follicle, stimulates the differentiation of K15+ cells in CD200+ and/or CD34+ daughter cells and prevents exhaustion.

Figure 17A:
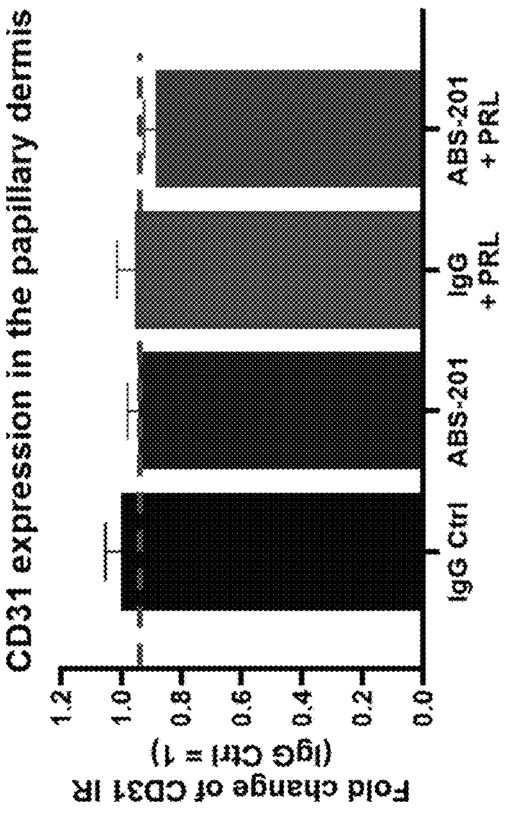
FIGS. 17A-17D are graphs showing the fold changes in the expression of CD31 in the papillary dermis (FIG. 17A) or the change in the number of CD31+ cells in the papillary dermis (FIG. 17B) of hair follicles from ex vivo cultured human male scalp skin treated as indicated and assessed six days post-treatment.
Figure 17B:
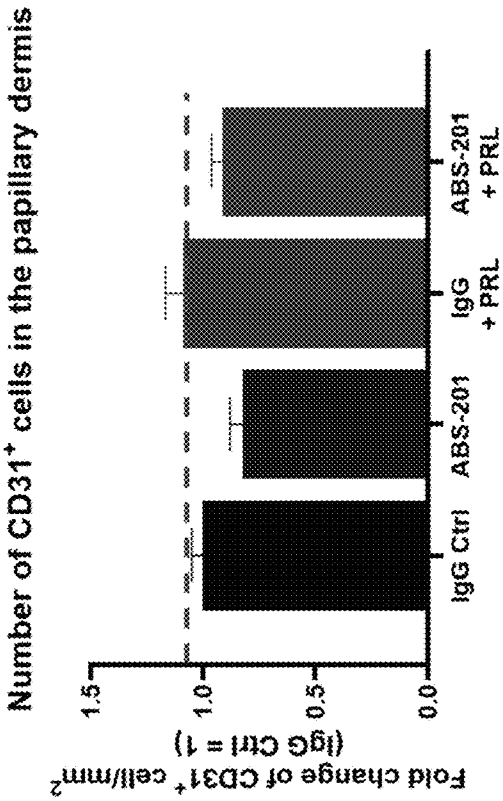
Figure 17C:
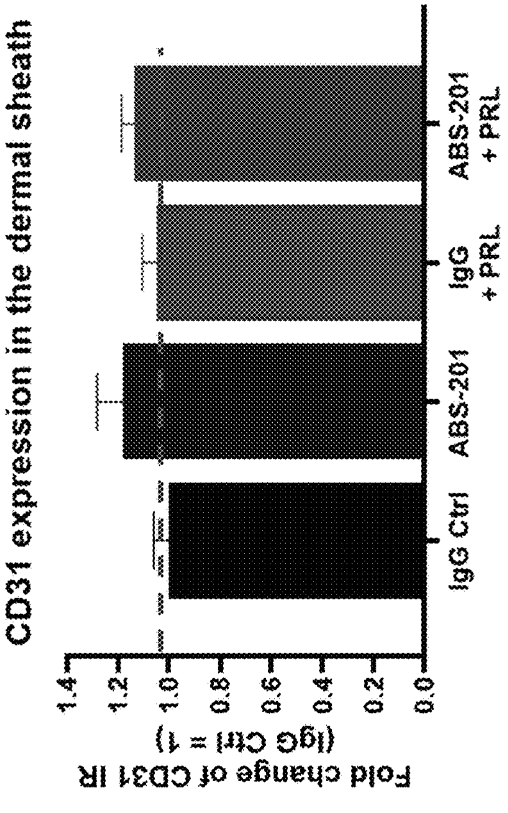
Figure 17D:
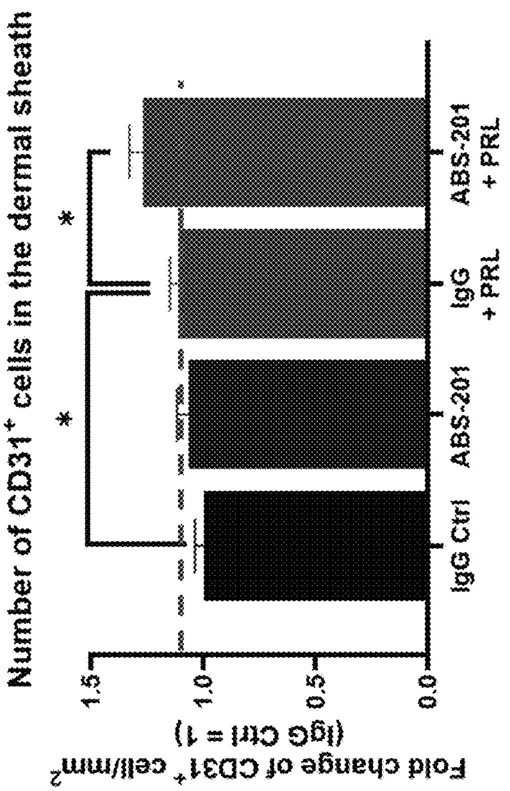
Figure 18A:
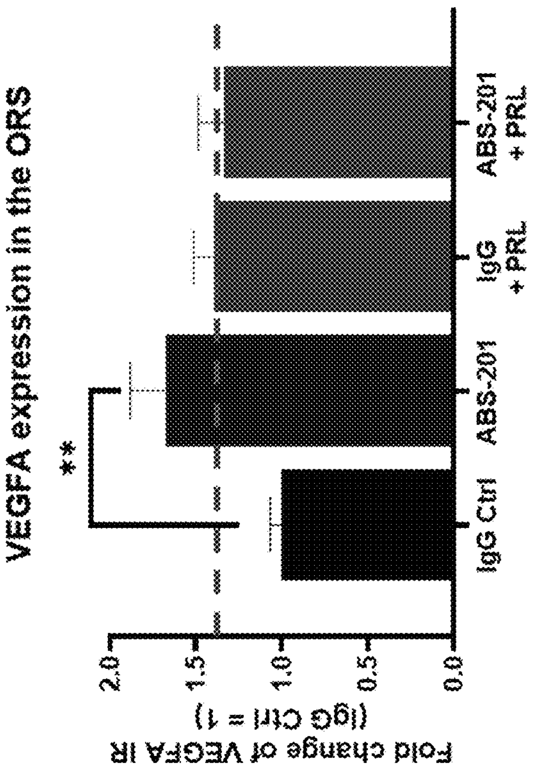
FIGS. 18A-18C are graphs showing fold changes in the expression of VEGFA from the hair follicle from ex vivo cultured human male scalp skin treated as indicated and assessed six days post-treatment.
Figure 18B:
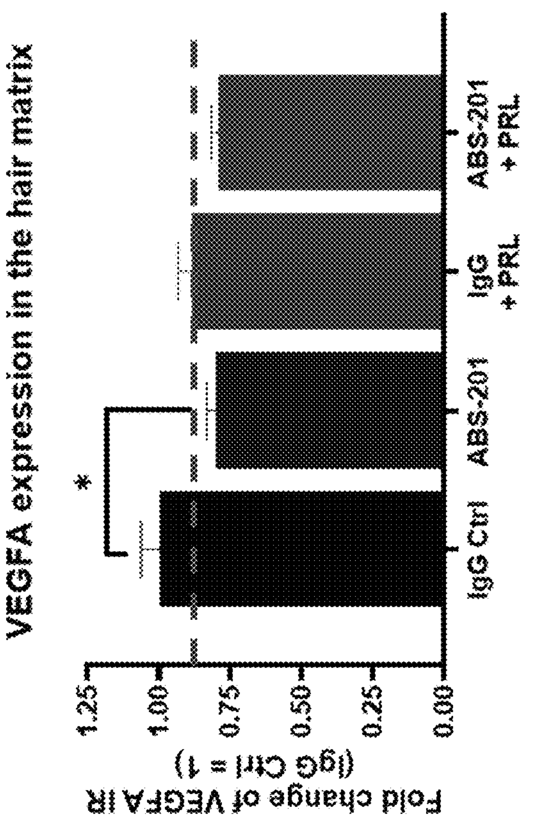
Figure 18C:
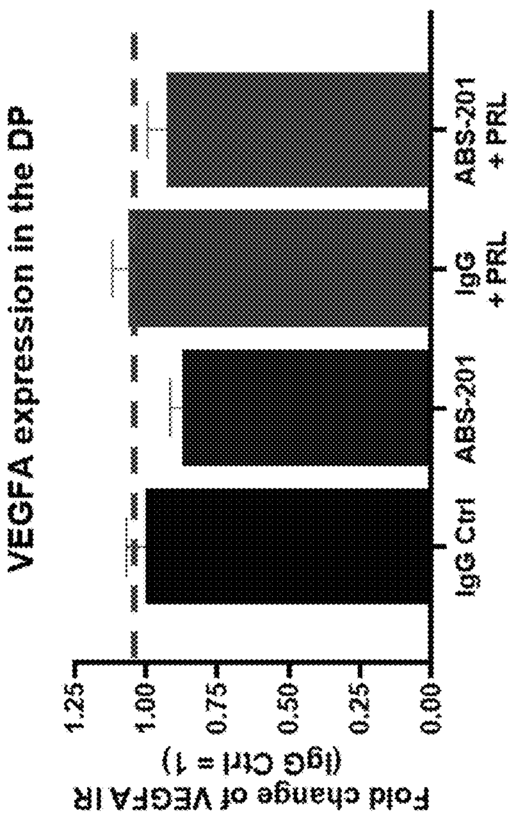

Next, CD31, a marker of intracutaneous angiogenesis, and VEGFA, a key mediator of blood vessel formation in the hair follicle microenvironment, were assessed in the control and treated ex vivo samples. AB001 did not significantly alter CD31 expression or the number of cells expressing CD31 both in the presence or absence of PRL in the papillary dermis of cultured human male scalp skin, nor did it alter CD31 expression in the dermal sheath (FIGS. 17A, 17B, and 17C). In contrast, AB001 significantly increased the number of CD31-positive cells in the dermal sheath in presence of PRL (FIG. 17D). Additionally, AB001 alone significantly stimulated VEGFA expression in the ORS keratinocytes from cultured human male scalp skin (FIG. 18A) and decreased VEGFA expression in the hair matrix (FIG. 18B). These findings suggest that the observed increase in VEGFA expression may not reflect a pro-angiogenic effect but rather indicates an anti-aging effect of AB001 (FIGS. 17A, 17B, and 18A).

Figure 19A:
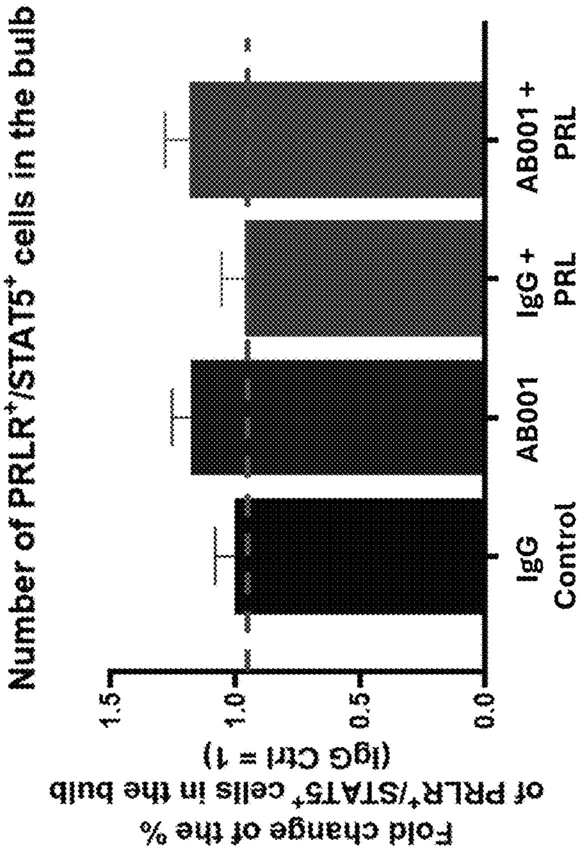
FIGS. 19A-19B are graphs showing fold changes in the number of PRLR/STAT5 positive cells in the bulb of the hair follicle from ex vivo cultured human male scalp skin treated as indicated and assessed six days post-treatment.
Figure 19B:
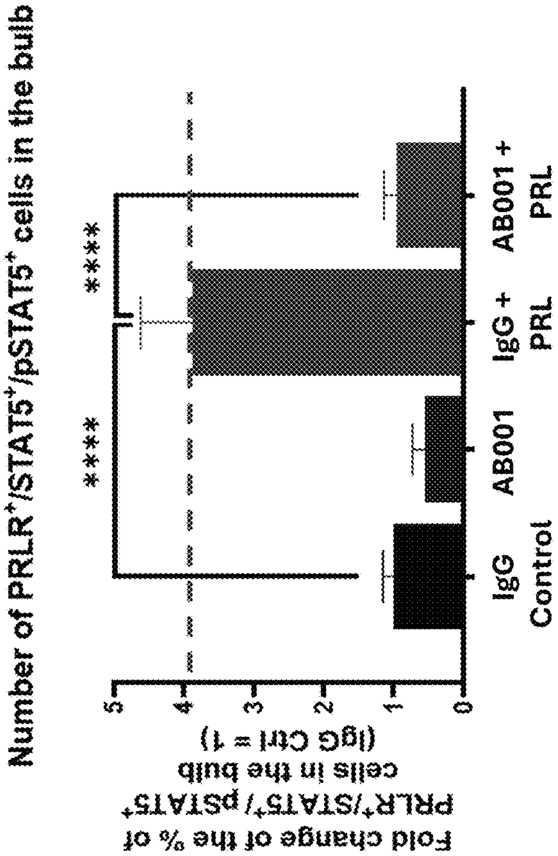

Finally, AB001 significantly prevented activation of the PRLR signaling pathway in hair follicle bulb of cultured human male scalp skin, further demonstrating the efficacy of AB001 in suppressing PRLR activation and downstream signaling (FIGS. 19A and 19B).

In sum, the results from this study demonstrate that AB001 alone promotes hair growth by targeting intrafollicularly produced PRL in human scalp skin. The lack of impact on K15 and K19 expression and cell number demonstrated a selective and restricted effect on PRL/PRL-R signaling by AB001, indicating that AB001 has no deleterious/off-target effect on eHFSCs ex vivo. These findings also indicate that the observed effects on hair growth are due to the local (intrafollicular) action of AB001 rather than a systemic effect, given the absence of PRL in the culture media.

Take together, the results reported in this example indicate that AB001, an exemplary anti-PRLR antibody, exhibited the following bioactivities: (a) prevents the reduction of hair shaft production and the premature catagen induction produced by prolactin ex vivo; (b) inhibits the decrease in FGF-7 and IGF-1 expression but also the increase in TGFb-2 expression induced by prolactin, which altogether may explain the observed anagen prolongation; (c) inhibits the decrease in K85 and K31 expression and the increase in K14 expression induced by prolactin; (d) inhibits the apoptosis of K15+ cells induced by prolactin and may stimulate the proliferation of K15+ cells in the bulge; (e) inhibits the decrease in K19, CD200 and CD34 expression induced by prolactin in the bulge; (f) increased expression of the rejuvenation factor VEGFA, without affecting angiogenesis (no significant changes in CD31 expression or cell number), suggesting an anti-aging effect.

The results reported herein also suggest that anti-PRLR antibodies such as AB001 (e.g., alone) can act as a hair growth promoter by targeting PRL produced intrafollicularly in human scalp skin. It is also suggested that the therapeutic effects of anti-PRLR antibodies such as AB001 alone are due to intrafollicular actions of the antibody rather than systemic effects, since no PRL is present in our culture medium. Further, the absence of negative effects of the anti-PRLR antibody on K15 and K19 expression and cell number compared to the reduction observed with the reported PRL-R antagonist (see, e.g., Ramot et al, FASEB J, 2010) study suggests that the anti-PRLR antibody may have a more restrictive and specific effect on PRL/PRL-R signaling with reduced side/off-target effects.

Example 12: Evaluating Pharmacokinetics Parameters of an Exemplary Anti-PRLR Antibody in Cynomolgus Monkeys This example evaluates in vivo pharmacokinetics of an exemplary anti-PRLR antibody, AB001, in cynomolgus monkeys.

Treatment-naïve female cynomolgus monkeys (approximately 2.5-3.5 years old, weighing 2.5-3.5 kg at study initiation) were enrolled. Animals received a single dose of either AB001, a counterpart of AB001 without half-life extension (HLE) mutations in the constant region (AB001 w/o HLE), or a positive control antibody (AB000) at 100 or 300 mg/kg via subcutaneous (SC) injection or intravenous (IV) infusion. Study dosing scheme is provided in Table 21 below. Whole blood samples were collected over 56 days post administration. Specifically, blood samples were collected pre-dose, and at 1 h, 1.5 h, 2 h, 6 h, 10 h after administration and on Days 2, 3, 4, 6, 15, 22, 29, 36, 43, 50, and 57. Occurrence of anti-drug antibodies (ADA) was noted in a subset of animals across all tested antibodies, doses, and administration routes. ADA-impacted measurement timepoints were excluded from the analysis.

TABLE 21

Study and Dosing Schema

| Group | No. of Animals | Compound ID | Dose Level (mg/kg/dose) | Dose Conc. (mg/mL) | Volume (mL/kg) | Sex | Dose Route |
|---|---|---|---|---|---|---|---|
| 0 | 2 | Vehicle | 0 | 0 | 1.96 | Female | SC |
| 1 | 3 | AB001 | 100 | 50.98 | 1.96 | Female | SC |
| 2 | 3 | AB001 | 100 | 50.98 | 1.96 | Female | IV |
| 3 | 3 | AB001 | 300 | 50.98 | 5.88 | Female | IV |
| 4 | 3 | AB001 w/o HLE | 300 | 54.0 | 5.56 | Female | IV |
| 5 | 3 | AB000 | 300 | 51.8 | 5.79 | Female | IV |

* HLE: Half-life Extension

Figure 20:
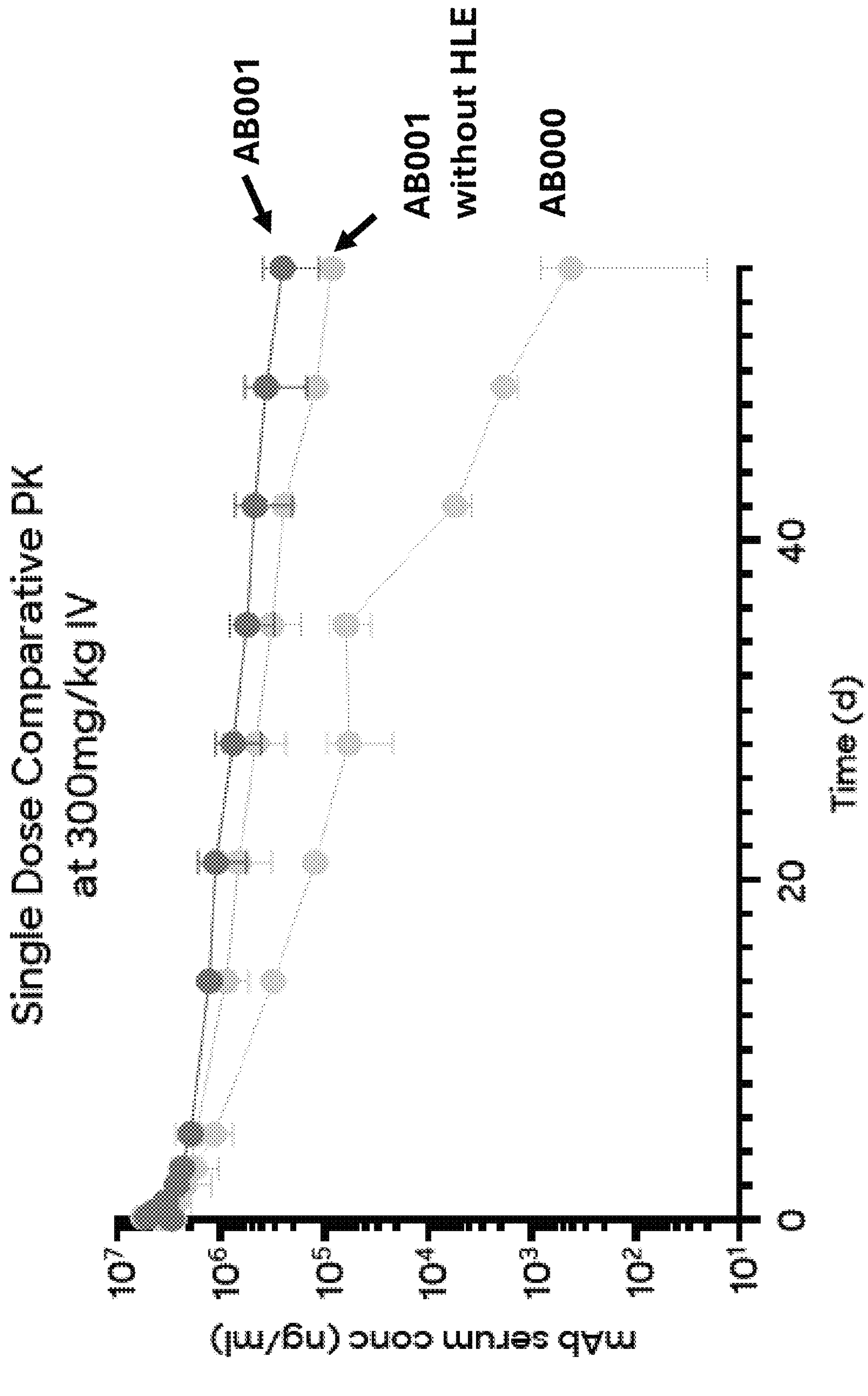
FIG. 20 is a graph showing serum antibody concentration over time following a single dose of the exemplary anti-PRLR antibody AB001 and a counterpart anti-PRLR antibody without half-life extension (HLE), as compared to a control anti-PRLR antibody AB000 in treatment-naïve female cynomolgus monkeys. All antibodies were administered at 300 mg/kg intravenously.

Table 22 summarizes the PK analysis for all antibodies tested in this study. Mean concentration versus time profiles for all tested antibodies are shown in FIG. 20.

TABLE 22

Summary of PK Parameters Analysis at 300 mg/kg Dose

| PK Parameters | ABS-201 | ABS-201 w/o HLE | AB000 |
|---|---|---|---|
| $t_{1/2}$ (d) | 17.1 (16.1-22.0) | 9.1 (1.7-12.5) | 4.3 (3.7-5.4) |
| CL (mL/hr/kg) | 0.206 ± 0.0568 | 0.352 ± 0.176 | 0.653 ± 0.0507 |
| $AUC_{0-\infty}$ (μg*h/mL) | 15.40*10$^5$ ± 4.25*10$^5$ | 9.79*10$^5$ ± 3.82*10$^5$ | 4.61*10$^5$ ± 0.37*10$^5$ |
| Vss (mL/kg) | 112 ± 1.36 | 144 ± 98.5 | 103 ± 11.7 |
| Cmax (μg/ml) | 5610 ± 211 | 6010 ± 326 | 4660 ± 403 |

* $t_{1/2}$ (d): Half-life in days; CL: Clearance; $AUC_{0-\infty}$: Area Under the Curve from Time Zero to Infinity; Vss: Volume of Distribution at Steady State; Cmax: Maximum Observed Concentration Tables 23 and 24 show dose-normalized Cmax, AUC parameters, and dose proportionality analysis of AB001 across the 100 to 300 mg/kg dose.

TABLE 23

| Dose-normalized $C_{max}$ and AUC parameters of AB001 | | | | | | |
|---|---|---|---|---|---|---|
| | | | | Dose Normalization | | |
| Dose (mg/kg) | $C_{max}$ (μg/mL) | $AUC_{0\text{-}336\ h}$ (h*μg/mL) | $AUC_{0\text{-}inf}$ (h*μg/mL) | $C_{max}$/Dose (kg*μg/mL/mg) | $AUC_{0\text{-}336\ h}$/Dose (h*kg*μg/mL/mg) | $AUC_{0\text{-}inf}$/Dose (h*kg*μg/mL/mg) |
| 100 | 1900 | 206000 | 426000 | 19 | 2060 | 4260 |
| 300 | 5610 | 685000 | 1540000 | 19 | 2283 | 5133 |

TABLE 24

| Dose Proportionality Analysis of AB001 from 100 to 300 mg/kg Dose Range | | | | | |
|---|---|---|---|---|---|
| Dependent Variable | Model Variable | Estimate (β) | P-value | 90% CI | Equivalent limits[a] |
| $C_{max}$ (μg/mL) | ln(Dose) | 0.9961 | <0.001 | 0.7794-1.2128 | 0.7968-1.2031 |
| $AUC_{0\text{-}336\ h}$ (h*μg/mL) | ln(Dose) | 1.1087 | <0.001 | 0.8423-1.3751 | 0.7968-1.2031 |

The analysis showed that the exemplary anti-PRLR antibody exhibited the longest apparent terminal half-life ($t_{1/2}$) ranging across analysis methods from 13 days to 17.1 days. On the contrary, the positive control, AB000, had a consistently shorter half-life ranging from 4.2-4.3 days, respectively. Further, exploratory dose proportionality assessment of AB001 indicated that the proportionality coefficients (β) for $C_{max}$ and $AUC_{0\text{-}336\ h}$ were either unity or close to unity. The lower and upper limits of the 90% CI for Cmax were within the acceptance criteria (0.8-1.20); the upper limit of $AUC_{0\text{-}336\ h}$ (1.38) exceeded 1.20, not fully meeting the proportionality bounds.

AB001 also demonstrated a reduced clearance rate compared to the positive control, AB000 (0.21 ml/hr/kg for AB001 as compared to 0.6 ml/hr/kg for AB000). While all tested antibodies showed tmax at 1.5 h post IV administration, AB001 showed a Tmax at 5d post SC administration. No PK liabilities were observed.

Additionally, AB001 demonstrated high absolute bioavailability (>90%) in cynomolgus monkeys as indicated by AUC comparisons between the IV and SC routes at 100 mg/kg ($AUC_{336\ h}$: 91.7% and $AUC_{inf}$: 90.1% respectively).

In sum, AB001 exhibited a favorable PK profile characterized by an extended half-life and reduced clearance compared to the positive control.

Other Embodiments

All of the features disclosed in this specification can be combined in any combination. Each feature disclosed in this specification can be replaced by an alternative feature serving the same, equivalent, or similar purpose. Thus, unless expressly stated otherwise, each feature disclosed is only an example of a generic series of equivalent or similar features.

While the disclosure has been particularly shown and described with reference to specific embodiments (some of which are preferred embodiments), it should be understood by those having skill in the art that various changes in form and detail can be made therein without departing from the spirit and scope of the present disclosure as disclosed herein.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments can be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

SEQUENCE LISTING

```
Sequence total quantity: 146
SEQ ID NO: 1            moltype = AA  length = 5
FEATURE                 Location/Qualifiers
source                  1..5
                        mol_type = protein
                        organism = synthetic construct
SEQUENCE: 1
SYWMH                                                              5

SEQ ID NO: 2            moltype = AA  length = 5
FEATURE                 Location/Qualifiers
source                  1..5
                        mol_type = protein
                        organism = synthetic construct
SEQUENCE: 2
DYWMH                                                              5

SEQ ID NO: 3            moltype = AA  length = 5
FEATURE                 Location/Qualifiers
source                  1..5
                        mol_type = protein
                        organism = synthetic construct
SEQUENCE: 3
DFWMH                                                              5

SEQ ID NO: 4            moltype = AA  length = 5
FEATURE                 Location/Qualifiers
source                  1..5
                        mol_type = protein
                        organism = synthetic construct
SEQUENCE: 4
SYWLH                                                              5

SEQ ID NO: 5            moltype = AA  length = 5
FEATURE                 Location/Qualifiers
source                  1..5
                        mol_type = protein
                        organism = synthetic construct
SEQUENCE: 5
```

-continued

```
SHWLH                                                         5

SEQ ID NO: 6           moltype = AA  length = 17
FEATURE                Location/Qualifiers
source                 1..17
                       mol_type = protein
                       organism = synthetic construct
SEQUENCE: 6
DIARLSSYTN YADSVKG                                           17

SEQ ID NO: 7           moltype = AA  length = 17
FEATURE                Location/Qualifiers
source                 1..17
                       mol_type = protein
                       organism = synthetic construct
SEQUENCE: 7
DISRLKPYTN YADSVKG                                           17

SEQ ID NO: 8           moltype = AA  length = 17
FEATURE                Location/Qualifiers
source                 1..17
                       mol_type = protein
                       organism = synthetic construct
SEQUENCE: 8
DISRLSPYTG YADSVKG                                           17

SEQ ID NO: 9           moltype = AA  length = 17
FEATURE                Location/Qualifiers
source                 1..17
                       mol_type = protein
                       organism = synthetic construct
SEQUENCE: 9
DISRLSPYTN YADSVKG                                           17

SEQ ID NO: 10          moltype = AA  length = 17
FEATURE                Location/Qualifiers
source                 1..17
                       mol_type = protein
                       organism = synthetic construct
SEQUENCE: 10
DISRISPYTN YADSVKG                                           17

SEQ ID NO: 11          moltype = AA  length = 17
FEATURE                Location/Qualifiers
source                 1..17
                       mol_type = protein
                       organism = synthetic construct
SEQUENCE: 11
DISRLSPYHN YADSVKG                                           17

SEQ ID NO: 12          moltype = AA  length = 9
FEATURE                Location/Qualifiers
source                 1..9
                       mol_type = protein
                       organism = synthetic construct
SEQUENCE: 12
GLDARRMDY                                                     9

SEQ ID NO: 13          moltype = AA  length = 9
FEATURE                Location/Qualifiers
source                 1..9
                       mol_type = protein
                       organism = synthetic construct
SEQUENCE: 13
GMDAKRMDH                                                     9

SEQ ID NO: 14          moltype = AA  length = 9
FEATURE                Location/Qualifiers
source                 1..9
                       mol_type = protein
                       organism = synthetic construct
SEQUENCE: 14
GLDARRMSY                                                     9

SEQ ID NO: 15          moltype = AA  length = 9
FEATURE                Location/Qualifiers
source                 1..9
                       mol_type = protein
                       organism = synthetic construct
```

```
SEQUENCE: 15
GMDARRMDY                                                             9

SEQ ID NO: 16          moltype = AA  length = 9
FEATURE                Location/Qualifiers
source                 1..9
                       mol_type = protein
                       organism = synthetic construct
SEQUENCE: 16
GLDARRMDH                                                             9

SEQ ID NO: 17          moltype = AA  length = 14
FEATURE                Location/Qualifiers
source                 1..14
                       mol_type = protein
                       organism = synthetic construct
SEQUENCE: 17
TGSSSNIGAG YVVH                                                       14

SEQ ID NO: 18          moltype = AA  length = 14
FEATURE                Location/Qualifiers
source                 1..14
                       mol_type = protein
                       organism = synthetic construct
SEQUENCE: 18
TGSGTNIGAG YVVH                                                       14

SEQ ID NO: 19          moltype = AA  length = 14
FEATURE                Location/Qualifiers
source                 1..14
                       mol_type = protein
                       organism = synthetic construct
SEQUENCE: 19
TGSSSNLGAG YVNH                                                       14

SEQ ID NO: 20          moltype = AA  length = 14
FEATURE                Location/Qualifiers
source                 1..14
                       mol_type = protein
                       organism = synthetic construct
SEQUENCE: 20
TGSSTNLGAG YVVH                                                       14

SEQ ID NO: 21          moltype = AA  length = 14
FEATURE                Location/Qualifiers
source                 1..14
                       mol_type = protein
                       organism = synthetic construct
SEQUENCE: 21
TGSSSNLGGG YVVH                                                       14

SEQ ID NO: 22          moltype = AA  length = 14
FEATURE                Location/Qualifiers
source                 1..14
                       mol_type = protein
                       organism = synthetic construct
SEQUENCE: 22
TGSASNIGAG YVVH                                                       14

SEQ ID NO: 23          moltype = AA  length = 14
FEATURE                Location/Qualifiers
source                 1..14
                       mol_type = protein
                       organism = synthetic construct
SEQUENCE: 23
TGSSSNIGHG YVVH                                                       14

SEQ ID NO: 24          moltype = AA  length = 14
FEATURE                Location/Qualifiers
source                 1..14
                       mol_type = protein
                       organism = synthetic construct
SEQUENCE: 24
TGSSSNLGAG YVVH                                                       14

SEQ ID NO: 25          moltype = AA  length = 14
FEATURE                Location/Qualifiers
source                 1..14
                       mol_type = protein
```

```
                        organism = synthetic construct
SEQUENCE: 25
TGSTSNLGAG YVVH                                                      14

SEQ ID NO: 26           moltype = AA  length = 14
FEATURE                 Location/Qualifiers
source                  1..14
                        mol_type = protein
                        organism = synthetic construct
SEQUENCE: 26
TGSSSNIGGG YVVH                                                      14

SEQ ID NO: 27           moltype = AA  length = 14
FEATURE                 Location/Qualifiers
source                  1..14
                        mol_type = protein
                        organism = synthetic construct
SEQUENCE: 27
TGSSSNIHGG YVVH                                                      14

SEQ ID NO: 28           moltype = AA  length = 7
FEATURE                 Location/Qualifiers
source                  1..7
                        mol_type = protein
                        organism = synthetic construct
SEQUENCE: 28
RNNQRPS                                                              7

SEQ ID NO: 29           moltype = AA  length = 7
FEATURE                 Location/Qualifiers
source                  1..7
                        mol_type = protein
                        organism = synthetic construct
SEQUENCE: 29
RNNLRPS                                                              7

SEQ ID NO: 30           moltype = AA  length = 7
FEATURE                 Location/Qualifiers
source                  1..7
                        mol_type = protein
                        organism = synthetic construct
SEQUENCE: 30
RNNVRPS                                                              7

SEQ ID NO: 31           moltype = AA  length = 7
FEATURE                 Location/Qualifiers
source                  1..7
                        mol_type = protein
                        organism = synthetic construct
SEQUENCE: 31
RHHQRPS                                                              7

SEQ ID NO: 32           moltype = AA  length = 7
FEATURE                 Location/Qualifiers
source                  1..7
                        mol_type = protein
                        organism = synthetic construct
SEQUENCE: 32
RHHQKPS                                                              7

SEQ ID NO: 33           moltype = AA  length = 11
FEATURE                 Location/Qualifiers
source                  1..11
                        mol_type = protein
                        organism = synthetic construct
SEQUENCE: 33
AAWDDSLNGW L                                                         11

SEQ ID NO: 34           moltype = AA  length = 11
FEATURE                 Location/Qualifiers
source                  1..11
                        mol_type = protein
                        organism = synthetic construct
SEQUENCE: 34
ASWDDRHQAW L                                                         11

SEQ ID NO: 35           moltype = AA  length = 11
FEATURE                 Location/Qualifiers
source                  1..11
```

```
                        mol_type = protein
                        organism = synthetic construct
SEQUENCE: 35
ASWDDSLQAW L                                                    11

SEQ ID NO: 36           moltype = AA  length = 11
FEATURE                 Location/Qualifiers
source                  1..11
                        mol_type = protein
                        organism = synthetic construct
SEQUENCE: 36
ASWDDHSSAW L                                                    11

SEQ ID NO: 37           moltype = AA  length = 11
FEATURE                 Location/Qualifiers
source                  1..11
                        mol_type = protein
                        organism = synthetic construct
SEQUENCE: 37
AAWDDSVSGW L                                                    11

SEQ ID NO: 38           moltype = AA  length = 11
FEATURE                 Location/Qualifiers
source                  1..11
                        mol_type = protein
                        organism = synthetic construct
SEQUENCE: 38
ASWDDSLQGW L                                                    11

SEQ ID NO: 39           moltype = AA  length = 11
FEATURE                 Location/Qualifiers
source                  1..11
                        mol_type = protein
                        organism = synthetic construct
SEQUENCE: 39
AAWDDHRTAW L                                                    11

SEQ ID NO: 40           moltype = AA  length = 11
FEATURE                 Location/Qualifiers
source                  1..11
                        mol_type = protein
                        organism = synthetic construct
SEQUENCE: 40
ASWDDSHMAW L                                                    11

SEQ ID NO: 41           moltype = AA  length = 11
FEATURE                 Location/Qualifiers
source                  1..11
                        mol_type = protein
                        organism = synthetic construct
SEQUENCE: 41
AAWDDERNGW L                                                    11

SEQ ID NO: 42           moltype = AA  length = 11
FEATURE                 Location/Qualifiers
source                  1..11
                        mol_type = protein
                        organism = synthetic construct
SEQUENCE: 42
AAHDDELHGW L                                                    11

SEQ ID NO: 43           moltype = AA  length = 11
FEATURE                 Location/Qualifiers
source                  1..11
                        mol_type = protein
                        organism = synthetic construct
SEQUENCE: 43
AAWDDSRNGW L                                                    11

SEQ ID NO: 44           moltype = AA  length = 30
FEATURE                 Location/Qualifiers
source                  1..30
                        mol_type = protein
                        organism = synthetic construct
SEQUENCE: 44
EVQLLESGGG LVQPGGSLRL SCAASGFTFS                                30

SEQ ID NO: 45           moltype = AA  length = 30
FEATURE                 Location/Qualifiers
```

```
source                  1..30
                        mol_type = protein
                        organism = synthetic construct
SEQUENCE: 45
QVQLVQSGGG LVQPGGSLRL SCAASGFTYS                                    30

SEQ ID NO: 46           moltype = AA  length = 30
FEATURE                 Location/Qualifiers
source                  1..30
                        mol_type = protein
                        organism = synthetic construct
SEQUENCE: 46
QVQLVQSGGG LVQPGGSLRL SCAASGFSYS                                    30

SEQ ID NO: 47           moltype = AA  length = 30
FEATURE                 Location/Qualifiers
source                  1..30
                        mol_type = protein
                        organism = synthetic construct
SEQUENCE: 47
QVQLVQSGGG LVQPGGSLRL SCAASGFSYV                                    30

SEQ ID NO: 48           moltype = AA  length = 30
FEATURE                 Location/Qualifiers
source                  1..30
                        mol_type = protein
                        organism = synthetic construct
SEQUENCE: 48
QVQLVQSGGG LVQPGGSLRL SCAASGFTHH                                    30

SEQ ID NO: 49           moltype = AA  length = 14
FEATURE                 Location/Qualifiers
source                  1..14
                        mol_type = protein
                        organism = synthetic construct
SEQUENCE: 49
WVRQAPGKGL EWVS                                                     14

SEQ ID NO: 50           moltype = AA  length = 14
FEATURE                 Location/Qualifiers
source                  1..14
                        mol_type = protein
                        organism = synthetic construct
SEQUENCE: 50
WVRQAPGKGL EWMS                                                     14

SEQ ID NO: 51           moltype = AA  length = 33
FEATURE                 Location/Qualifiers
source                  1..33
                        mol_type = protein
                        organism = synthetic construct
SEQUENCE: 51
GRFTISRDNS KNTLYLQMNS LRAEDTAVYY CAR                                33

SEQ ID NO: 52           moltype = AA  length = 33
FEATURE                 Location/Qualifiers
source                  1..33
                        mol_type = protein
                        organism = synthetic construct
SEQUENCE: 52
GRFTISRDNA KNTLYLQLNS LRAEDTAMYY CAR                                33

SEQ ID NO: 53           moltype = AA  length = 33
FEATURE                 Location/Qualifiers
source                  1..33
                        mol_type = protein
                        organism = synthetic construct
SEQUENCE: 53
GRFTISRDNA KNTLYLQLNS LRAEDTAMYY CAK                                33

SEQ ID NO: 54           moltype = AA  length = 33
FEATURE                 Location/Qualifiers
source                  1..33
                        mol_type = protein
                        organism = synthetic construct
SEQUENCE: 54
GRFTISRDNA KNTLYLQLNS LRAEDTAMYY CSR                                33

SEQ ID NO: 55           moltype = AA  length = 11
```

```
FEATURE                Location/Qualifiers
source                 1..11
                       mol_type = protein
                       organism = synthetic construct
SEQUENCE: 55
WGQGTLVTVS S                                                          11

SEQ ID NO: 56          moltype = AA  length = 22
FEATURE                Location/Qualifiers
source                 1..22
                       mol_type = protein
                       organism = synthetic construct
SEQUENCE: 56
QSVLTQPPSA SGTPGQRVTI SC                                              22

SEQ ID NO: 57          moltype = AA  length = 23
FEATURE                Location/Qualifiers
source                 1..23
                       mol_type = protein
                       organism = synthetic construct
SEQUENCE: 57
DIQLTQSPSS VSVSVGERVT IDC                                             23

SEQ ID NO: 58          moltype = AA  length = 15
FEATURE                Location/Qualifiers
source                 1..15
                       mol_type = protein
                       organism = synthetic construct
SEQUENCE: 58
WYQQLPGTAP KLLIY                                                      15

SEQ ID NO: 59          moltype = AA  length = 15
FEATURE                Location/Qualifiers
source                 1..15
                       mol_type = protein
                       organism = synthetic construct
SEQUENCE: 59
WYQQKPGQAP QLLIY                                                      15

SEQ ID NO: 60          moltype = AA  length = 15
FEATURE                Location/Qualifiers
source                 1..15
                       mol_type = protein
                       organism = synthetic construct
SEQUENCE: 60
WYQQKPGQAP QLKIY                                                      15

SEQ ID NO: 61          moltype = AA  length = 15
FEATURE                Location/Qualifiers
source                 1..15
                       mol_type = protein
                       organism = synthetic construct
SEQUENCE: 61
WYQQKPGQAP QLLIF                                                      15

SEQ ID NO: 62          moltype = AA  length = 15
FEATURE                Location/Qualifiers
source                 1..15
                       mol_type = protein
                       organism = synthetic construct
SEQUENCE: 62
WYQQKPGQAP QHLIY                                                      15

SEQ ID NO: 63          moltype = AA  length = 32
FEATURE                Location/Qualifiers
source                 1..32
                       mol_type = protein
                       organism = synthetic construct
SEQUENCE: 63
GVPDRFSGSK SGTSASLAIS GLRSEDEADY YC                                   32

SEQ ID NO: 64          moltype = AA  length = 32
FEATURE                Location/Qualifiers
source                 1..32
                       mol_type = protein
                       organism = synthetic construct
SEQUENCE: 64
GVPDRFSGSK SGTDATLTIS SLQAEDAAVY YC                                   32
```

```
SEQ ID NO: 65          moltype = AA  length = 10
FEATURE                Location/Qualifiers
source                 1..10
                       mol_type = protein
                       organism = synthetic construct
SEQUENCE: 65
FGGGTKLTVL                                                        10

SEQ ID NO: 66          moltype = AA  length = 10
FEATURE                Location/Qualifiers
source                 1..10
                       mol_type = protein
                       organism = synthetic construct
SEQUENCE: 66
FGQGTKLEIK                                                        10

SEQ ID NO: 67          moltype = AA  length = 118
FEATURE                Location/Qualifiers
source                 1..118
                       mol_type = protein
                       organism = synthetic construct
SEQUENCE: 67
EVQLLESGGG LVQPGGSLRL SCAASGFTFS SYWMHWVRQA PGKGLEWVSD IARLSSYTNY  60
ADSVKGRFTI SRDNSKNTLY LQMNSLRAED TAVYYCARGL DARRMDYWGQ GTLVTVSS    118

SEQ ID NO: 68          moltype = AA  length = 118
FEATURE                Location/Qualifiers
source                 1..118
                       mol_type = protein
                       organism = synthetic construct
SEQUENCE: 68
QVQLVQSGGG LVQPGGSLRL SCAASGFTYS DYWMHWVRQA PGKGLEWVSD ISRLKPYTNY  60
ADSVKGRFTI SRDNAKNTLY LQLNSLRAED TAMYYCARGL DARRMDYWGQ GTLVTVSS    118

SEQ ID NO: 69          moltype = AA  length = 118
FEATURE                Location/Qualifiers
source                 1..118
                       mol_type = protein
                       organism = synthetic construct
SEQUENCE: 69
QVQLVQSGGG LVQPGGSLRL SCAASGFSYS SYWMHWVRQA PGKGLEWVSD ISRLSPYTGY  60
ADSVKGRFTI SRDNAKNTLY LQLNSLRAED TAMYYCARGM DAKRMDHWGQ GTLVTVSS    118

SEQ ID NO: 70          moltype = AA  length = 118
FEATURE                Location/Qualifiers
source                 1..118
                       mol_type = protein
                       organism = synthetic construct
SEQUENCE: 70
QVQLVQSGGG LVQPGGSLRL SCAASGFTYS DFWMHWVRQA PGKGLEWMSD ISRLSPYTNY  60
ADSVKGRFTI SRDNAKNTLY LQLNSLRAED TAMYYCARGL DARRMDYWGQ GTLVTVSS    118

SEQ ID NO: 71          moltype = AA  length = 118
FEATURE                Location/Qualifiers
source                 1..118
                       mol_type = protein
                       organism = synthetic construct
SEQUENCE: 71
QVQLVQSGGG LVQPGGSLRL SCAASGFSYV SYWMHWVRQA PGKGLEWVSD ISRISPYTNY  60
ADSVKGRFTI SRDNAKNTLY LQLNSLRAED TAMYYCARGL DARRMDYWGQ GTLVTVSS    118

SEQ ID NO: 72          moltype = AA  length = 118
FEATURE                Location/Qualifiers
source                 1..118
                       mol_type = protein
                       organism = synthetic construct
SEQUENCE: 72
QVQLVQSGGG LVQPGGSLRL SCAASGFTYS DYWMHWVRQA PGKGLEWMSD ISRLSPYTGY  60
ADSVKGRFTI SRDNAKNTLY LQLNSLRAED TAMYYCARGL DARRMDYWGQ GTLVTVSS    118

SEQ ID NO: 73          moltype = AA  length = 118
FEATURE                Location/Qualifiers
source                 1..118
                       mol_type = protein
                       organism = synthetic construct
SEQUENCE: 73
QVQLVQSGGG LVQPGGSLRL SCAASGFSYS DYWMHWVRQA PGKGLEWVSD ISRLSPYTNY  60
ADSVKGRFTI SRDNAKNTLY LQLNSLRAED TAMYYCARGL DARRMSYWGQ GTLVTVSS    118
```

```
SEQ ID NO: 74           moltype = AA  length = 17
FEATURE                 Location/Qualifiers
source                  1..17
                        mol_type = protein
                        organism = synthetic construct
VARIANT                 6
                        note = X is K or S.
VARIANT                 10
                        note = X is G or N.
SEQUENCE: 74
DISRLXPYTX YADSVKG                                                17

SEQ ID NO: 75           moltype = AA  length = 118
FEATURE                 Location/Qualifiers
source                  1..118
                        mol_type = protein
                        organism = synthetic construct
SEQUENCE: 75
QVQLVQSGGG LVQPGGSLRL SCAASGFTHH SYWLHWVRQA PGKGLEWVSD ISRLSPYTNY  60
ADSVKGRFTI SRDNAKNTLY LQLNSLRAED TAMYYCARGM DARRMDYWGQ GTLVTVSS    118

SEQ ID NO: 76           moltype = AA  length = 17
FEATURE                 Location/Qualifiers
source                  1..17
                        mol_type = protein
                        organism = synthetic construct
VARIANT                 6
                        note = X is K or S.
SEQUENCE: 76
DISRLXPYTN YADSVKG                                                17

SEQ ID NO: 77           moltype = AA  length = 118
FEATURE                 Location/Qualifiers
source                  1..118
                        mol_type = protein
                        organism = synthetic construct
SEQUENCE: 77
QVQLVQSGGG LVQPGGSLRL SCAASGFTYS SHWLHWVRQA PGKGLEWVSD ISRLSPYTNY  60
ADSVKGRFTI SRDNAKNTLY LQLNSLRAED TAMYYCAKGL DARRMDHWGQ GTLVTVSS    118

SEQ ID NO: 78           moltype = AA  length = 118
FEATURE                 Location/Qualifiers
source                  1..118
                        mol_type = protein
                        organism = synthetic construct
SEQUENCE: 78
QVQLVQSGGG LVQPGGSLRL SCAASGFTHS SYWMHWVRQA PGKGLEWVSD ISRLSPYHNY  60
ADSVKGRFTI SRDNAKNTLY LQLNSLRAED TAMYYCSRGL DARRMDYWGQ GTLVTVSS    118

SEQ ID NO: 79           moltype = AA  length = 118
FEATURE                 Location/Qualifiers
source                  1..118
                        mol_type = protein
                        organism = synthetic construct
SEQUENCE: 79
QVQLVQSGGG LVQPGGSLRL SCAASGFTHH SYWLHWVRQA PGKGLEWVSD ISRLSPYTNY  60
ADSVKGRFTI SRDNAKNTLY LQLNSLRAED TAMYYCARGM DARRMDYWGQ GTLVTVSS    118

SEQ ID NO: 80           moltype = AA  length = 118
FEATURE                 Location/Qualifiers
source                  1..118
                        mol_type = protein
                        organism = synthetic construct
SEQUENCE: 80
QVQLVQSGGG LVQPGGSLRL SCAASGFSYS DYWMHWVRQA PGKGLEWVSD ISRLSPYTNY  60
ADSVKGRFTI SRDNAKNTLY LQLNSLRAED TAMYYCARGL DARRMSYWGQ GTLVTVSS    118

SEQ ID NO: 81           moltype = AA  length = 118
FEATURE                 Location/Qualifiers
source                  1..118
                        mol_type = protein
                        organism = synthetic construct
SEQUENCE: 81
QVQLVQSGGG LVQPGGSLRL SCAASGFTHH SYWLHWVRQA PGKGLEWVSD ISRLSPYTNY  60
ADSVKGRFTI SRDNAKNTLY LQLNSLRAED TAMYYCARGM DARRMDYWGQ GTLVTVSS    118

SEQ ID NO: 82           moltype = AA  length = 111
FEATURE                 Location/Qualifiers
source                  1..111
```

```
                        mol_type = protein
                        organism = synthetic construct
SEQUENCE: 82
QSVLTQPPSA SGTPGQRVTI SCTGSSSNIG AGYVVHWYQQ LPGTAPKLLI YRNNQRPSGV  60
PDRFSGSKSG TSASLAISGL RSEDEADYYC AAWDDSLNGW LFGGGTKLTV L           111

SEQ ID NO: 83           moltype = AA  length = 112
FEATURE                 Location/Qualifiers
source                  1..112
                        mol_type = protein
                        organism = synthetic construct
SEQUENCE: 83
DIQLTQSPSS VSVSVGERVT IDCTGSGTNI GAGYVVHWYQ QKPGQAPQLL IYRNNLRPSG  60
VPDRFSGSKS GTDATLTISS LQAEDAAVYY CASWDDRHQA WLFGQGTKLE IK          112

SEQ ID NO: 84           moltype = AA  length = 112
FEATURE                 Location/Qualifiers
source                  1..112
                        mol_type = protein
                        organism = synthetic construct
SEQUENCE: 84
DIQLTQSPSS VSVSVGERVT IDCTGSSSNI GAGYVVHWYQ QKPGQAPQLL IYRNNLRPSG  60
VPDRFSGSKS GTDATLTISS LQAEDAAVYY CASWDDSLQA WLFGQGTKLE IK          112

SEQ ID NO: 85           moltype = AA  length = 112
FEATURE                 Location/Qualifiers
source                  1..112
                        mol_type = protein
                        organism = synthetic construct
SEQUENCE: 85
DIQLTQSPSS VSVSVGERVT IDCTGSSSNL GAGYVNHWYQ QKPGQAPQLL MYRNNQRPSG  60
VPDRFSGSKS GTDATLTISS LQAEDAAVYY CASWDDHSSA WLFGQGTKLE IK          112

SEQ ID NO: 86           moltype = AA  length = 112
FEATURE                 Location/Qualifiers
source                  1..112
                        mol_type = protein
                        organism = synthetic construct
SEQUENCE: 86
DIQLTQSPSS VSVSVGERVT IDCTGSSTNL GAGYVVHWYQ QKPGQAPQLL IYRNNQRPSG  60
VPDRFSGSKS GTDATLTISS LQAEDAAVYY CAAWDDSVSG WLFGQGTKLE IK          112

SEQ ID NO: 87           moltype = AA  length = 112
FEATURE                 Location/Qualifiers
source                  1..112
                        mol_type = protein
                        organism = synthetic construct
SEQUENCE: 87
DIQLTQSPSS VSVSVGERVT IDCTGSSSNL GGGYVVHWYQ QKPGQAPQLL IFRNNQRPSG  60
VPDRFSGSKS GTDATLTISS LQAEDAAVYY CASWDDSLQG WLFGQGTKLE IK          112

SEQ ID NO: 88           moltype = AA  length = 112
FEATURE                 Location/Qualifiers
source                  1..112
                        mol_type = protein
                        organism = synthetic construct
SEQUENCE: 88
DIQLTQSPSS VSVSVGERVT IDCTGSASNI GAGYVVHWYQ QKPGQAPQLL IYRNNVRPSG  60
VPDRFSGSKS GTDATLTISS LQAEDAAVYY CAAWDDHRTA WLFGQGTKLE IK          112

SEQ ID NO: 89           moltype = AA  length = 112
FEATURE                 Location/Qualifiers
source                  1..112
                        mol_type = protein
                        organism = synthetic construct
SEQUENCE: 89
DIQLTQSPSS VSVSVGERVT IDCTGSSSNI GHGYVVHWYQ QKPGQAPQLK IYRNNQRPSG  60
VPDRFSGSKS GTDATLTISS LQAEDAAVYY CAAWDDSLNG WLFGQGTKLE IK          112

SEQ ID NO: 90           moltype = AA  length = 112
FEATURE                 Location/Qualifiers
source                  1..112
                        mol_type = protein
                        organism = synthetic construct
SEQUENCE: 90
DIQLTQSPSS VSVSVGERVT IDCTGSSSNL GAGYVVHWYQ QKPGQAPQHL IYRNNQRPSG  60
VPDRFSGSKS GTDATLTISS LQAEDAAVYY CASWDDSHMA WLFGQGTKLE IK          112

SEQ ID NO: 91           moltype = AA  length = 112
```

```
FEATURE                 Location/Qualifiers
source                  1..112
                        mol_type = protein
                        organism = synthetic construct
SEQUENCE: 91
DIQLTQSPSS VSVSVGERVT IDCTGSTSNL GAGYVVHWYQ QKPGQAPQLL IYRHHQRPSG  60
VPDRFSGSKS GTDATLTISS LQAEDAAVYY CASWDDSHMA WLFGQGTKLE IK          112

SEQ ID NO: 92           moltype = AA  length = 112
FEATURE                 Location/Qualifiers
source                  1..112
                        mol_type = protein
                        organism = synthetic construct
SEQUENCE: 92
DIQLTQSPSS VSVSVGERVT IDCTGSSSNL GAGYVVHWYQ QKPGQAPQLL IYRHHQKPSG  60
VPDRFSGSKS GTDATLTISS LQAEDAAVYY CASWDDSHMA WLFGQGTKLE IK          112

SEQ ID NO: 93           moltype = AA  length = 112
FEATURE                 Location/Qualifiers
source                  1..112
                        mol_type = protein
                        organism = synthetic construct
SEQUENCE: 93
DIQLTQSPSS VSVSVGERVT IDCTGSSTNL GAGYVVHWYQ QKPGQAPQLL IYRHHQRPSG  60
VPDRFSGSKS GTDATLTISS LQAEDAAVYY CASWDDSHMA WLFGQGTKLE IK          112

SEQ ID NO: 94           moltype = AA  length = 112
FEATURE                 Location/Qualifiers
source                  1..112
                        mol_type = protein
                        organism = synthetic construct
SEQUENCE: 94
DIQLTQSPSS VSVSVGERVT IDCTGSSSNI GGGYVVHWYQ QKPGQAPQLL IYRNNQRPSG  60
VPDRFSGSKS GTDATLTISS LQAEDAAVYY CAAWDDERNG WLFGQGTKLE IK          112

SEQ ID NO: 95           moltype = AA  length = 112
FEATURE                 Location/Qualifiers
source                  1..112
                        mol_type = protein
                        organism = synthetic construct
SEQUENCE: 95
DIQLTQSPSS VSVSVGERVT IDCTGSSSNI GAGYVVHWYQ QKPGQAPQLL IYRNNQRPSG  60
VPDRFSGSKS GTDATLTISS LQAEDAAVYY CAAHDDELHG WLFGQGTKLE IK          112

SEQ ID NO: 96           moltype = AA  length = 112
FEATURE                 Location/Qualifiers
source                  1..112
                        mol_type = protein
                        organism = synthetic construct
SEQUENCE: 96
DIQLTQSPSS VSVSVGERVT IDCTGSSSNI HGGYVVHWYQ QKPGQAPQLL IYRNNQRPSG  60
VPDRFSGSKS GTDATLTISS LQAEDAAVYY CAAWDDSRNG WLFGQGTKLE IK          112

SEQ ID NO: 97           moltype = AA  length = 326
FEATURE                 Location/Qualifiers
source                  1..326
                        mol_type = protein
                        organism = synthetic construct
SEQUENCE: 97
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHNHYTQKSL SLSPGK                                       326

SEQ ID NO: 98           moltype = AA  length = 330
FEATURE                 Location/Qualifiers
source                  1..330
                        mol_type = protein
                        organism = synthetic construct
SEQUENCE: 98
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVSVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPGK                                   330
```

-continued

```
SEQ ID NO: 99          moltype = AA  length = 106
FEATURE                Location/Qualifiers
source                 1..106
                       mol_type = protein
                       organism = synthetic construct
SEQUENCE: 99
GQPKAAPSVT LFPPSSEELQ ANKATLVCLI SDFYPGAVTV AWKADSSPVK AGVETTTPSK  60
QSNNKYAASS YLSLTPEQWK SHRSYSCQVT HEGSTVEKTV APTECS                 106

SEQ ID NO: 100         moltype = AA  length = 107
FEATURE                Location/Qualifiers
source                 1..107
                       mol_type = protein
                       organism = synthetic construct
SEQUENCE: 100
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 101         moltype = AA  length = 444
FEATURE                Location/Qualifiers
source                 1..444
                       mol_type = protein
                       organism = synthetic construct
SEQUENCE: 101
EVQLLESGGG LVQPGGSLRL SCAASGFTFS SYWMHWVRQA PGKGLEWVSD IARLSSYTNY  60
ADSVKGRFTI SRDNSKNTLY LQMNSLRAED TAVYYCARGL DARRMDYWGQ GTLVTVSSAS  120
TKGPSVFPLA PCSRSTSEST AALGCLVKDY FPEPVTVSWN SGALTSGVHT FPAVLQSSGL  180
YSLSSVVTVP SSNFGTQTYT CNVDHKPSNT KVDKTVERKC CVECPPCPAP PVAGPSVFLF  240
PPKPKDTLMI SRTPEVTCVV VDVSHEDPEV QFNWYVDGVE VHNAKTKPRE EQFNSTFRVV  300
SVLTVVHQDW LNGKEYKCKV SNKGLPAPIE KTISKTKGQP REPQVYTLPP SREEMTKNQV  360
SLTCLVKGFY PSDIAVEWES NGQPENNYKT TPPMLDSDGS FFLYSKLTVD KSRWQQGNVF  420
SCSVMHEALH NHYTQKSLSL SPGK                                         444

SEQ ID NO: 102         moltype = AA  length = 448
FEATURE                Location/Qualifiers
source                 1..448
                       mol_type = protein
                       organism = synthetic construct
SEQUENCE: 102
QVQLVQSGGG LVQPGGSLRL SCAASGFTYS DYWMHWVRQA PGKGLEWVSD ISRLKPYTNY  60
ADSVKGRFTI SRDNAKNTLY LQLNSLRAED TAMYYCARGL DARRMDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVSVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVLH EALHSHYTQK SLSLSPGK                                     448

SEQ ID NO: 103         moltype = AA  length = 448
FEATURE                Location/Qualifiers
source                 1..448
                       mol_type = protein
                       organism = synthetic construct
SEQUENCE: 103
QVQLVQSGGG LVQPGGSLRL SCAASGFSYS SYWMHWVRQA PGKGLEWVSD ISRLSPYTGY  60
ADSVKGRFTI SRDNAKNTLY LQLNSLRAED TAMYYCARGM DAKRMDHWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVSVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVLH EALHSHYTQK SLSLSPGK                                     448

SEQ ID NO: 104         moltype = AA  length = 448
FEATURE                Location/Qualifiers
source                 1..448
                       mol_type = protein
                       organism = synthetic construct
SEQUENCE: 104
QVQLVQSGGG LVQPGGSLRL SCAASGFTYS DFWMHWVRQA PGKGLEWMSD ISRLSPYTNY  60
ADSVKGRFTI SRDNAKNTLY LQLNSLRAED TAMYYCARGL DARRMDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVSVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVLH EALHSHYTQK SLSLSPGK                                     448

SEQ ID NO: 105         moltype = AA  length = 448
```

```
FEATURE                Location/Qualifiers
source                 1..448
                       mol_type = protein
                       organism = synthetic construct
SEQUENCE: 105
QVQLVQSGGG LVQPGGSLRL SCAASGFSYV SYWMHWVRQA PGKGLEWVSD ISRISPYTNY  60
ADSVKGRFTI SRDNAKNTLY LQLNSLRAED TAMYYCARGL DARRMDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVSVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVLH EALHSHYTQK SLSLSPGK                                    448

SEQ ID NO: 106         moltype = AA  length = 448
FEATURE                Location/Qualifiers
source                 1..448
                       mol_type = protein
                       organism = synthetic construct
SEQUENCE: 106
QVQLVQSGGG LVQPGGSLRL SCAASGFTYS DYWMHWVRQA PGKGLEWMSD ISRLSPYTGY  60
ADSVKGRFTI SRDNAKNTLY LQLNSLRAED TAMYYCARGL DARRMDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVSVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVLH EALHSHYTQK SLSLSPGK                                    448

SEQ ID NO: 107         moltype = AA  length = 448
FEATURE                Location/Qualifiers
source                 1..448
                       mol_type = protein
                       organism = synthetic construct
SEQUENCE: 107
QVQLVQSGGG LVQPGGSLRL SCAASGFSYS DYWMHWVRQA PGKGLEWVSD ISRLSPYTNY  60
ADSVKGRFTI SRDNAKNTLY LQLNSLRAED TAMYYCARGL DARRMSYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVSVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVLH EALHSHYTQK SLSLSPGK                                    448

SEQ ID NO: 108         moltype = AA  length = 14
FEATURE                Location/Qualifiers
source                 1..14
                       mol_type = protein
                       organism = synthetic construct
VARIANT                4
                       note = X is G, S, or T.
VARIANT                5
                       note = X is S or T.
VARIANT                7
                       note = X is I or L.
VARIANT                8
                       note = X is G or H.
VARIANT                9
                       note = X is A, G, or H.
SEQUENCE: 108
TGSXXNXXXG YVVH                                                   14

SEQ ID NO: 109         moltype = AA  length = 448
FEATURE                Location/Qualifiers
source                 1..448
                       mol_type = protein
                       organism = synthetic construct
SEQUENCE: 109
QVQLVQSGGG LVQPGGSLRL SCAASGFTHH SYWLHWVRQA PGKGLEWVSD ISRLSPYTNY  60
ADSVKGRFTI SRDNAKNTLY LQLNSLRAED TAMYYCARGM DARRMDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVSVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVLH EALHSHYTQK SLSLSPGK                                    448

SEQ ID NO: 110         moltype = AA  length = 11
FEATURE                Location/Qualifiers
```

```
source                  1..11
                        mol_type = protein
                        organism = synthetic construct
VARIANT                 2
                        note = X is A or S.
VARIANT                 6
                        note = X is E, R, or S.
VARIANT                 7
                        note = X is H, L, or R.
VARIANT                 8
                        note = X is N or Q.
VARIANT                 9
                        note = X is A or G.
SEQUENCE: 110
AXWDDXXXXW L                                                        11

SEQ ID NO: 111          moltype = AA  length = 448
FEATURE                 Location/Qualifiers
source                  1..448
                        mol_type = protein
                        organism = synthetic construct
SEQUENCE: 111
QVQLVQSGGG LVQPGGSLRL SCAASGFTYS SHWLHWVRQA PGKGLEWVSD ISRLSPYTNY  60
ADSVKGRFTI SRDNAKNTLY LQLNSLRAED TAMYYCAKGL DARRMDHWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVSVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVLH EALHSHYTQK SLSLSPGK                                      448

SEQ ID NO: 112          moltype = AA  length = 448
FEATURE                 Location/Qualifiers
source                  1..448
                        mol_type = protein
                        organism = synthetic construct
SEQUENCE: 112
QVQLVQSGGG LVQPGGSLRL SCAASGFTHS SYWMHWVRQA PGKGLEWVSD ISRLSPYHNY  60
ADSVKGRFTI SRDNAKNTLY LQLNSLRAED TAMYYCSRGL DARRMDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVSVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVLH EALHSHYTQK SLSLSPGK                                      448

SEQ ID NO: 113          moltype = AA  length = 448
FEATURE                 Location/Qualifiers
source                  1..448
                        mol_type = protein
                        organism = synthetic construct
SEQUENCE: 113
QVQLVQSGGG LVQPGGSLRL SCAASGFTHH SYWLHWVRQA PGKGLEWVSD ISRLSPYTNY  60
ADSVKGRFTI SRDNAKNTLY LQLNSLRAED TAMYYCARGM DARRMDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVSVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVLH EALHSHYTQK SLSLSPGK                                      448

SEQ ID NO: 114          moltype = AA  length = 448
FEATURE                 Location/Qualifiers
source                  1..448
                        mol_type = protein
                        organism = synthetic construct
SEQUENCE: 114
QVQLVQSGGG LVQPGGSLRL SCAASGFSYS DYWMHWVRQA PGKGLEWVSD ISRLSPYTNY  60
ADSVKGRFTI SRDNAKNTLY LQLNSLRAED TAMYYCARGL DARRMSYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVSVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVLH EALHSHYTQK SLSLSPGK                                      448

SEQ ID NO: 115          moltype = AA  length = 448
FEATURE                 Location/Qualifiers
source                  1..448
```

-continued

```
                          mol_type = protein
                          organism = synthetic construct
SEQUENCE: 115
QVQLVQSGGG LVQPGGSLRL SCAASGFTHH SYWLHWVRQA PGKGLEWVSD ISRLSPYTNY  60
ADSVKGRFTI SRDNAKNTLY LQLNSLRAED TAMYYCARGM DARRMDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVSVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVLH EALHSHYTQK SLSLSPGK                                    448

SEQ ID NO: 116            moltype = AA  length = 217
FEATURE                   Location/Qualifiers
source                    1..217
                          mol_type = protein
                          organism = synthetic construct
SEQUENCE: 116
QSVLTQPPSA SGTPGQRVTI SCTGSSSNIG AGYVVHWYQQ LPGTAPKLLI YRNNQRPSGV  60
PDRFSGSKSG TSASLAISGL RSEDEADYYC AAWDDSLNGW LFGGGTKLTV LGQPKAAPSV  120
TLFPPSSEEL QANKATLVCL ISDFYPGAVT VAWKADSSPV KAGVETTTPS KQSNNKYAAS  180
SYLSLTPEQW KSHRSYSCQV THEGSTVEKT VAPTECS                          217

SEQ ID NO: 117            moltype = AA  length = 219
FEATURE                   Location/Qualifiers
source                    1..219
                          mol_type = protein
                          organism = synthetic construct
SEQUENCE: 117
DIQLTQSPSS VSVSVGERVT IDCTGSGTNI GAGYVVHWYQ QKPGQAPQLL IYRNNLRPSG  60
VPDRFSGSKS GTDATLTISS LQAEDAAVYY CASWDDRHQA WLFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 118            moltype = AA  length = 219
FEATURE                   Location/Qualifiers
source                    1..219
                          mol_type = protein
                          organism = synthetic construct
SEQUENCE: 118
DIQLTQSPSS VSVSVGERVT IDCTGSSSNI GAGYVVHWYQ QKPGQAPQLL IYRNNLRPSG  60
VPDRFSGSKS GTDATLTISS LQAEDAAVYY CASWDDSLQA WLFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 119            moltype = AA  length = 219
FEATURE                   Location/Qualifiers
source                    1..219
                          mol_type = protein
                          organism = synthetic construct
SEQUENCE: 119
DIQLTQSPSS VSVSVGERVT IDCTGSSSNL GAGYVNHWYQ QKPGQAPQLL MYRNNQRPSG  60
VPDRFSGSKS GTDATLTISS LQAEDAAVYY CASWDDHSSA WLFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 120            moltype = AA  length = 219
FEATURE                   Location/Qualifiers
source                    1..219
                          mol_type = protein
                          organism = synthetic construct
SEQUENCE: 120
DIQLTQSPSS VSVSVGERVT IDCTGSSTNL GAGYVVHWYQ QKPGQAPQLL IYRNNQRPSG  60
VPDRFSGSKS GTDATLTISS LQAEDAAVYY CAAWDDSVSG WLFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 121            moltype = AA  length = 219
FEATURE                   Location/Qualifiers
source                    1..219
                          mol_type = protein
                          organism = synthetic construct
SEQUENCE: 121
DIQLTQSPSS VSVSVGERVT IDCTGSSSNL GGGYVVHWYQ QKPGQAPQLL IFRNNQRPSG  60
VPDRFSGSKS GTDATLTISS LQAEDAAVYY CASWDDSLQG WLFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 122            moltype = AA  length = 219
```

```
FEATURE                Location/Qualifiers
source                 1..219
                       mol_type = protein
                       organism = synthetic construct
SEQUENCE: 122
DIQLTQSPSS VSVSVGERVT IDCTGSASNI GAGYVVHWYQ QKPGQAPQLL IYRNNVRPSG  60
VPDRFSGSKS GTDATLTISS LQAEDAAVYY CAAWDDHRTA WLFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 123         moltype = AA  length = 219
FEATURE                Location/Qualifiers
source                 1..219
                       mol_type = protein
                       organism = synthetic construct
SEQUENCE: 123
DIQLTQSPSS VSVSVGERVT IDCTGSSSNI GHGYVVHWYQ QKPGQAPQLK IYRNNQRPSG  60
VPDRFSGSKS GTDATLTISS LQAEDAAVYY CAAWDDSLNG WLFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 124         moltype = AA  length = 219
FEATURE                Location/Qualifiers
source                 1..219
                       mol_type = protein
                       organism = synthetic construct
SEQUENCE: 124
DIQLTQSPSS VSVSVGERVT IDCTGSSSNL GAGYVVHWYQ QKPGQAPQHL IYRNNQRPSG  60
VPDRFSGSKS GTDATLTISS LQAEDAAVYY CASWDDSHMA WLFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 125         moltype = AA  length = 219
FEATURE                Location/Qualifiers
source                 1..219
                       mol_type = protein
                       organism = synthetic construct
SEQUENCE: 125
DIQLTQSPSS VSVSVGERVT IDCTGSTSNL GAGYVVHWYQ QKPGQAPQLL IYRHHQRPSG  60
VPDRFSGSKS GTDATLTISS LQAEDAAVYY CASWDDSHMA WLFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 126         moltype = AA  length = 219
FEATURE                Location/Qualifiers
source                 1..219
                       mol_type = protein
                       organism = synthetic construct
SEQUENCE: 126
DIQLTQSPSS VSVSVGERVT IDCTGSSSNL GAGYVVHWYQ QKPGQAPQLL IYRHHQKPSG  60
VPDRFSGSKS GTDATLTISS LQAEDAAVYY CASWDDSHMA WLFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 127         moltype = AA  length = 219
FEATURE                Location/Qualifiers
source                 1..219
                       mol_type = protein
                       organism = synthetic construct
SEQUENCE: 127
DIQLTQSPSS VSVSVGERVT IDCTGSSTNL GAGYVVHWYQ QKPGQAPQLL IYRHHQRPSG  60
VPDRFSGSKS GTDATLTISS LQAEDAAVYY CASWDDSHMA WLFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 128         moltype = AA  length = 219
FEATURE                Location/Qualifiers
source                 1..219
                       mol_type = protein
                       organism = synthetic construct
SEQUENCE: 128
DIQLTQSPSS VSVSVGERVT IDCTGSSSNI GGGYVVHWYQ QKPGQAPQLL IYRNNQRPSG  60
VPDRFSGSKS GTDATLTISS LQAEDAAVYY CAAWDDERNG WLFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 129         moltype = AA  length = 219
FEATURE                Location/Qualifiers
source                 1..219
```

```
                        mol_type = protein
                        organism = synthetic construct
SEQUENCE: 129
DIQLTQSPSS VSVSVGERVT IDCTGSSSNI GAGYVVHWYQ QKPGQAPQLL IYRNNQRPSG  60
VPDRFSGSKS GTDATLTISS LQAEDAAVYY CAAHDDELHG WLFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 130          moltype = AA  length = 219
FEATURE                 Location/Qualifiers
source                  1..219
                        mol_type = protein
                        organism = synthetic construct
SEQUENCE: 130
DIQLTQSPSS VSVSVGERVT IDCTGSSSNI HGGYVVHWYQ QKPGQAPQLL IYRNNQRPSG  60
VPDRFSGSKS GTDATLTISS LQAEDAAVYY CAAWDDSRNG WLFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 131          moltype = AA  length = 17
FEATURE                 Location/Qualifiers
source                  1..17
                        mol_type = protein
                        organism = synthetic construct
VARIANT                 5
                        note = X is I or L.
VARIANT                 6
                        note = X is K or S.
VARIANT                 9
                        note = X is H or T.
VARIANT                 10
                        note = X is G or N.
SEQUENCE: 131
DISRXXPYXX YADSVKG                                                 17

SEQ ID NO: 132          moltype = AA  length = 9
FEATURE                 Location/Qualifiers
source                  1..9
                        mol_type = protein
                        organism = synthetic construct
VARIANT                 2
                        note = X is M or L.
VARIANT                 5
                        note = X is K or R.
VARIANT                 8
                        note = X is D or S.
VARIANT                 9
                        note = X is H or Y.
SEQUENCE: 132
GXDAXRMXX                                                          9

SEQ ID NO: 133          moltype = AA  length = 14
FEATURE                 Location/Qualifiers
source                  1..14
                        mol_type = protein
                        organism = synthetic construct
VARIANT                 4
                        note = X is A, G, S, or T.
VARIANT                 5
                        note = X is S or T.
VARIANT                 7
                        note = X is I or L.
VARIANT                 8
                        note = X is G or H.
VARIANT                 9
                        note = X is A, G, or H.
VARIANT                 13
                        note = X is N or V.
SEQUENCE: 133
TGSXXNXXXG YVXH                                                    14

SEQ ID NO: 134          moltype = AA  length = 11
FEATURE                 Location/Qualifiers
source                  1..11
                        mol_type = protein
                        organism = synthetic construct
VARIANT                 2
                        note = X is A or S.
VARIANT                 3
```

```
                        note = X is H or W.
VARIANT                 6
                        note = X is E, H, R, or S.
VARIANT                 7
                        note = X is H, L, R, S, or V.
VARIANT                 8
                        note = X is H, M, N, Q, S, or T
VARIANT                 9
                        note = X is A or G.
SEQUENCE: 134
AXXDDXXXXW L                                                     11

SEQ ID NO: 135          moltype = AA  length = 30
FEATURE                 Location/Qualifiers
source                  1..30
                        mol_type = protein
                        organism = synthetic construct
VARIANT                 28
                        note = X is S or T.
VARIANT                 29
                        note = X is H or Y.
VARIANT                 30
                        note = X is H, S, or V.
SEQUENCE: 135
QVQLVQSGGG LVQPGGSLRL SCAASGFXXX                                 30

SEQ ID NO: 136          moltype = AA  length = 14
FEATURE                 Location/Qualifiers
source                  1..14
                        mol_type = protein
                        organism = synthetic construct
VARIANT                 13
                        note = X is V or M.
SEQUENCE: 136
WVRQAPGKGL EWXS                                                  14

SEQ ID NO: 137          moltype = AA  length = 33
FEATURE                 Location/Qualifiers
source                  1..33
                        mol_type = protein
                        organism = synthetic construct
VARIANT                 32
                        note = X is A or S.
VARIANT                 33
                        note = X is K or R.
SEQUENCE: 137
GRFTISRDNA KNTLYLQLNS LRAEDTAMYY CXX                             33

SEQ ID NO: 138          moltype = AA  length = 15
FEATURE                 Location/Qualifiers
source                  1..15
                        mol_type = protein
                        organism = synthetic construct
VARIANT                 12
                        note = X is H or L.
VARIANT                 13
                        note = X is K or L.
VARIANT                 14
                        note = X is I or M.
VARIANT                 15
                        note = X is F or Y.
SEQUENCE: 138
WYQQKPGQAP QXXXX                                                 15

SEQ ID NO: 139          moltype = AA  length = 9
FEATURE                 Location/Qualifiers
source                  1..9
                        mol_type = protein
                        organism = synthetic construct
VARIANT                 2
                        note = X is M or L.
VARIANT                 8
                        note = X is D or S.
SEQUENCE: 139
GXDARRMXY                                                        9

SEQ ID NO: 140          moltype = AA  length = 14
FEATURE                 Location/Qualifiers
source                  1..14
```

```
                         mol_type = protein
                         organism = synthetic construct
VARIANT                  4
                         note = X is G, or S.
VARIANT                  5
                         note = X is S or T.
VARIANT                  9
                         note = X is A, G, or H.
SEQUENCE: 140
TGSXXNIGXG YVVH                                              14

SEQ ID NO: 141           moltype = AA  length = 11
FEATURE                  Location/Qualifiers
source                   1..11
                         mol_type = protein
                         organism = synthetic construct
VARIANT                  2
                         note = X is A or S.
VARIANT                  3
                         note = X is H or W.
VARIANT                  6
                         note = X is E, R, or S.
VARIANT                  7
                         note = X is H, L, or R.
VARIANT                  8
                         note = X is N, M, or Q.
VARIANT                  9
                         note = X is A or G.
SEQUENCE: 141
AXXDDXXXXW L                                                 11

SEQ ID NO: 142           moltype = AA  length = 17
FEATURE                  Location/Qualifiers
source                   1..17
                         mol_type = protein
                         organism = synthetic construct
VARIANT                  2
                         note = X is I or V.
VARIANT                  5
                         note = X is I, L, F, V, or M.
VARIANT                  6
                         note = X is K,S, L, N, A, G, Q, P, Y, T, V, M, I, W, E, D,
                          F, R, or H.
VARIANT                  7
                         note = X is P, G, D,or S.
VARIANT                  8
                         note = X is Y, W, or F.
VARIANT                  9
                         note = X is H,T V, R, M, or S.
VARIANT                  10
                         note = X is G, N, A, G, S, or Q.
VARIANT                  12
                         note = X is A, K, L, H, I, M, V, or R.
VARIANT                  13
                         note = X is D, S, W, G, K, Q, A, E, L, M, H, Y, T, F, I, N,
                          or R.
VARIANT                  14
                         note = X is S, D, A, R, T, K, N, M, P, H, W, Y, V, F, G, I,
                          L, or Q.
VARIANT                  15
                         note = X is V, M, A, L, T, F, or I.
VARIANT                  16
                         note = X is K, N, Q, A, R, Y, T, W, I, F, V, G, H, S, L, E,
                          D, or M.
VARIANT                  17
                         note = X is G, H, N, T, F, R, K, Y, Q, S, D, P, or A.
SEQUENCE: 142
DXSRXXXXXX YXXXXXX                                           17

SEQ ID NO: 143           moltype = AA  length = 9
FEATURE                  Location/Qualifiers
source                   1..9
                         mol_type = protein
                         organism = synthetic construct
VARIANT                  2
                         note = X is M, L, T, E, A, R, or Q.
VARIANT                  4
                         note = X is A, D, E, or S.
VARIANT                  5
```

-continued

```
                        note = X is K, R, A, M, I, K, or V.
VARIANT                 8
                        note = X is D, S, or E.
VARIANT                 9
                        note = X is H, Y, F, N, R, K, W, or E.
SEQUENCE: 143
GXDXXRMXX                                                         9

SEQ ID NO: 144          moltype = AA  length = 14
FEATURE                 Location/Qualifiers
source                  1..14
                        mol_type = protein
                        organism = synthetic construct
VARIANT                 1
                        note = X is T, I, R, G, F, S, K, D, A, L, W, H, M, V, Y, Q,
                         or E.
VARIANT                 3
                        note = X is S, D, Q, Y, G, E, H, W, R, T, or A.
VARIANT                 4
                        note = X is A, G, S, T, F, P, R, M, E, D, H, I, Y, W, L, V,
                         N, Q, or K.
VARIANT                 5
                        note = X is S, T, Y, D, A, E, Q, N, or H.
VARIANT                 7
                        note = X is I, L, M, or V.
VARIANT                 8
                        note = X is G or H.
VARIANT                 9
                        note = X is A, G, H, F, Y, Q, S, or M.
VARIANT                 13
                        note = X is N, V, S, N, L, A, or T.
VARIANT                 14
                        note = X is H or Q.
SEQUENCE: 144
XGXXXNXXXG YVXX                                                   14

SEQ ID NO: 145          moltype = AA  length = 7
FEATURE                 Location/Qualifiers
source                  1..7
                        mol_type = protein
                        organism = synthetic construct
VARIANT                 2
                        note = X is H or N.
VARIANT                 3
                        note = X is H or N.
VARIANT                 4
                        note = X is L or Q.
SEQUENCE: 145
RXXXRPS                                                           7

SEQ ID NO: 146          moltype = AA  length = 7
FEATURE                 Location/Qualifiers
source                  1..7
                        mol_type = protein
                        organism = synthetic construct
VARIANT                 4
                        note = X is L or Q.
SEQUENCE: 146
RNNXRPS                                                           7
```

What is claimed is:

1. An antibody binding to prolactin receptor (PRLR) (anti-PRLR antibody) wherein the antibody comprises:

(a) a heavy chain variable region (VH) comprising a heavy chain complementarity determining region 1 (HCDR1), a heavy chain complementarity determining region 2 (HCDR2), and a heavy chain complementarity determining region 3 (HCDR3), wherein the HCDR1, HCDR2, and HCDR3 comprises the amino acid sequences of SEQ ID NOs: 2, 7, and 12, respectively; and (b) a light chain variable region (VL) comprising a light chain complementarity determining region 1 (LCDR1), a light chain complementarity determining region 2 (LCDR2), and a light chain complementarity determining region 3 (LCDR3), wherein the LCDR1, LCDR2, and LCDR3 comprise the amino acid sequences of SEQ ID NOs: 18, 29, and 34, respectively.

2. The anti-PRLR antibody of claim 1, wherein the VH comprises heavy chain framework regions (HC FRs) derived from IGHV3-66*01; and wherein the VL comprises light chain framework regions (LC FRs) derived from IGKV4-1*01.

3. The anti-PRLR antibody of claim 2, wherein the VH comprises the heavy chain framework regions as below:

(a) HC FR1 comprising the amino acid sequence of QVQLVQSGGGLVQPGGSLRLSCAASGF$X_{28}X_{29}X_{30}$ (SEQ ID NO: 135), wherein $X_{28}$ is S or T; $X_{29}$ is H or Y; and $X_{30}$ is H, S, or V;

(b) HC FR2 comprising the amino acid sequence of WVRQAPGKGLEW$X_{31}$S (SEQ ID NO: 136), wherein $X_{31}$ is M or V;

(c) HC FR3 comprising the amino acid sequence of GRFTISRDNAKNTLYLQLNSLRAEDTAMYYC $X_{32}X_{33}$ (SEQ ID NO: 137), wherein $X_{32}$ is A or S; and $X_{33}$ is K or R; and (d) HC FR4 comprising the amino acid sequence of WGQGTLVTVSS (SEQ ID NO: 55).

4. The anti-PRLR antibody of claim 3, wherein $X_{28}$ is S or T; $X_{29}$ is H or Y; $X_{30}$ is H or S; $X_{31}$ is M or V; $X_{32}$ is A; and $X_{33}$ is R.

5. The anti-PRLR antibody of claim 2, wherein the VL comprises the light chain framework regions as below:

(a) LC FR 1 comprising the amino acid sequence of DIQLTQSPSSVSVSVGERVTIDC (SEQ ID NO: 57);

(b) LC FR2 comprising the amino acid sequence of WYQQKPGQAPQ$X_{35}X_{36}X_{37}X_{38}$ (SEQ ID NO: 138), wherein $X_{35}$ is H or L; $X_{36}$ is K or L; $X_{37}$ is I or M; and $X_{38}$ is F or Y;

(c) LC FR3 comprising the amino acid sequence of GVPDRFSGSKSGTDATLTISSLQAEDAAVYYC (SEQ ID NO: 64); and (d) LC FR4 comprising the amino acid sequence of FGQGTKLEIK (SEQ ID NO: 66).

6. The anti-PRLR antibody of claim 1, wherein the antibody comprises:

the VH comprising SEQ ID NO: 68 and the VL comprising SEQ ID NO: 83.

7. The anti-PRLR antibody of claim 1, wherein the antibody is a full-length antibody, an antigen-binding fragment thereof, or a single chain variable fragment (scFv).

8. The anti-PRLR antibody of claim 7, wherein the antibody is a full-length antibody, which is an IgG molecule.

9. The anti-PRLR antibody of claim 8, wherein the antibody comprises a heavy chain comprising the VH and a heavy chain constant region of an IgG1 molecule and a light chain comprising the VL and a light chain constant region.

10. The anti-PRLR antibody of claim 9, wherein the heavy chain constant region is a wild-type IgG1 constant region or a variant thereof; wherein the variant comprises one or more mutations at positions 234, 235, 265, 428, and 434, following the EU numbering system.

11. The anti-PRLR antibody of claim 8, wherein the heavy chain constant region is a variant comprising one or more of the mutations L234A, L235A, D265S, M428L, and N434S.

12. The anti-PRLR antibody of claim 11, wherein the heavy chain constant region comprises any one of SEQ ID NOs: 97-98, and/or wherein the light chain constant region comprises any one of SEQ ID NOs: 99-100.

13. The anti-PRLR antibody of claim 10, wherein the antibody comprises: a heavy chain comprising SEQ ID NO: 102 and a light chain comprising SEQ ID NO: 117.

14. A pharmaceutical composition, comprising the anti-PRLR antibody set forth in claim 1 and a pharmaceutically acceptable carrier.

15. A method for treating a disease associated with PRLR, comprising administering to a subject in need thereof an effective amount of the anti-PRLR antibody set forth in claim 1, or the pharmaceutical composition comprising the anti-PRLR antibody wherein the disease associated with PRLR is a cancer, a reproductive and gynecological disorder, an autoimmune and inflammatory disorder, a dermatological condition, hyperprolactinemia, a cardiovascular disease, androgenetic alopecia or endometriosis.

16. The method of claim 15, wherein the subject is a human patient having the disease associated with PRLR.

17. The method of claim 15, wherein the disease is androgenetic alopecia or endometriosis.

18. A method for restoring hair color in a subject, comprising administering to a subject in need thereof an effective amount of an anti-PRLR antibody; wherein the antibody is set forth in claim 1.

19. The method of claim 17, wherein the antibody comprises a heavy chain comprising SEQ ID NO: 102 and a light chain comprising SEQ ID NO: 117.

20. The method of claim 18, wherein the antibody comprises a heavy chain comprising SEQ ID NO: 102 and a light chain comprising SEQ ID NO: 117.

* * * * *